(12) United States Patent
Schempf et al.

(10) Patent No.: US 6,820,653 B1
(45) Date of Patent: Nov. 23, 2004

(54) PIPE INSPECTION AND REPAIR SYSTEM

(75) Inventors: Hagen Schempf, Pgh, PA (US);
Edward Mutschler, Wexford, PA (US);
Brian Chemel, Salem, MA (US); Scott Boehmke, Pittsburgh, PA (US);
William Crowley, Pgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 09/547,281

(22) Filed: Apr. 12, 2000

Related U.S. Application Data

(60) Provisional application No. 60/128,821, filed on Apr. 12, 1999.

(51) Int. Cl.[7] .................................................. F16I 55/16
(52) U.S. Cl. ........................ 138/98; 138/97; 15/104.05; 15/104.09; 15/104.31
(58) Field of Search ................... 138/97, 98; 15/104.05, 15/104.09, 104.31; 701/28; 901/44, 46, 47; 708/270–271, 845; 327/105–106, 113, 117, 119

(56) References Cited

U.S. PATENT DOCUMENTS

| | | | |
|---|---|---|---|
| 3,681,811 A | * 8/1972 | Amelung et al. | ......... 15/104.05 |
| 3,718,978 A | * 3/1973 | Van Koevering et al. | ..... 138/97 |
| 3,949,292 A | 4/1976 | Beaver et al. | |
| 3,967,194 A | 6/1976 | Beaver et al. | |
| 4,006,359 A | * 2/1977 | Sullins et al. | ............ 250/358 P |
| 4,252,152 A | * 2/1981 | Martin et al. | ................. 138/97 |
| 4,445,088 A | 4/1984 | Schubel | |
| 4,473,921 A | * 10/1984 | Weber et al. | .................. 15/304 |
| 4,601,204 A | * 7/1986 | Fournot et al. | ........... 73/432 R |
| 4,648,454 A | 3/1987 | Yarnell | |
| 4,839,593 A | 6/1989 | Spies | |
| 4,843,319 A | 6/1989 | Lara | |
| 4,843,320 A | 6/1989 | Spies | |
| 4,852,391 A | * 8/1989 | Ruch et al. | .............. 73/40.5 R |
| 4,941,511 A | * 7/1990 | Johansen et al. | ............. 138/89 |
| 5,172,639 A | 12/1992 | Wiesman et al. | |
| 5,363,935 A | * 11/1994 | Schempf et al. | ............. 180/9.1 |
| 5,388,528 A | 2/1995 | Pelrine et al. | |
| 5,416,944 A | * 5/1995 | Eriksson | .................. 15/104.09 |
| 5,461,313 A | 10/1995 | Bohon et al. | |
| 5,528,789 A | * 6/1996 | Rostamo | .................. 15/104.12 |
| 5,736,821 A | 4/1998 | Suyama | |
| 5,773,984 A | 6/1998 | Suyama | |
| 5,878,783 A | * 3/1999 | Smart | .......................... 138/93 |
| 5,899,795 A | * 5/1999 | Penza | ...................... 15/104.09 |
| 5,971,404 A | * 10/1999 | Stoves | ...................... 280/6.154 |
| 6,031,371 A | * 2/2000 | Smart | .......................... 138/97 |
| 6,107,795 A | * 8/2000 | Smart | .......................... 138/97 |
| 6,123,027 A | 9/2000 | Suyama | |

FOREIGN PATENT DOCUMENTS

| | | |
|---|---|---|
| DE | 196 24 275 A | 1/1997 |
| DE | 200 02 929 U | 11/2000 |
| FR | 2 667 519 A | 4/1992 |
| WO | WO 98/12418 A | 3/1998 |
| WO | WO 99/00621 | 1/1999 |

* cited by examiner

*Primary Examiner*—James Hook
(74) *Attorney, Agent, or Firm*—Kirkpatrick & Lockhart LLP

(57) ABSTRACT

A multi-module pipe inspection and repair device. The device includes a base module, a camera module, a sensor module, an MFL module, a brush module, a patch set/test module, and a marker module. Each of the modules may be interconnected to construct one of an inspection device, a preparation device, a marking device, and a repair device.

51 Claims, 56 Drawing Sheets

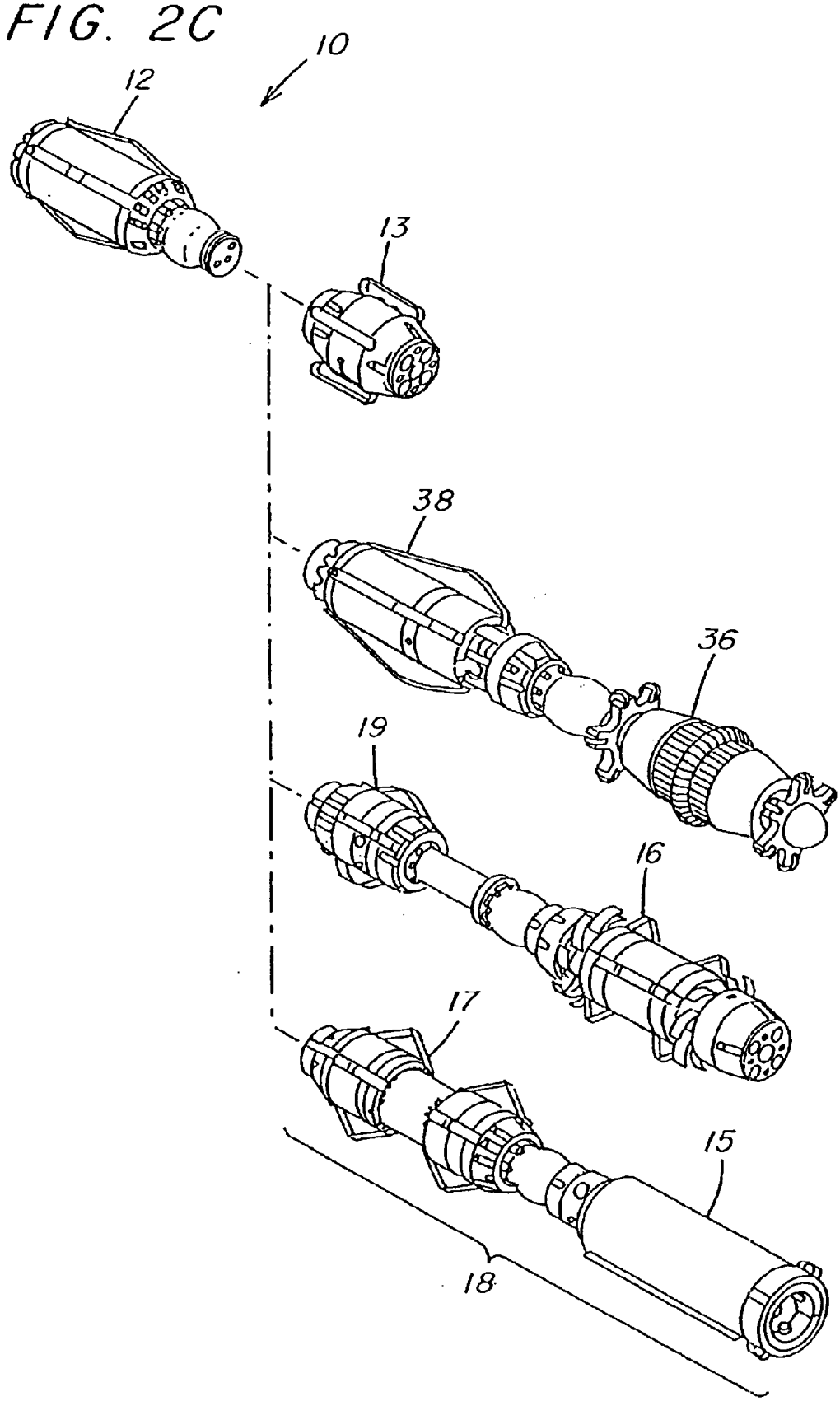

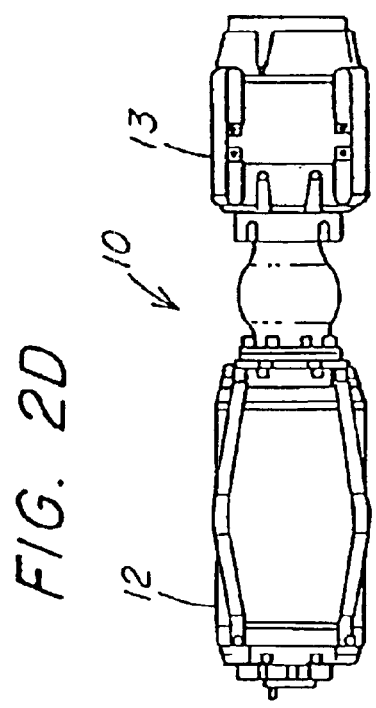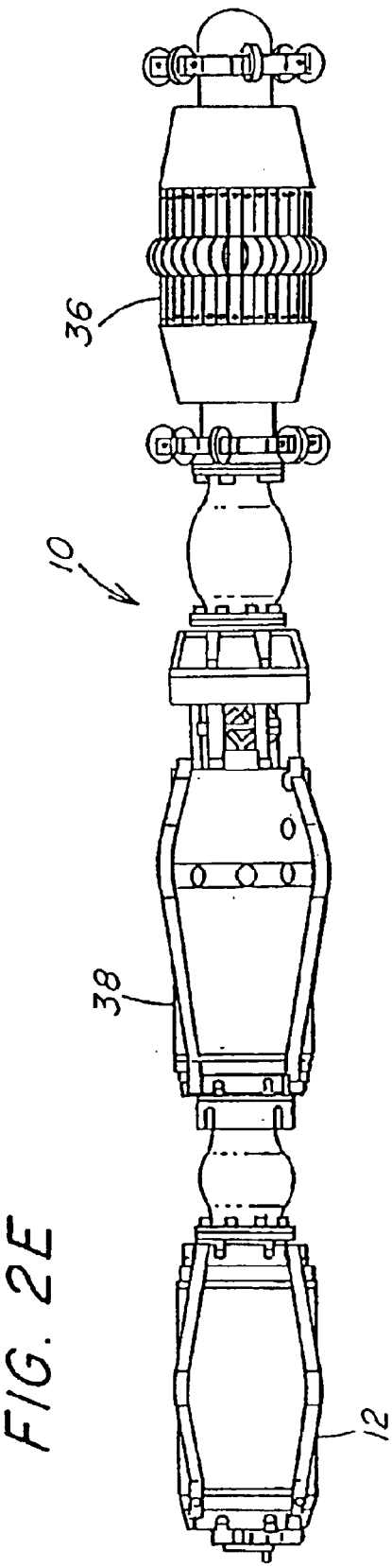
FIG. 2D
FIG. 2E

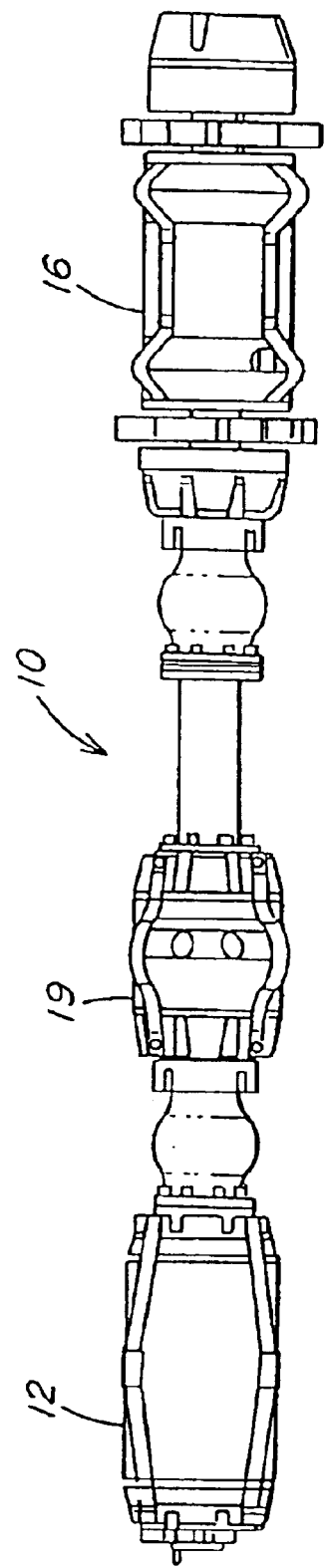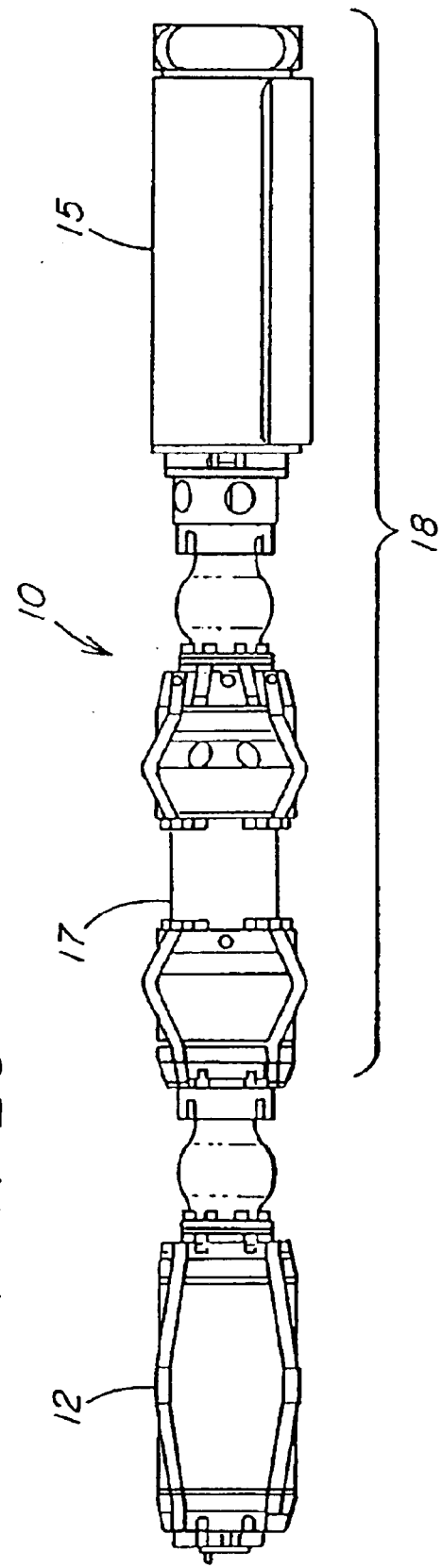

Single Train Task Flow

Module Interchange Task Flow

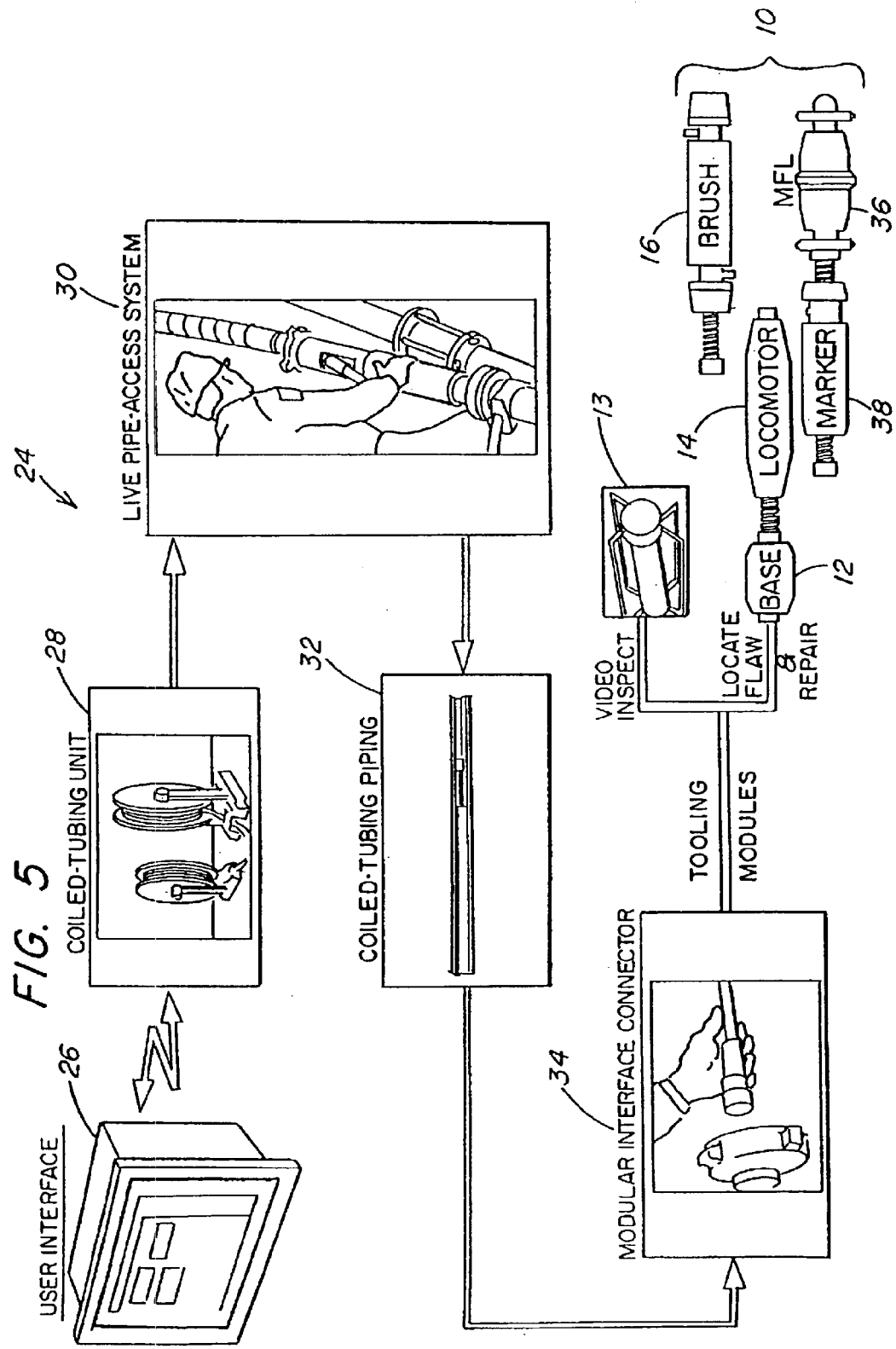

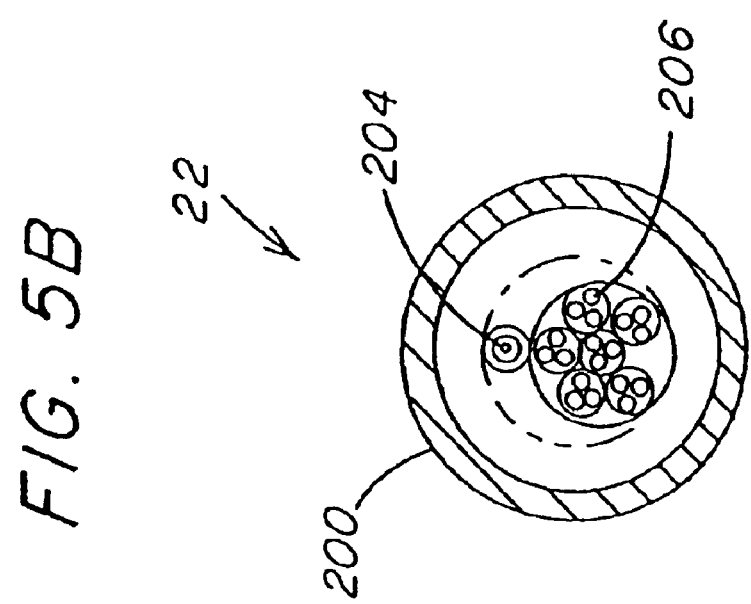
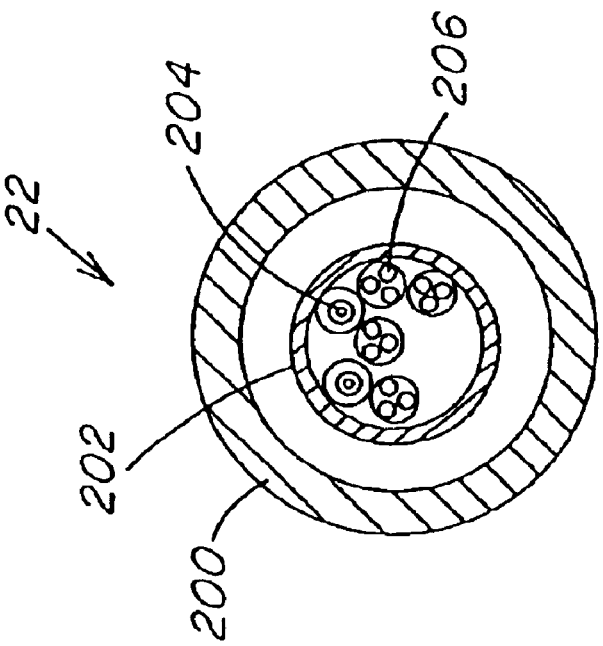

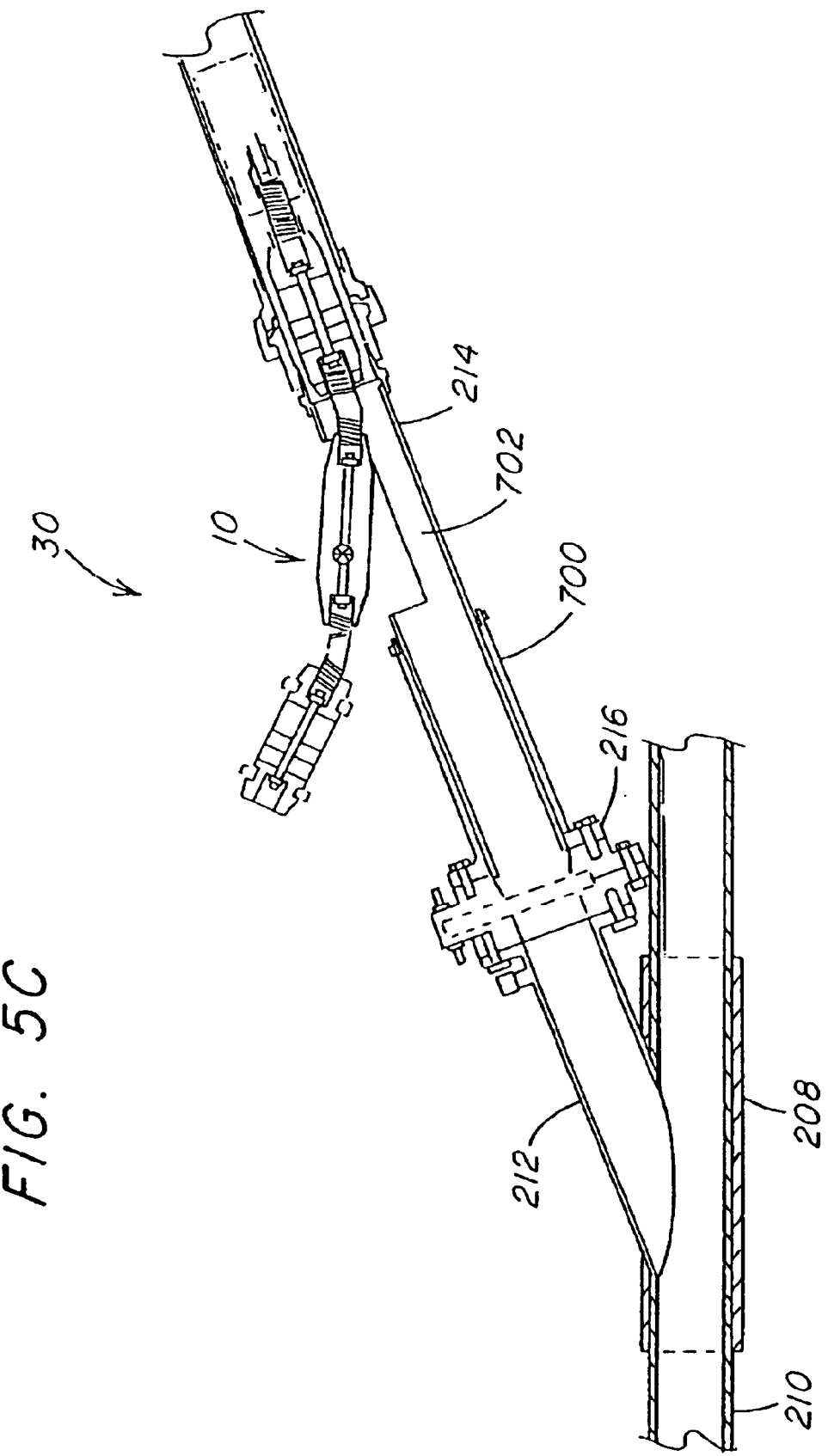

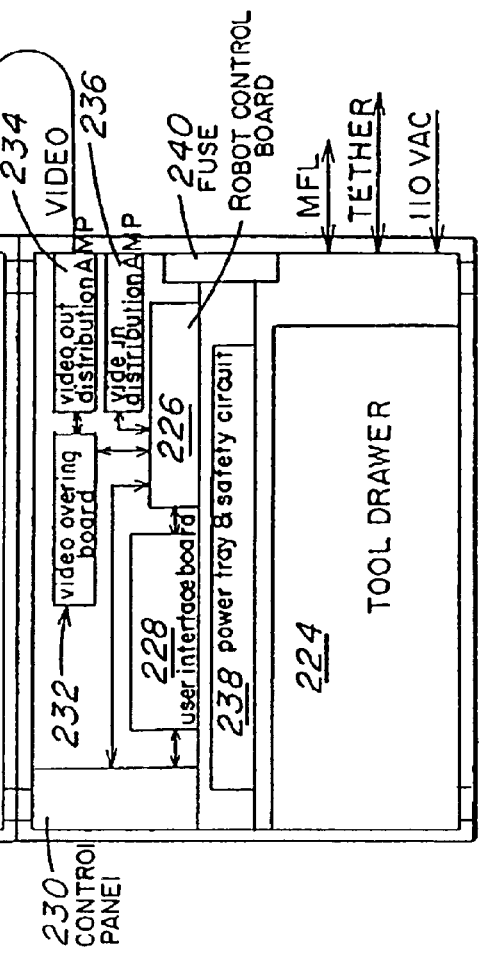
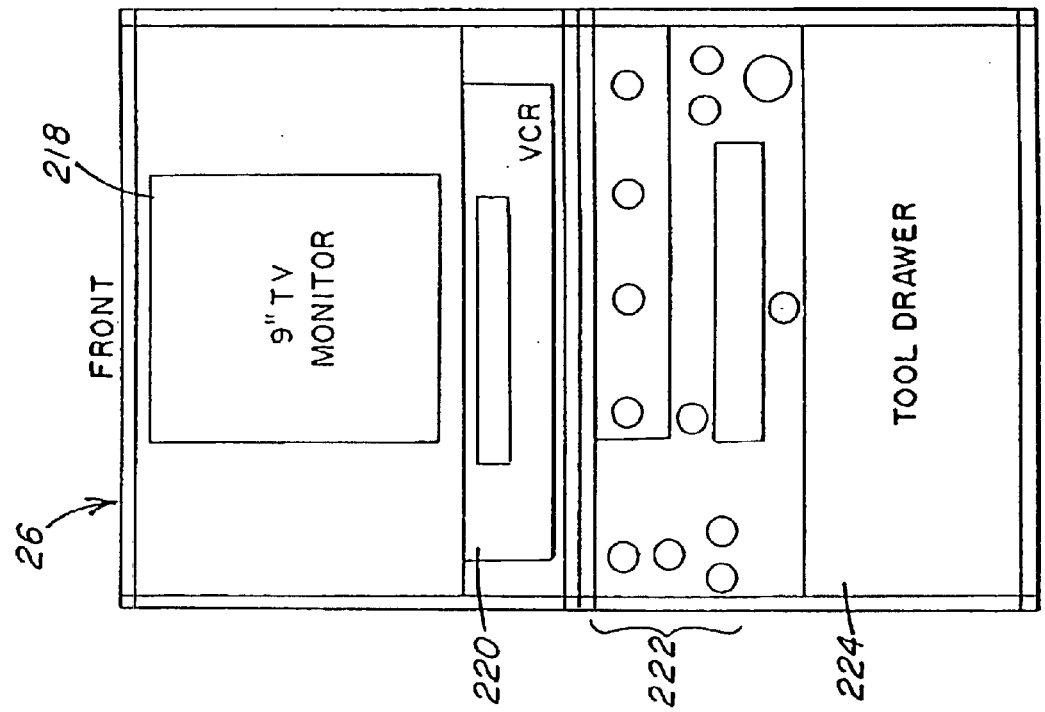

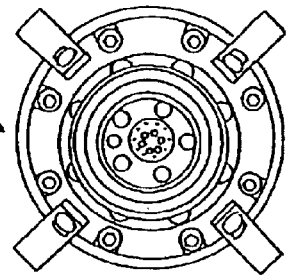
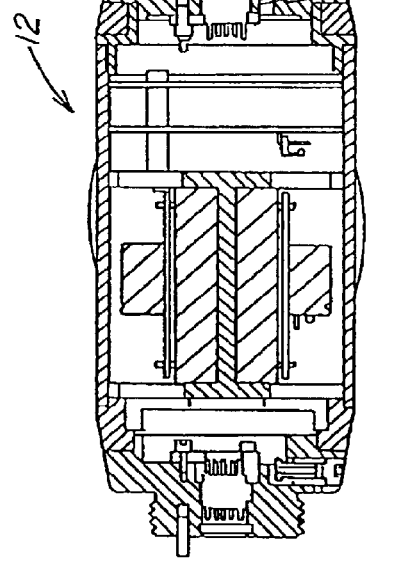
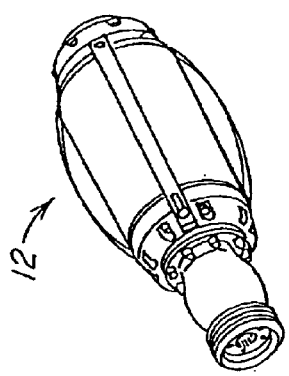
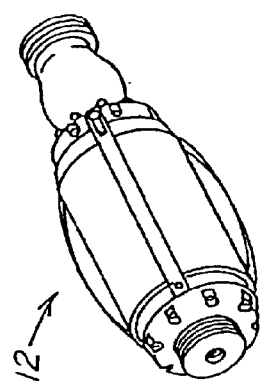
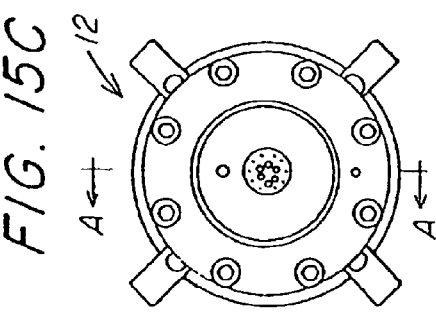

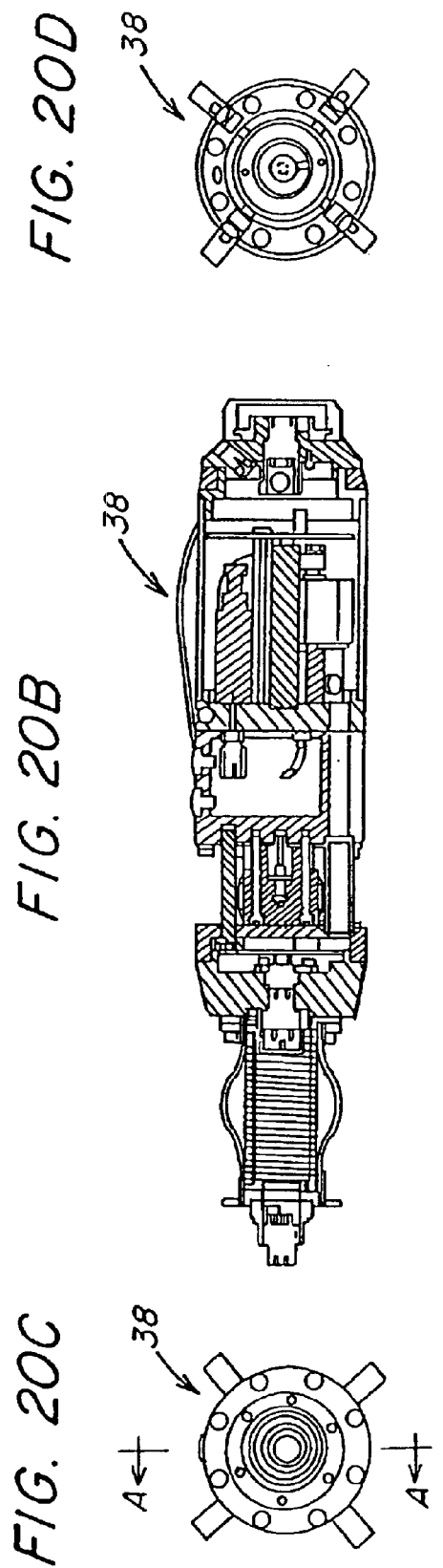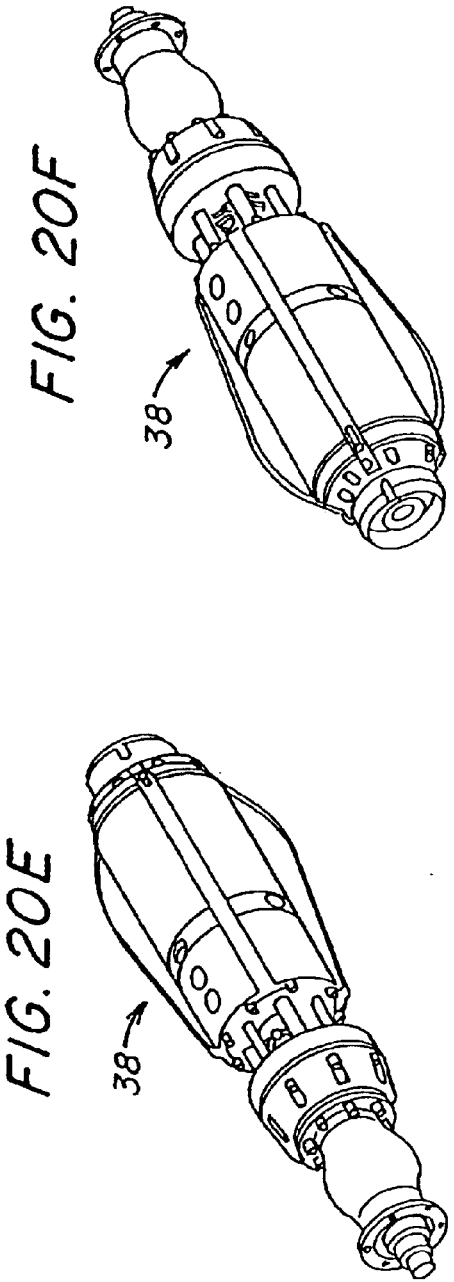
FIG. 20D
FIG. 20B
FIG. 20C
FIG. 20F
FIG. 20E

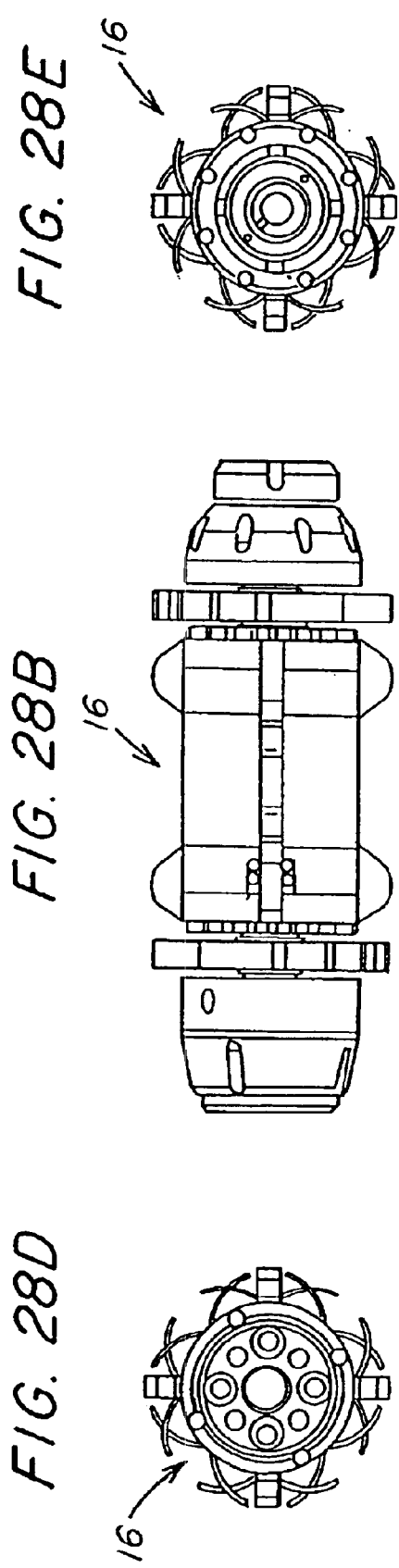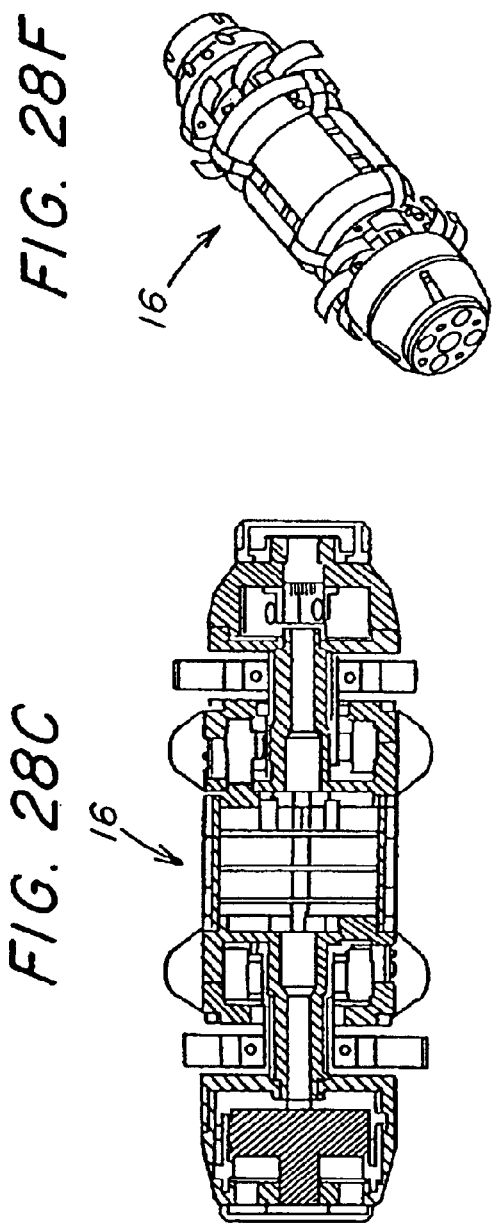
FIG. 28E
FIG. 28B
FIG. 28D
FIG. 28F
FIG. 28C

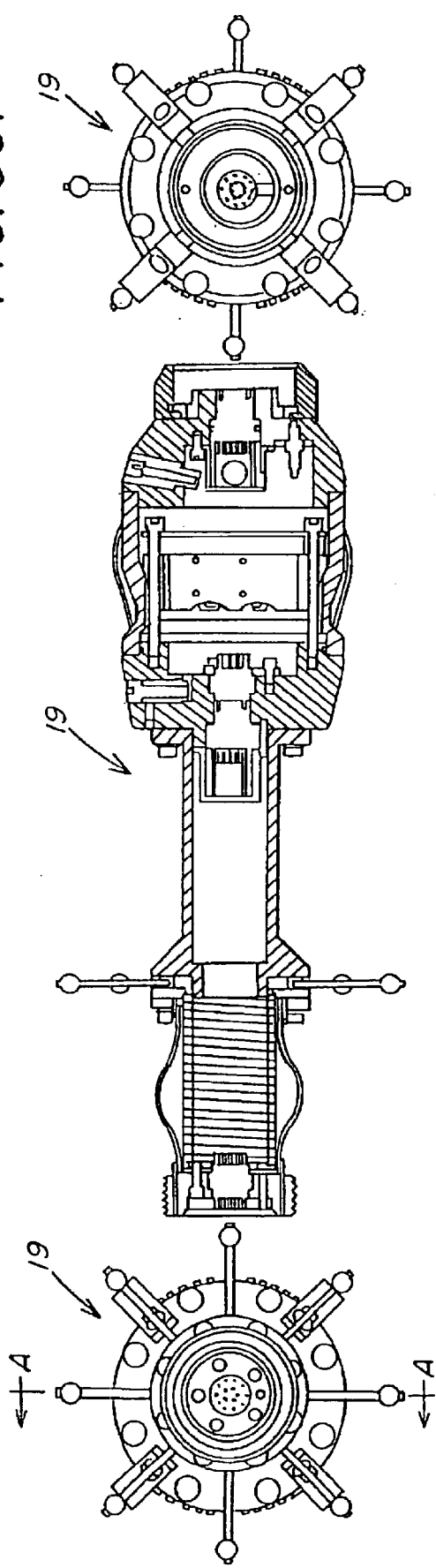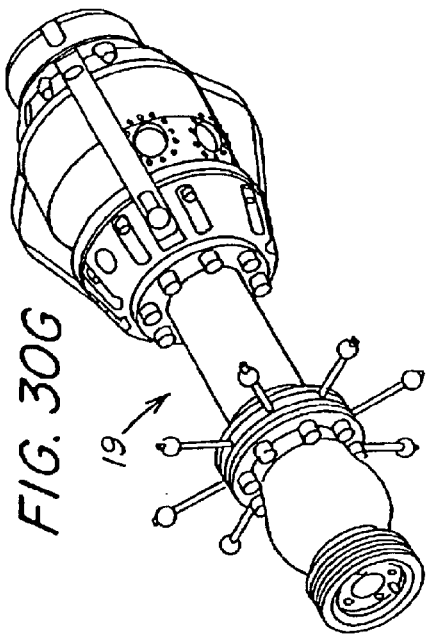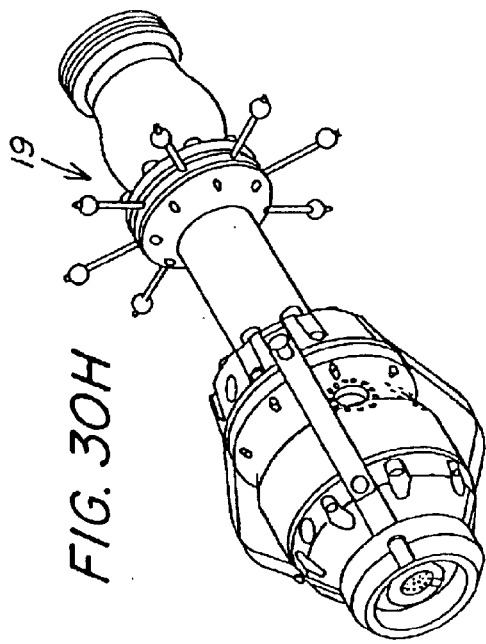

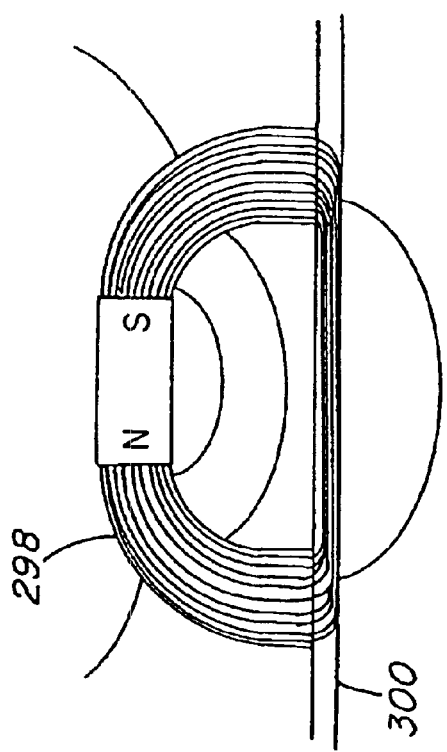
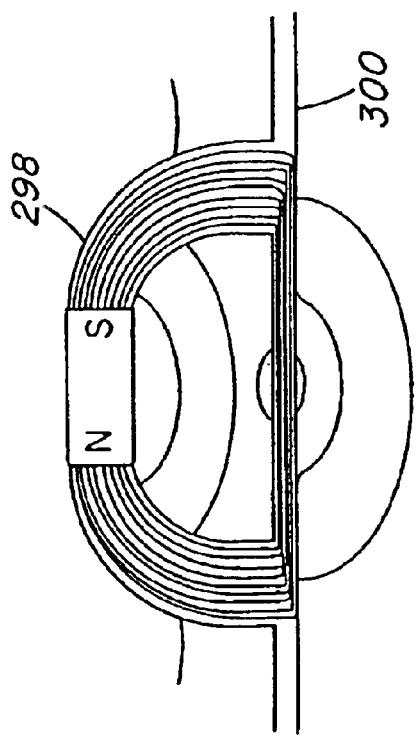

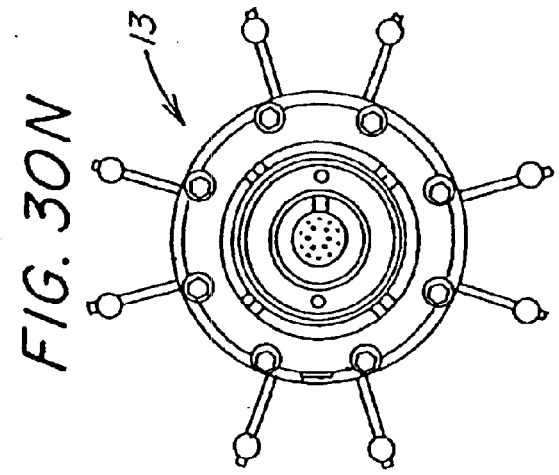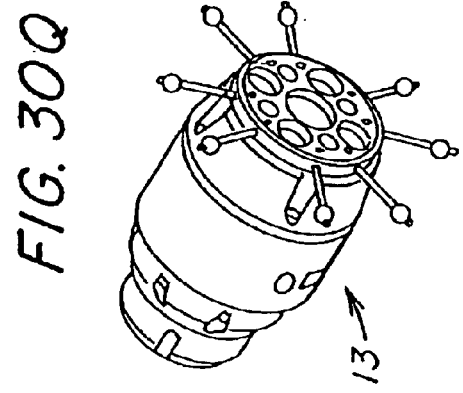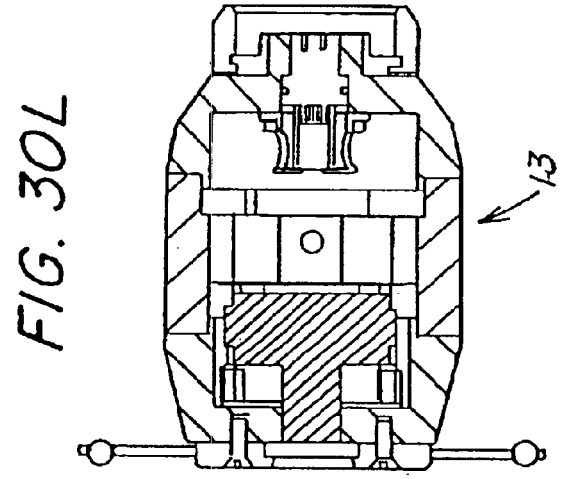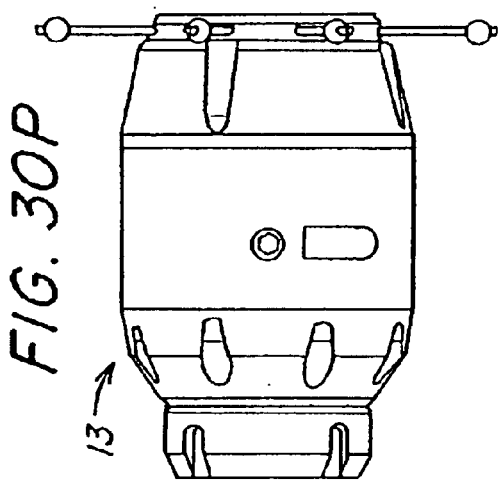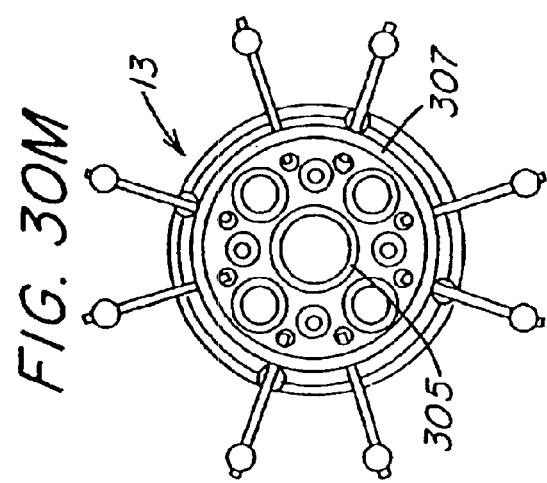

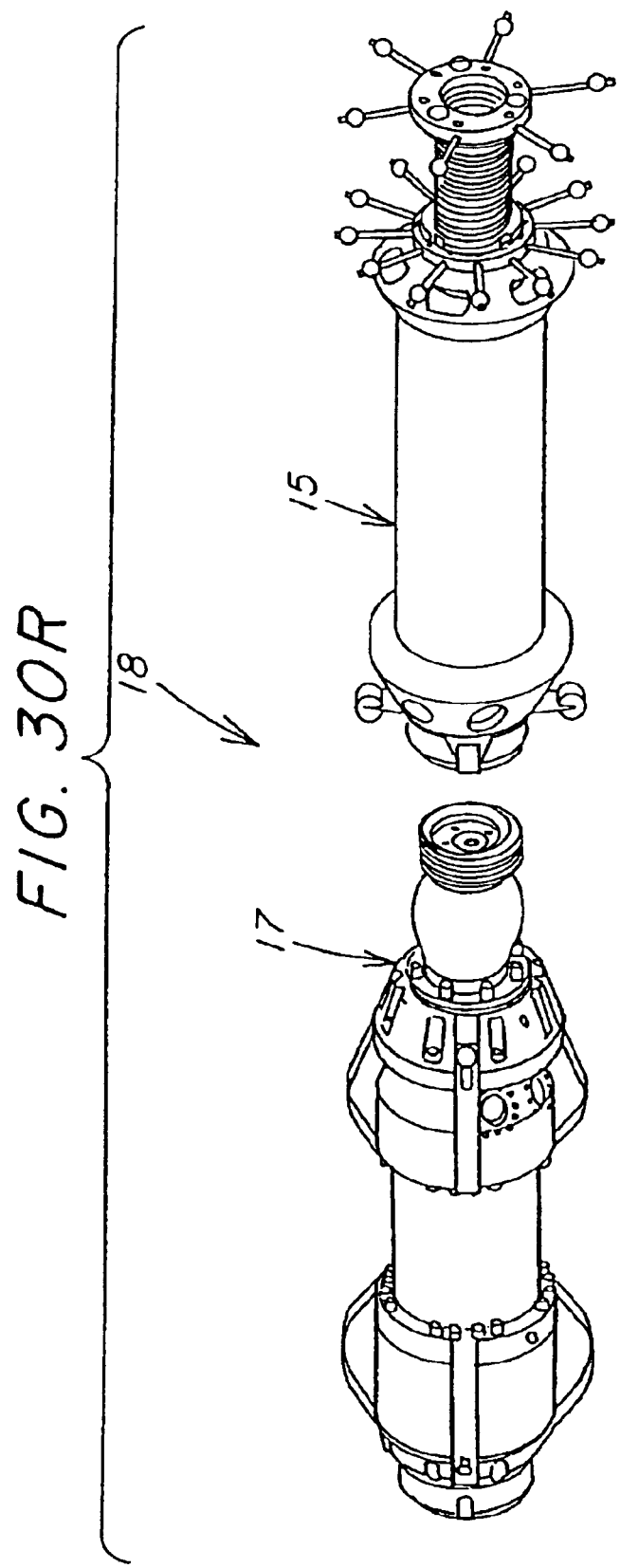

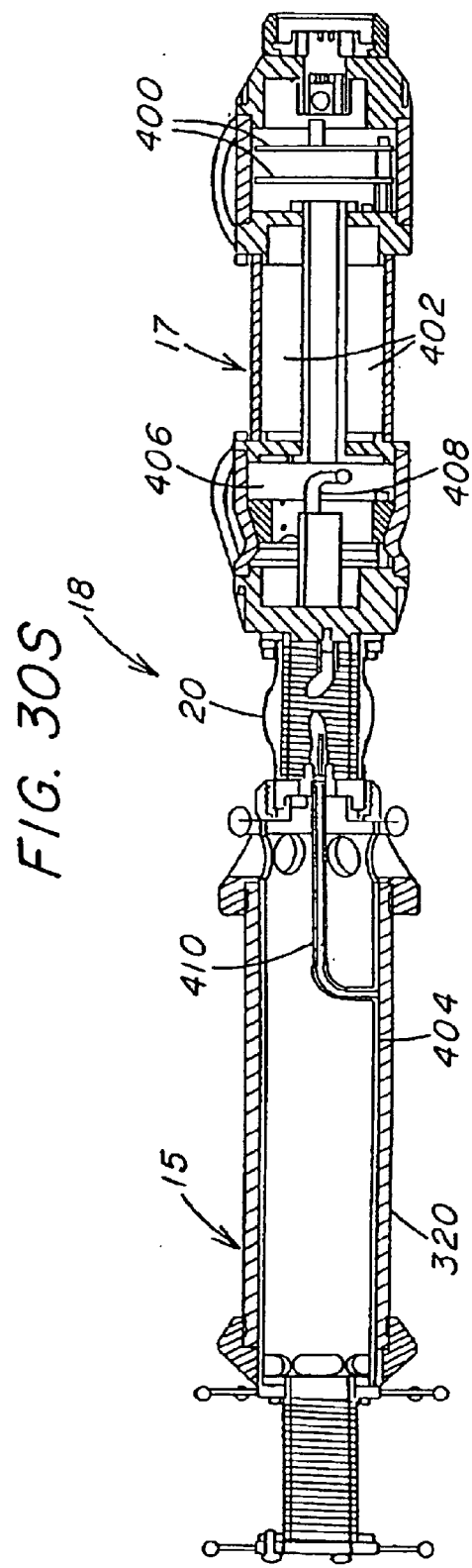
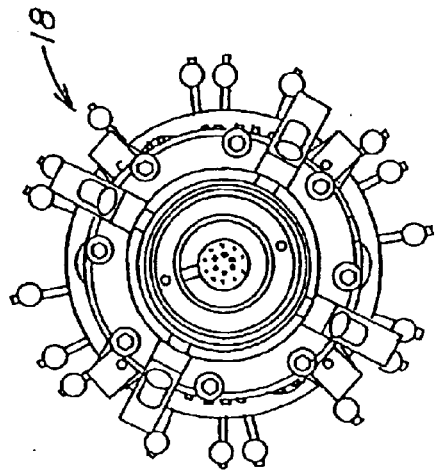
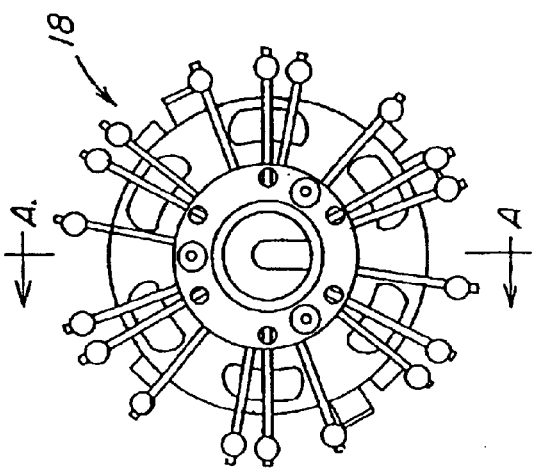
FIG. 30S
FIG. 30U
FIG. 30T

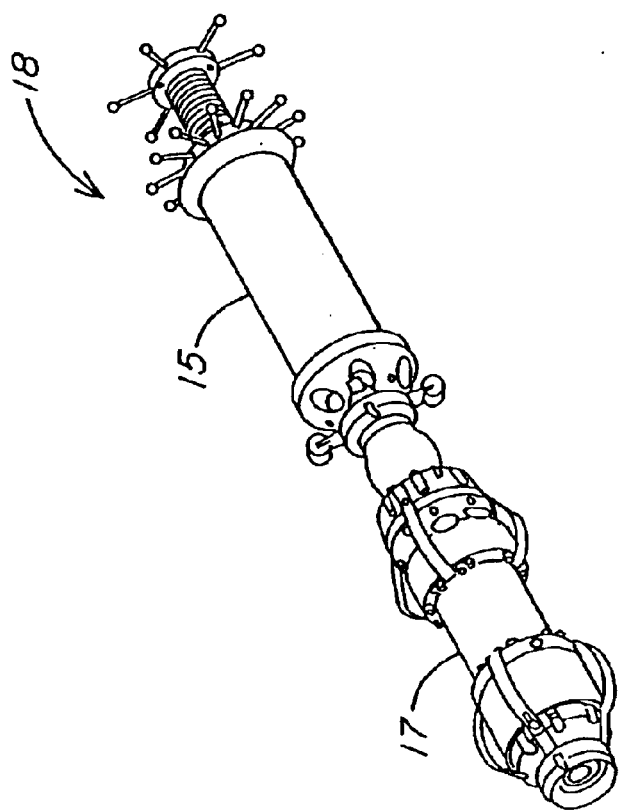
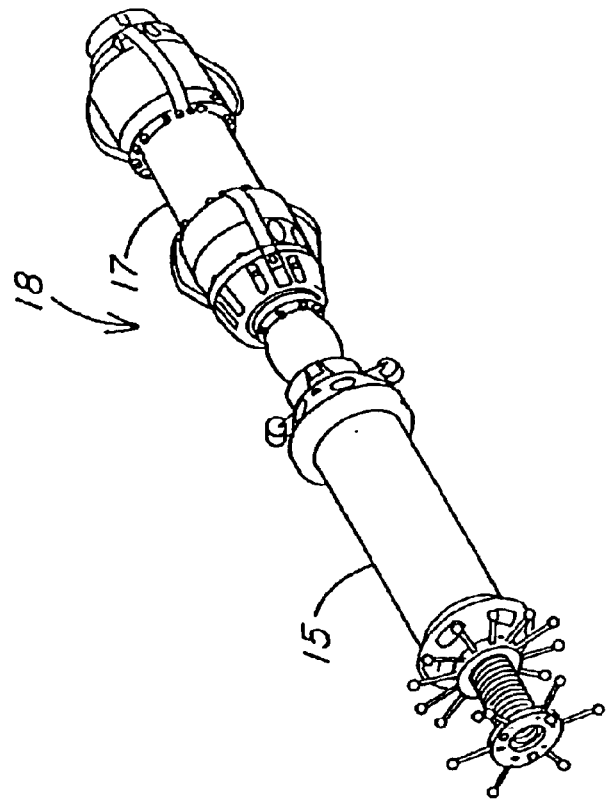

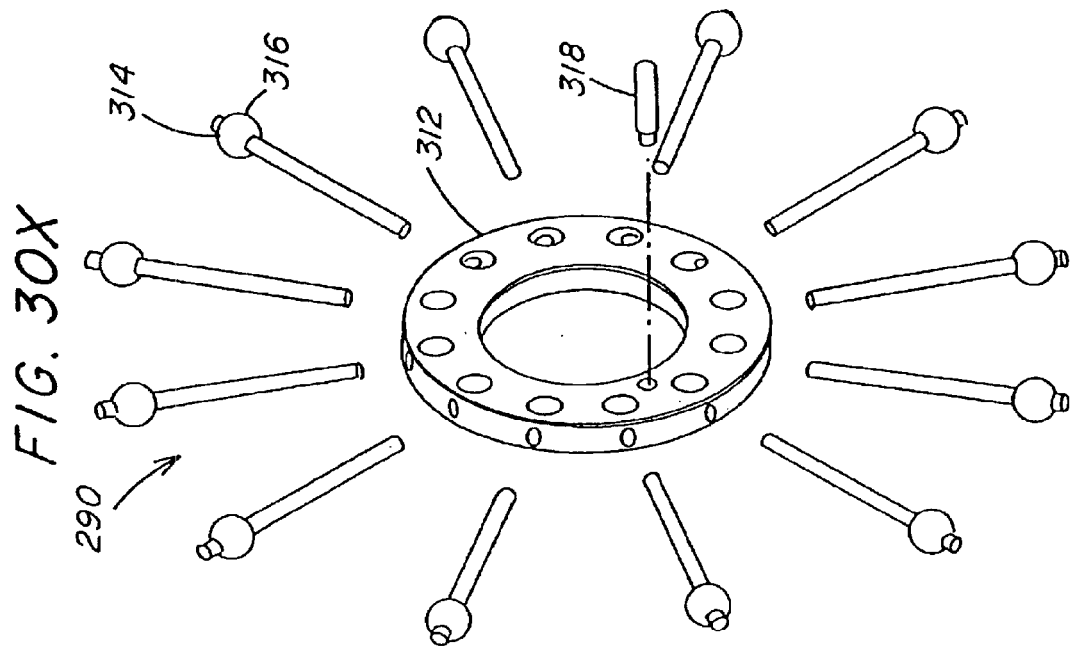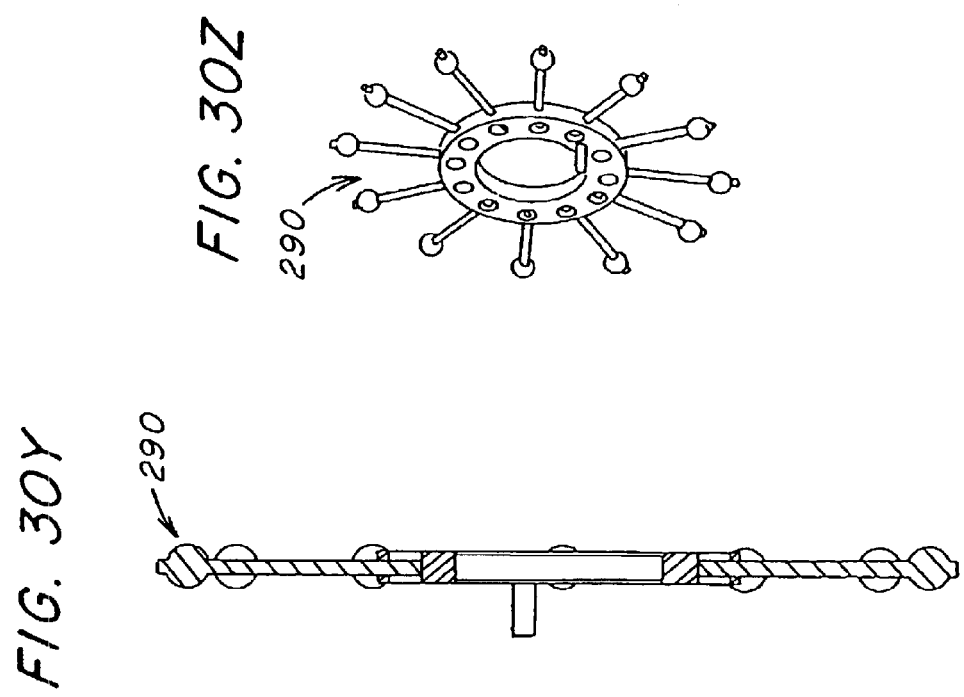

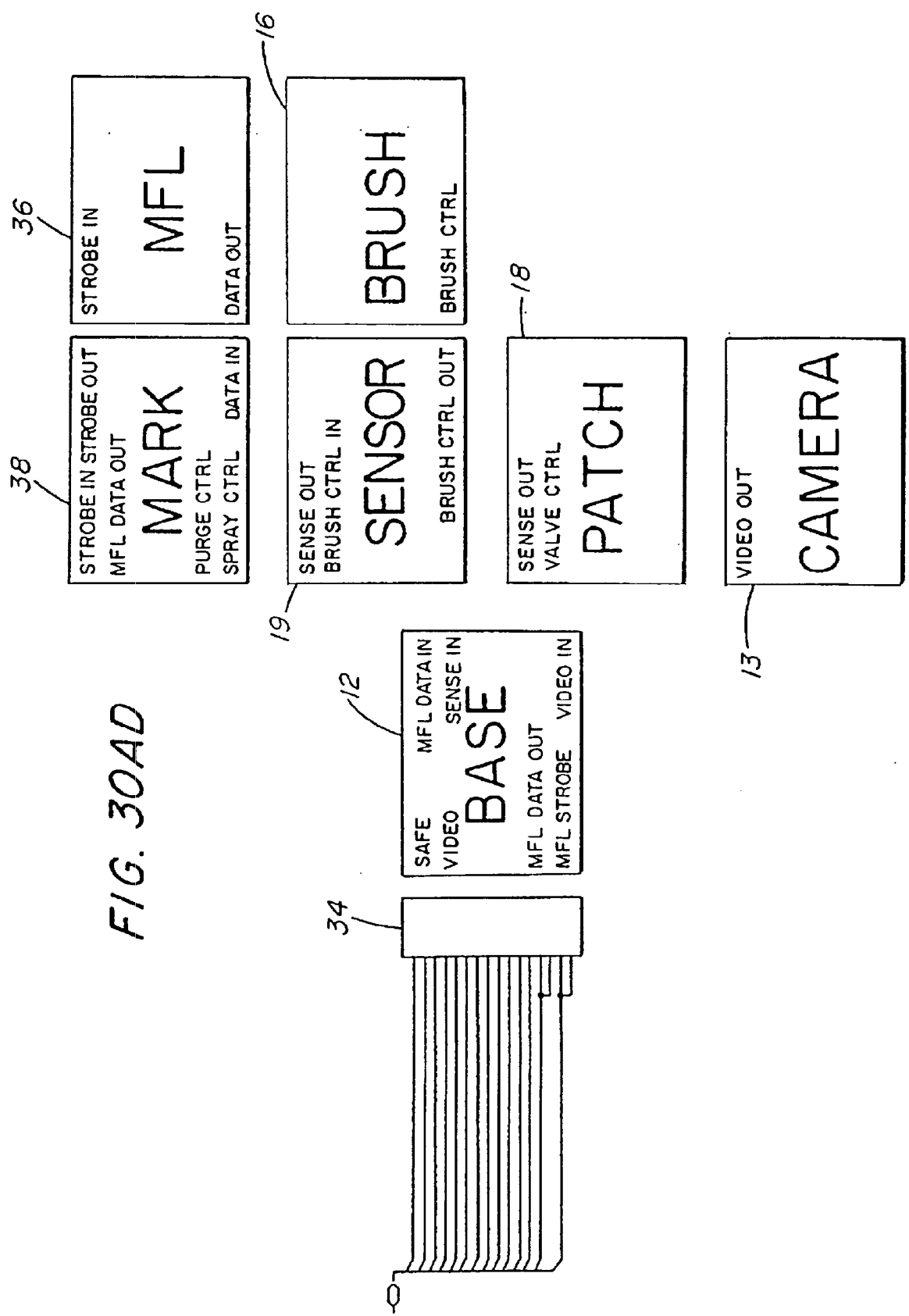

PIPE INSPECTION AND REPAIR SYSTEM

CROSS-REFERENCE TO RELATED APPLICATIONS

This application claims priority under 35 U.S.C. §119(e) to U.S. Provisional Application No. 60/128,821 filed Apr. 12, 1999.

STATEMENT REGARDING FEDERALLY SPONSORED RESEARCH

This invention was made with government support under Grant No NCC5-223 awarded by NASA. The government may have certain rights in the invention.

BACKGROUND OF THE INVENTION

1. Field of the Invention

The present invention is directed generally to a system for pipe inspection and repair and, more particularly, to a modular system for pipe inspection and repair in live-entry environments.

2. Description of the Background

Currently, between 800,000 to 1,000,000 leak repairs are carried out nationwide on gaslines, at a cost of between $750 to $1,250 each, including leak detection and pinpointing, excavation, repair and road restoration. Different external repair techniques and systems exist, but they cannot be deployed into live pipelines to assess the corrosion and sectional loss of pipes with a single excavation. If such a deployment were possible, it would reduce repair costs and provide a preventative maintenance tool.

Devices to access pipes require certain features which are lacking in prior techniques and systems. The need to access live pipes at no more than a 20° entry-angle, as well as the need to travel through bends of 22.5° sweep at 6 times the pipe diameter, impose constraints on the overall and/or individual length of the repair head of the inserted device. A prior camera inspection device, such as the Aries Gascam®, can be used for entry angles approaching 90°, but such devices are only inspection, and not repair devices.

Because of a small, e.g. 4-inch pipe-diameter, and the presence of protruding taps, coupons and sharp edges, the hard diameter of the body of an inspection and repair device must be limited. Also, because such a device operates in a potentially explosive environment, e.g. a methane pipeline, the device needs to be designed to be safe and tolerant to failure modes. The complexity of the repair technology drastically impacts the overall system design in terms of power, interfaces, etc. The need to "prepare" the surface of the pipe for repair is driven by the type of repair technology used, which in turn has an impact on the device. Once repaired, if there is a requirement to test and prove that the repair has been effected, the device design needs to reflect that. One important aspect is the need to detect flaws once they have been located with a sensor system—which must be done simply and reliably. In order to support modularity, tether and connector systems need to be designed so as to allow exchanges of modules in the field without rewiring and software modifications. Also, the operator interface to the device needs to be simple and rugged, because the device will be operated by various field personnel.

There are various prior art systems for patching pipes once a leak is detected and located. For example, external clamps are oftentimes used to repair leaks. However, the site where the leak is located must be excavated in order to attach an external clamp. Various internal repair methods have also been used. Split sleeve spot repair systems, such as Link-Pipe and Snap-Lok, are examples of various internal repair products.

Thus, there is a need for a pipe inspection and repair system that is faster, cheaper and uses a more convenient repair method than is possible with current methods. There is also a need for a system that is able to access and work within live gas mains from a single excavation and allow maximum travel from a single entry-point in both directions and must fit into and pass through, for example, 4 inch I.D. steel gas mains. There is a further need for a system that can reasonably negotiate bends, debris and protruding taps, operate safely within a pure methane environment, identify, mark, acquire, clean and repair defective area(s), and install a certifiable repair system. There is also a need for a system that can guarantee device retrieval under worst-case system failure and be modularly interchangeable with existing and future deployment and sensing/repair components and be easy to operate with minimal and manual operator interactions. There is also a need for a system that is deployable in the same manner as current camera and magnetic flux__ leakage detector (MFL) inspection systems.

SUMMARY OF THE INVENTION

The present invention is directed to a multi-module pipe inspection and repair device. The device includes a base module, a camera module, a sensor module, an MFL module, a brush module, a patch set/test module, and a marker module. Each of the modules may be interconnected to construct one of an inspection device, a preparation device, a marking device, and a repair device. The present invention represents a substantial advance over prior pipe inspection and repair systems. The present invention has the following advantages, among others:

The system uses a multi-module exchangeable work-head system capable of viewing, inspecting, marking, cleaning and repairing pipe leaks or thinning pipe walls.

The multi-module pipe inspection and repair device of the present invention may interface to existing or new coiled-tubing (CT) deployment system sold by, for example, Maurer Engineering, Inc.

The hard module-diameter of the pipe repair device may be made to not exceed 3 inches O.D.

Inert materials (SS) with internal purging and nitrogen pressurization to 100 psig, as well as potting and immersion, are used as safing techniques.

The repair-head has a forward-looking live-video camera monitoring system.

The system has an independent visual flaw-marking emplacement (coupled to an MFL-head) and detection (on repair head) system.

The system is able to fine-position itself using a CT-unit to within +/−1 inch, with an available independent stroke of less than 6 inches. The stroke may be achieved with an independent locomotion unit.

The internal pipe-surface is cleaned mechanically, preferably with a hardened steel brushing or impacting system.

The frontal cleaning-head and repair-modules of the pipe repair device are interchangeable.

The operator hard controls are integrated with existing CT, MFL and camera controls.

The present invention may reduce spot repair costs by as much as 25% for more than 2 repairs from a single excavation.

The present invention may perform 2 to 4 spot repairs per day from a single excavation.

The present invention may pass one or more 22.5° bends, debris, and taps.

The present invention may operate safely in a pure methane environment.

BRIEF DESCRIPTION OF THE DRAWINGS

For the present invention to be clearly understood and readily practiced, the present invention will be described in conjunction with the following figures, wherein:

FIG. 2C is a diagram illustrating another embodiment of the multi-module pipe inspection and repair device;

FIG. 2D is a diagram illustrating a configuration of the multi-module pipe inspection and repair device of FIG. 2C;

FIG. 2E is a diagram illustrating a configuration of the multi-module pipe inspection and repair device of FIG. 2C;

FIG. 2F is a diagram illustrating a configuration of the multi-module pipe inspection and repair device of FIG. 2C;

FIG. 2G is a diagram illustrating a configuration of the multi-module pipe inspection and repair device of FIG. 2C;

FIG. 5 illustrates an iconic diagram of an embodiment of a system in which the device of FIGS. 1 and 2 may be employed;

FIGS. 5A and 5B illustrate cross-section diagrams of embodiments of the coiled tubing inside coiled tubing piping of FIG. 5;

FIG. 5C is a diagram illustrating an embodiment of the live pipe access system of FIG. 5;

FIGS. 5E and 5F are diagrams illustrating front and rear views, respectively, of an embodiment of the user interface of FIG. 5;

FIG. 15B illustrates a cutaway view of the base module of FIG. 15A;

FIGS. 15C and 15D illustrate end views of the base module of FIG. 15A;

FIGS. 15E and 15F illustrate the base module of FIG. 15A;

FIG. 20B illustrates a cutaway view of the marker module of FIG. 20A;

FIGS. 20C and 20D illustrate end views of the marker module of FIG. 20A;

FIGS. 20E and 20F illustrate the marker module of FIG. 20A;

FIG. 28B illustrates a side view of the brush module of FIG. 28A;

FIG. 28C illustrates an exploded view of the brush module of FIG. 28A;

FIGS. 28D and 28E illustrate end views of the brush module of FIG. 28A;

FIG. 28F illustrates the brush module of FIG. 28A;

FIG. 30D is a cutaway view of the sensor module of FIG. 30C;

FIGS. 30E and 30F are end views of the sensor module of FIG. 30C;

FIGS. 30G and 30H illustrate the sensor module of FIG. 30C;

FIGS. 30I and 30J are diagrams illustrating a sensing technique used by the MFL module of the present invention;

FIG. 30L is a cutaway view of the camera module of FIG. 30K;

FIGS. 30M and 30N are end views of the camera module of FIG. 30K;

FIG. 30P is a side view of the camera module of FIG. 30K;

FIG. 30Q is a view of the camera module of FIG. 30K;

FIG. 30R is a diagram illustrating an embodiment of the patch module of the multi-module pipe inspection and repair device of the present invention;

FIG. 30S is a cutaway view of the patch module of FIG. 30R;

FIGS. 30T and 30U are end views of the patch module of FIG. 30R,

FIGS. 30V and 30W are views of the patch module of FIG. 30R;

FIG. 30X illustrates an exploded view of an embodiment of the centralizer of the multi-module pipe inspection and repair device of the present invention;

FIG. 30Y is a cutaway view of the centralizer of FIG. 30X;

FIG. 30Z is a view of the centralizer of FIG. 30X;

FIG. 30AA is a view of the centralizer of FIG. 30X;

FIG. 30AB is a cutaway view of an embodiment of a patch_assembly which may be used with the patch module of FIG. 30R;

FIG. 30AC is a magnified cutaway view of a portion of the patch assembly of FIG. 30AB;

FIG. 30AD is a schematic representing electrical connections of the multi-module pipe inspection and repair device of the present invention;

FIG. 30AE is a block diagram illustrating various electrical components of the multi-module pipe inspection and repair device and the user interface of the present invention;

DETAILED DESCRIPTION OF THE INVENTION

The present invention incorporates a robot-head which is modular in design, thus allowing each module to be individually powered, connected, and controlled and communicated with. The spot-repair patch-technology approach incorporated in the present invention allows repairs to be done in separate stages and thus allows the modules to be designed in succession or in parallel. The robot-head may use a fine-positioning system (also termed a locomotor) or a tether system in order to prepare the surface of the pipe with a mechanical abrasion/brushing system. The inspection system can be, for example, a stand-alone camera, an MFL-head, an eddy-current system, or an integrated board-camera integrated into the preparation and repair-heads.

Figure 1:
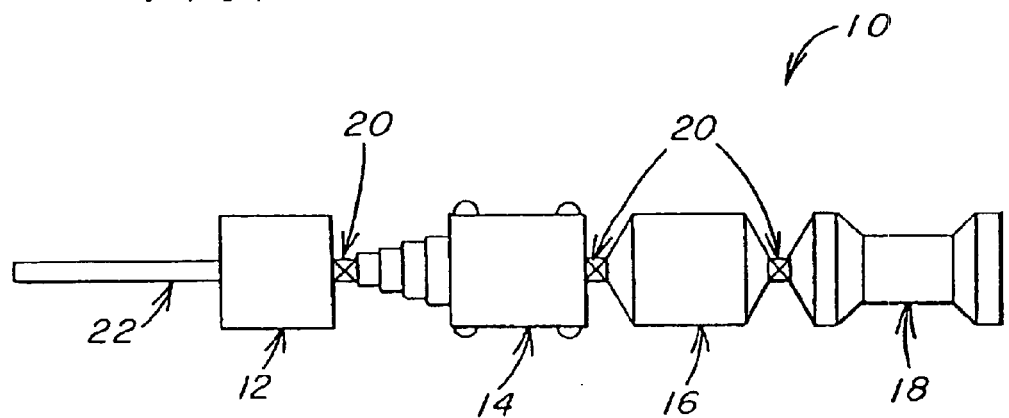
FIG. 1 is a diagram illustrating an embodiment of a multi-module pipe inspection and repair device.

FIG. 1 is a diagram illustrating an embodiment of a multi-module pipe inspection and repair device (robot) 10. The device 10 is configured in a single train arrangement. The device 10 includes a base module 12, a drive (locomotor) module 14, a pipe prep module 16, and a patch set/test module 18. The modules 12, 14, 16, and 18 are connected by flexible joints 20, which may be telescoping and/or flexible. The joints 20 allow the modules 12, 14, 16, and 18 to negotiate bends at the launch point and throughout the pipe. Coiled tubing (with an internal tether) 22 connects to the base module 12 as discussed hereinbelow. The single train concept provides all functions required to perform all of the repair tasks of the device 10 into a single, jointed multi-module device. After pipe flaws have been located, the device 10 is inserted into the pipe and is only withdrawn to load consumables (e.g. patches). No module interchanging is required except for the replacement of a sensor head (not shown) which locates pipe flaws.

Figure 2A:
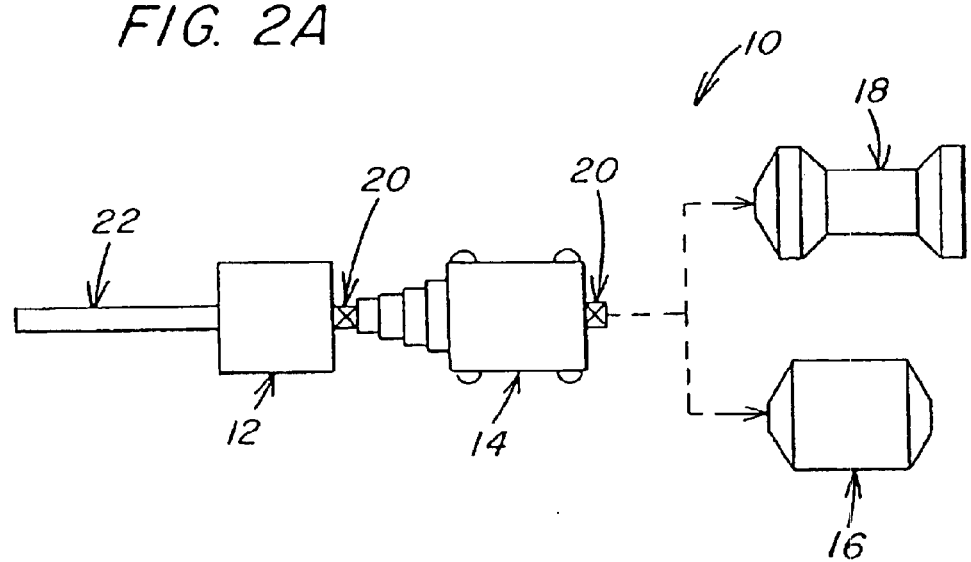
FIG. 2A is a diagram illustrating another embodiment of the multi-module pipe inspection and repair device.

FIG. 2A is a diagram illustrating another embodiment of the multi-module pipe inspection and repair device 10. The device 10 in FIG. 2A is arranged in a module interchange arrangement. The module interchange arrangement differs from the single train arrangement in that the pipe prep module 16 and the patch set/test module 18 are designed to be removed from the locomotor module 14 and interchanged in the field as required by the operational scenario. The primary advantages of the module interchange architecture are that it simplifies the mechanical and electrical design and presents a shorter unit to insert into the pipe. Thus, the amount of extra time spent for the module interchange arrangement can be compared with resulting advantages in complexity and size. In addition, the modularity of the device 10 allows it to be used with sensors already in existence and allows for the addition of other tooling and/or inspection technologies and systems, both those presently available and those contemplated in the future.

Figure 2B:
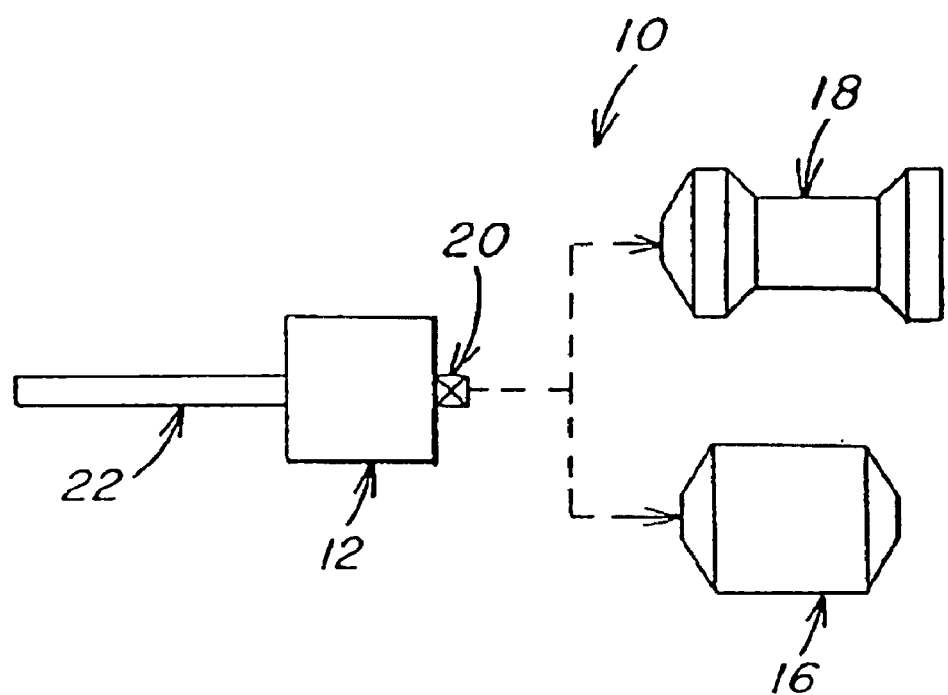
FIG. 2B is a diagram illustrating another embodiment of the multi-module pipe inspection and repair device.

FIG. 2B is a diagram illustrating another embodiment of the multi-module pipe inspection and repair device 10. As in FIG. 2A, the device 10 is arranged in a module interchange arrangement. However, the device 10 in FIG. 2B does not have a locomotor module 14. Instead of a locomotor module, the device 10 of FIG. 2B is positioned within the pipe using the coiled tubing 22. Such an arrangement would require fine positioning changes by the system 24 operator rather than the locomotor module 14.

As described hereinbelow, the device 10 makes use of existing technologies in two areas: locomotion through the pipe via a "coiled tube drive" and detection of flaws using, for example, magnetic flux leakage (MFL), ultrasonic, eddy-current, or x-ray detector. These systems have been used together successfully in prior systems in the field to map flaws in working gas pipelines.

FIG. 2C is a diagram illustrating another embodiment of the multi-module pipe inspection and repair device 10. As illustrated in FIG. 2C, the base 12 may be connected to a number of modules. For example, a camera module 13 can be used to visually inspect the interior of a pipe. Also, an MFL module 36 and a marker module 38 can be used to detect and mark flaws for later repair. Although the module 36 is described herein as an MFL module, the module 36 may use any suitable sensing technique such as, for example, eddy-current or acoustic sensing. A sensor module 19 can then be used with the brush module 16 to prepare the surface of the pipe for repair. The patch set/test module 18, which may include a bladder module 15 and a supply module 17, can then be used to repair the flaw. The bladder module 15 sets the patch via pneumatic expansion with a locking sleeve covered with felt and epoxy to bond the patch to the pipe.

FIG. 2D is a diagram illustrating a configuration of the multi-module pipe inspection and repair device 10 of FIG. 2C with the camera module 13 assembled to the base module 12. FIG. 2E is a diagram illustrating a configuration of the multi-module pipe inspection and repair device 10 of FIG. 2C with the MFL module 36 and the marker module 38 assembled to the base module 12. FIG. 2F is a diagram illustrating a configuration of the multi-module pipe inspection and repair device 10 of FIG. 2C with the sensor module 19 and the brush module 16 assembled to the base module 12. FIG. 2G is a diagram illustrating a configuration of the multi-module pipe inspection and repair device 10 of FIG. 2C with the patch test/set module 18 assembled to the base module 12.

In order to understand the impact of the single train and module interchange arrangements of FIGS. 1 and 2A through 2G, the impact on the overall time required to prep and seal a certain number of flaws, spaced evenly over a given length of pipe, with both arrangements, is set forth hereinbelow in conjunction with FIGS. 3 and 4. The single train and module interchange arrangements are first broken down into key subtasks.

Figure 3:
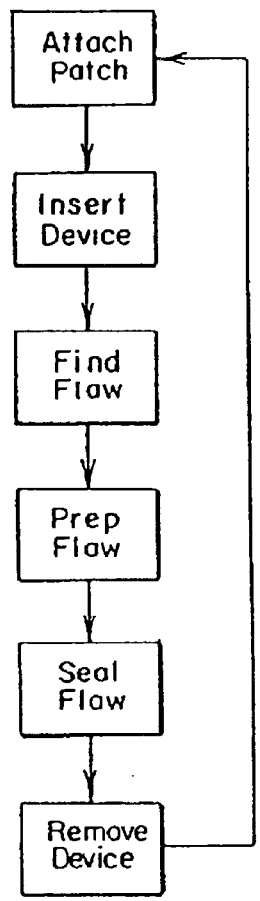
FIGS. 3 and 4 illustrate flows of subtasks through an operational process using the device of FIGS. 1 and 2, respectively.
Figure 4:
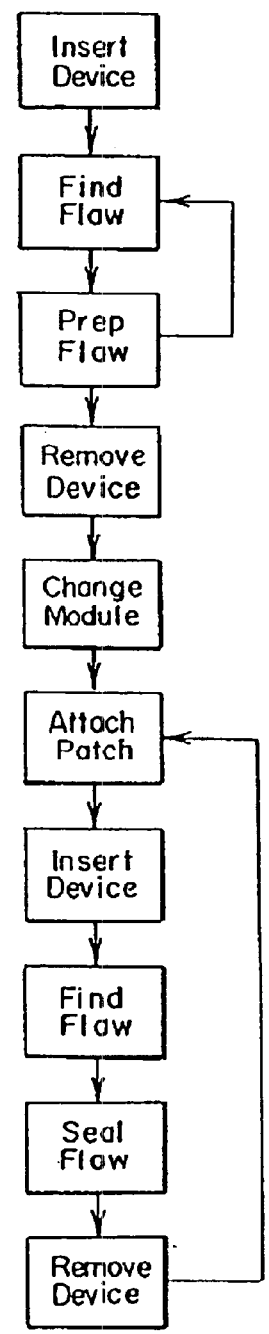

FIGS. 3 and 4 illustrate flows of subtasks through an operational process using the device 10 of FIGS. 1 and 2, respectively. The single train arrangement is conceptually simpler, because each pipe flaw is fixed in one macrostep. In the module interchange arrangement, however, all of the pipe flaws may be prepared at once, so only one module change must be performed. After all of the pipe flaws are prepared and the module change is performed, the flaws are patched one after the other.

As the number of flaws increases, the time per flaw is constant for the single train arrangement and decreases slightly for the module interchange arrangement, and the total time for each increases nearly linearly with the number of flaws. As the number tends to infinity, the two arrangements converge to the same time per flaw and total time. The length of pipe run is bounded by the deployment mechanism, so no variance is induced. As the rate of coiled-tubing 22 deployment increases, the total time for each decreases slightly. Because the transit time is relatively small in each case, the rate of deployment does not have a significant effect on the estimated timing. The time required to insert/remove the device 10 does not affect the overall timing, because both schemes require the same number of insertion/removal actions. The time required for injecting, curing, and testing the sealant contributes significantly, though equally, in both arrangements. Preliminary estimates show that up to one-fifth of the overall repair time may be spent in these three steps. Decreasing or eliminating the time spent doing nothing but waiting for the sealant to cure, therefore, would drastically reduce the overall repair time.

FIG. 5 illustrates an iconic diagram of an embodiment of a system 24 in which the device 10 of FIGS. 1 and 2 may be employed. The system 24 includes a user interface 26, a hydraulically-powered coiled-tubing deployment system 28, and a live-pipe access system 30. Coiled tubing piping 32 contains a tether. Adaptations to the access system 30 can be made to accommodate a somewhat lengthened module train to be deployed. At the end of a composite push-rod, which is coupled to the stainless-steel tubing 22, a standardized connector 34 with strain-relief allows the electro-mechanical connection of the base module 12 to the coiled tubing 22. All modules attached to the device 10 are henceforth attached to the base module 12. The tether architecture (conductor-type, -count, -gauge, etc.) supports the attachment of existing, planned, and future modules. The tooling modules can consist of, for example, the camera module 13, the MFL module 36, the patch set/test module 18, the locomotor module 14, etc. The camera module 13 attaches to the base module 12 and provides live video footage to the operator of the state of the line to be inspected (and possibly repaired) via the user interface 26. Upon conclusion of the visual inspection, the camera is removed and replaced by a combined MFL module 36 and marker module 38. The MFL module 36 is deployed and upon extraction, all sections/spots of pipe deemed substandard are marked with a visible, infrared, chemical, magnetic, or ultraviolet marker such as, for example, visible paint-spots using the marker module 38.

Once retrieved and after the operator has decided which spots to repair, a repair head is installed, consisting of the locomotor module 14 (optionally) and the pipe prep module 16, which can be a brush module. The pipe prep module 16 brushes, for example, a 12-inch patch at each marked spot, after which it is retracted and replaced with the patch set/test module 18, which can be a spot-repair emplacement module. Starting, for example, from the farthest repair-location, all unacceptable spots are repaired, the system is fully retrieved and dismantled, the access-system is sealed off, the hole is filled in and the surface (roadway, sidewalk, etc.) is restored. The entire operation is performed from a single typical excavation and can allow access to, for example, 1,000 feet of gasline on either side of the excavation.

FIGS. 5A and 5B illustrate cross-section diagrams of embodiments of the coiled tubing 22 inside the coiled tubing piping 32 of FIG. 5. In FIG. 5A, a steel wall 200 provides the exterior of the tubing 22. A jacket 202 constructed of, for example, polyvinylchloride (PVC), provides flexible and insulative protection for the conductors contained within the tubing 22. Coaxial cable 204 and bundled and shielded wire 206 are the conductors within the tubing 22. In FIG. 5B, the coaxial cable 204 is not bundled with the wire 206.

FIG. 5C is a diagram illustrating an embodiment of the live pipe access system 30 of FIG. 5. A sleeve 208 of the system 30 is attached to a section of pipe 210 by, for example, clamping or welding and an access hole is made in the pipe 210. The access hole can be, for example, sized the same as the diameter of the pipe 210. The sleeve 208 includes a protruding portion 212. The angle formed between the portion 212 and the pipe 210 can be any suitable angle for the dimensions of the device 10 such as, for example 20°. An access tube 214 of the system 30 is attached to the protruding portion 212. A valve assembly 216 seals off the portion 212 (and hence the pipe 210) prior to and after insertion of the device 10 into the pipe 208. The valve assembly 216 may be, for example, a ball valve or a gate valve. The assembly 216 or the portion 212 may contain a pressurized grease slip fitting (not shown) to seal the portion 212 during and after insertion of the device 10 into the pipe 208. A closure 700 covers void 702 after the device 10 has been inserted into the tube 214.

Figure 5D:
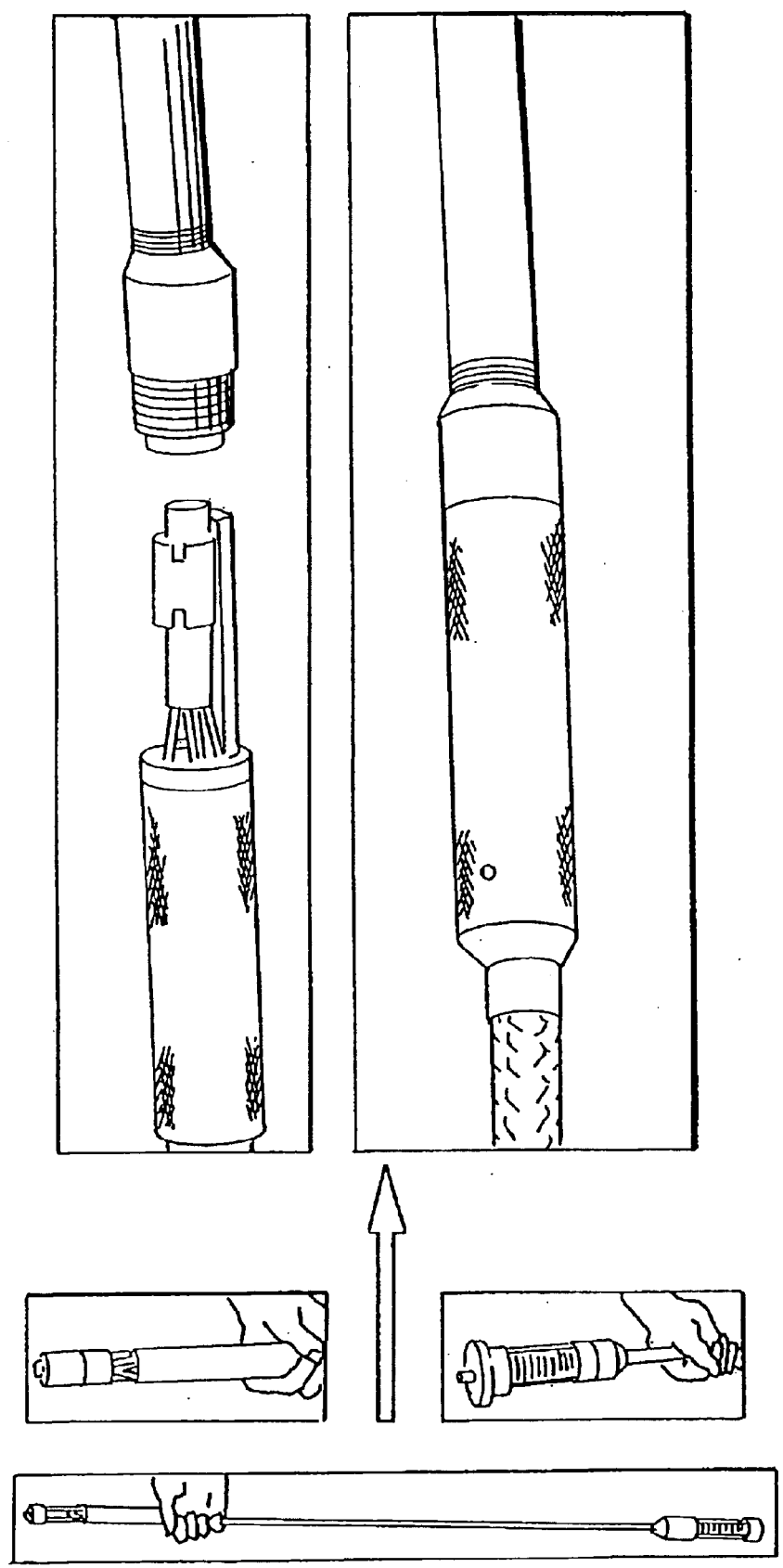
FIG. 5D are diagrams illustrating embodiments of the standardized connectors of FIG. 5.

FIG. 5D are diagrams illustrating embodiments of the standardized connectors 34 of FIG. 5.

FIGS. 5E and 5F are diagrams illustrating front and rear views, respectively, of an embodiment of the user interface 26 of FIG. 5. A television monitor 218 and a video cassette recorder 220 provide a visual interface and means to record visual images from the camera module 13. Various indicator lights and controls 222 provide status information and allow for control of the various components of the system 24 and a tool drawer 224 allows for storage of any tools that may be necessary in the servicing of the system 24.

As can be seen from FIG. 5F, various circuit boards comprise the electrical portions of the interface 26. A robot controller board 226 controls the device 10 and a user interface board 228 controls a control panel 230, which is connected to the lights and controls 222. A video overlay board 232, a video out distribution amplifier 234, and a video in distribution amplifier 236 control the video functions of the interface 26. A power tray and safety circuit 238 provides power distribution to the electrical components of the interface 26. The electrical components of the interface 26 are protected by a fuse 240.

Figure 5G:
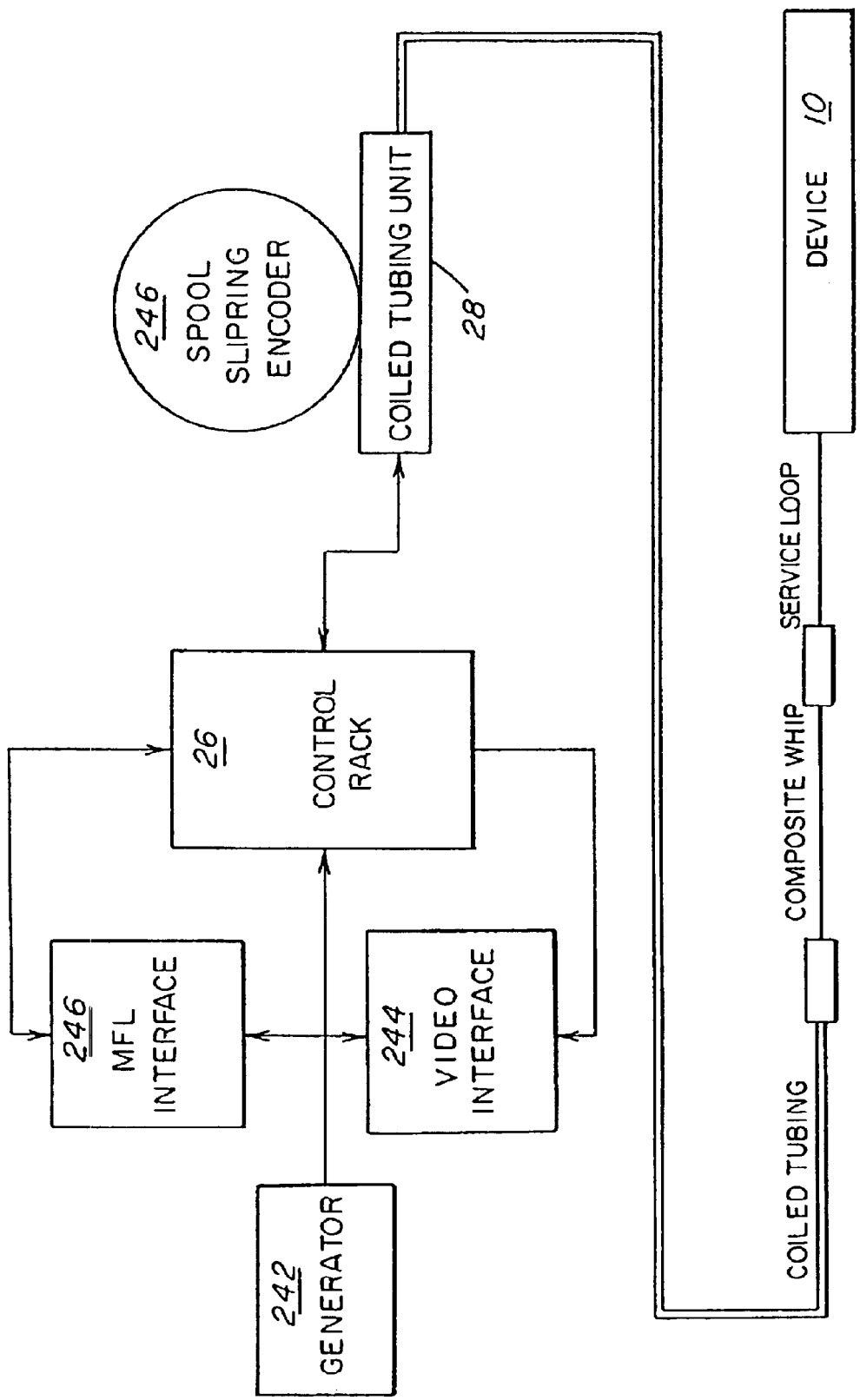
FIG. 5G is a logical block diagram of the system of FIG. 5.

FIG. 5G is a logical block diagram of the system of FIG. 5. A generator 242 provides the power for the system operation in the field. A video interface 244 and an MFL interface 246 provide interfaces for the camera module 13 and the MFL module 36, respectively. A slipring 246 encoder is located on the coiled tubing unit 28 so that the amount of tubing which has been dispensed from the unit 28 may be tracked and reported to the interface 26.

Figure 6:
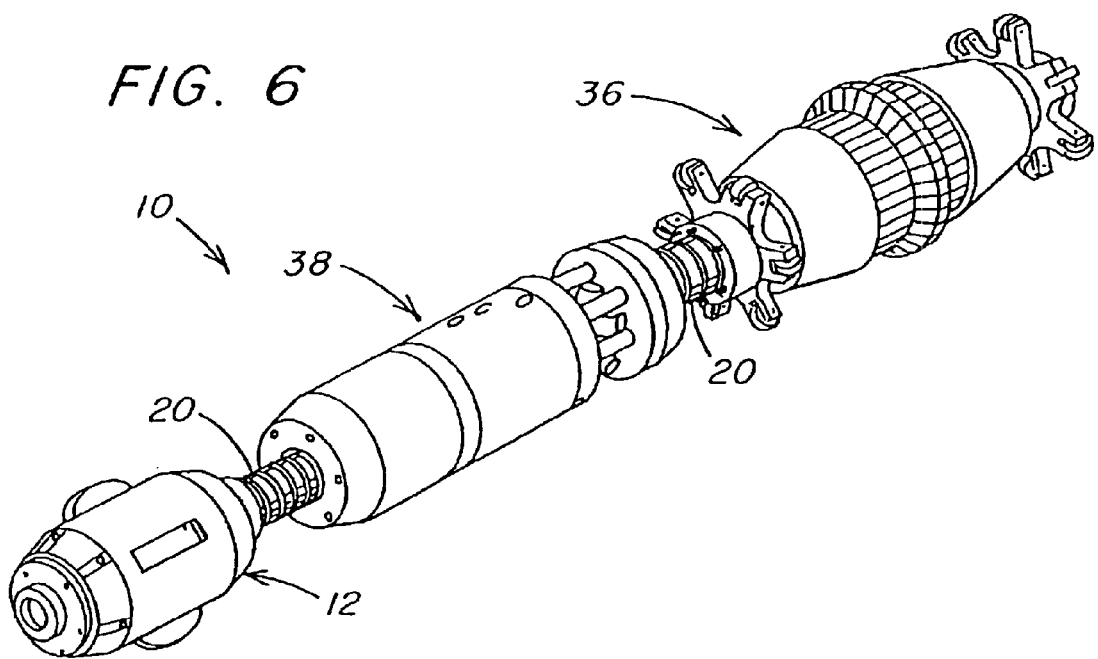
FIG. 6 is a diagram illustrating the multi-module pipe inspection and repair device configured as an inspection and marking assembly.
Figure 7:
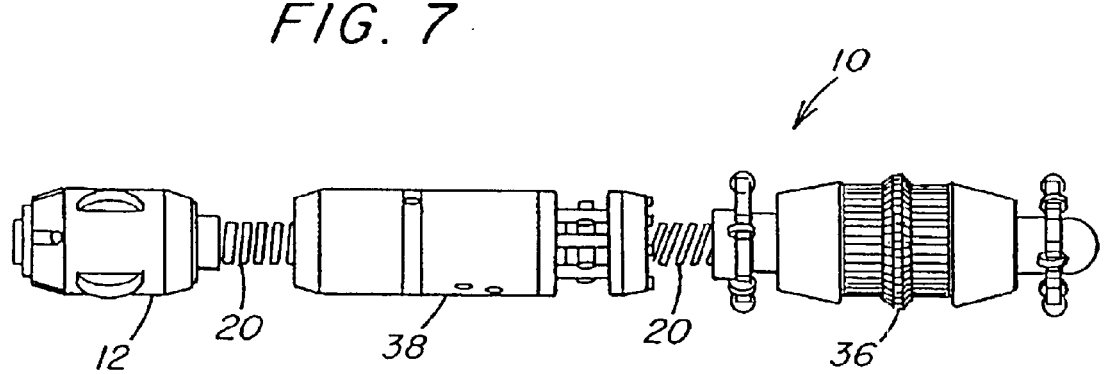
FIGS. 7 and 8 illustrate a side view and an end view, respectively, of the multi-module pipe inspection and repair device of FIG. 6.
Figure 8:
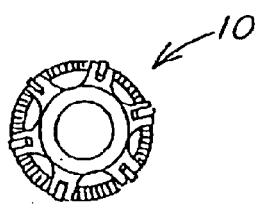

FIG. 6 is a diagram illustrating the device 10 configured as an inspection and marking assembly. FIGS. 7 and 8 illustrate a side view and an end view, respectively, of the device 10 of FIG. 6. The device 10, when configured as an inspection assembly, locates flaws in the pipe using the MFL module 36 and applies a marker at a controlled offset near each flaw using the marker module 38.

Figure 9:
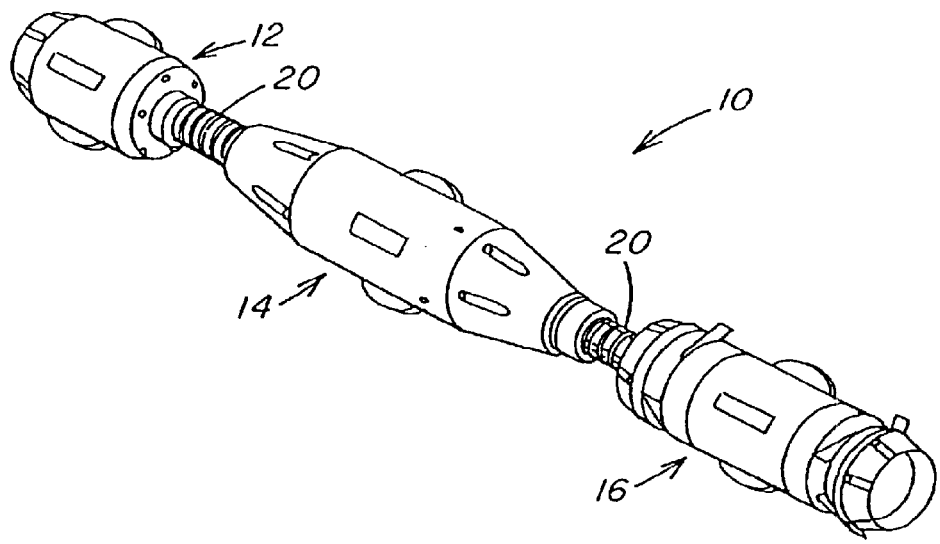
FIG. 9 is a diagram illustrating an embodiment of the multi-module pipe inspection and repair device configured as a preparation assembly.
Figure 10:
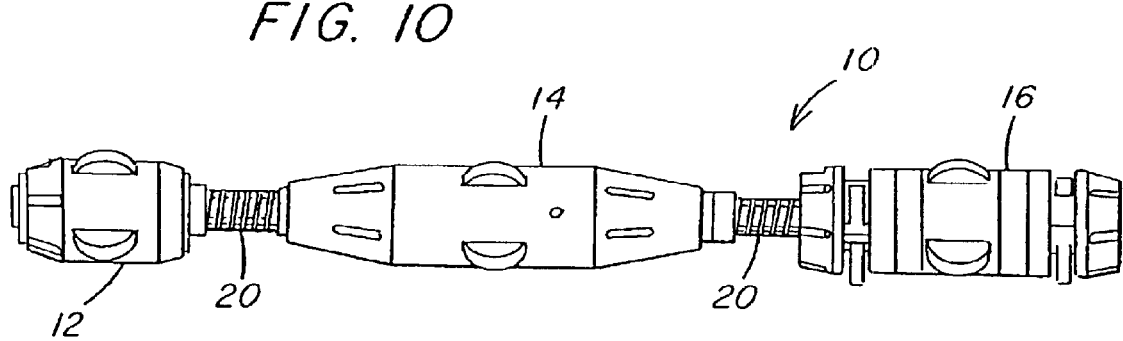
FIGS. 10 and 11 illustrate a side view and an end view, respectively, of the device of FIG. 9.
Figure 11:
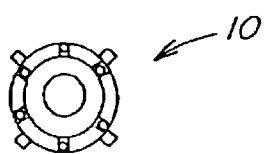

FIG. 9 is a diagram illustrating an embodiment of the device 10 configured as a preparation assembly. FIGS. 10 and 11 illustrate a side view and an end view, respectively, of the device 10 of FIG. 9. The device 10, when configured as a preparation assembly, cleans the pipe surface at the location of each flaw for the application of a patch. The preparation assembly consists of the base module 12, the locomotor module 14 (optionally), and the pipe prep module 16 which is represented as a brush module. Sensors in the locomotor module 14 detect the marker to indicate that a flaw has been located. Alternatively, the camera module 13 may be substituted for the locomotor module 14. The camera module 13 would allow an operator of the system 24 to view the marker via the user interface 26. The purpose of the locomotor module 14 is to provide sufficient travel of the brush module 16 to clean, for example, a 12-inch long section of pipe without requiring the operator of the coiled tube to advance or retract the device 10. If the locomotor module 14 is not present, the system 24 operator and the coiled tubing 22 provide the indexing of the device 10.

The device 10 configured as a patch assembly (not shown) replaces the brush module 16 with a patch set/test module 18. One patch at a time is loaded onto the patch set/test module 18 so the device 10 has to be withdrawn, reloaded and reinserted into the pipe once for each flaw. Alternatively, more than one patch can be loaded onto the patch set/test module 18 or more than one patch set/test module 18 may be attached to the device 10.

The following is a description of an example of an operational scenario for the system 24. Excavation and launch point preparation are conducted prior to the introduction of the device 10 into the pipe.

Pipe Inspection

1. Insert device 10 configured as an inspection assembly into the pipe.
2. Advance the coiled tube drive 28 +1000 Ft. to locate flaws (rough location).
3. Retract the coiled tube drive 28 to accurately locate the farthest flaw.
4. Mark the location.
5. Repeat steps 3 & 4 for all remaining flaws.
6. Remove the device 10 from the pipe.

Pipe Preparation

7. Remove the MFL module 36 from the base module 12.
8. Attach the locomotor module 14 (optional) and the sensor module 19 and the brush module 16 to the base module 12 to form a preparation assembly.
9. Insert the device 10 into the pipe.
10. Advance the device 10 to the farthest flaw using the coiled tubing drive.
11. Clean the pipe surface.
12. Retract the device 10 to the next flaw.
13. Repeat steps 11 & 12 for each flaw.
14. Remove the device 10 from the pipe.

Set Patch

15. Remove the brush module 16 and the sensor module 19 (and the locomotor module 14 if necessary).
16. Attach the patch set test module 18 to form a patch assembly.
17. Load and prepare the patch.
18. Insert the device 10 into the pipe.
19. Advance the device 10 to the farthest unrepaired flaw using the coiled tubing drive 28.
20. Set patch.
21. Remove the device 10 from the pipe.
22. Repeat steps 17 through 21 for all remaining flaws.

The modules used with the device 10 can be constructed of, for example, steel tubing and machined aluminum. All joints can be sealed with, for example, o-rings or gaskets and the modules can be individually purged and pressurized with, for example, nitrogen or any non-oxygen containing gas to a pressure of, for example, 10–20 psig above the ambient within the pipeline to preclude leakage of the substance being carried by the pipe into the modules. The pressure within each module is monitored by an electronic sensor (not shown). If a drop in internal pressure within any module is detected, the device 10 can be turned off and withdrawn from the pipe to correct the problem.

The modules are equipped with hermetically sealed electrical connectors incorporated into custom quick disconnect fittings, allowing rapid reconfiguration of the device 10 into the various assemblies required. Flexible joints 20 interconnect the modules to provide the degrees of freedom necessary to negotiate bends in the pipe and the launch chamber. The flexible joints 20 and quick disconnects are described hereinbelow. The modules can also have equally spaced skids on their outside diameters to center them within the pipe. The skids can be flexible because of the necessity of negotiating bends in the pipe.

Figure 12:
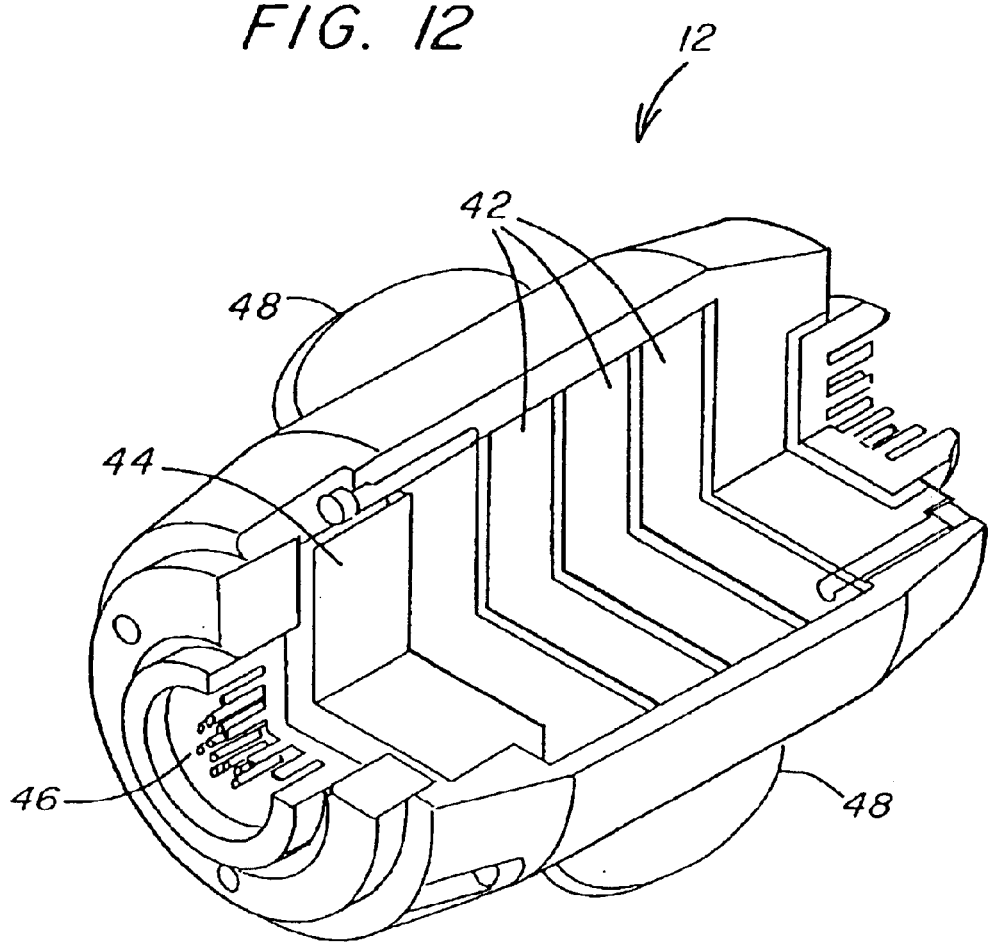
FIG. 12 illustrates a cutaway view of an embodiment of the base module of the multi-module pipe inspection and repair device of the present invention.
Figure 13:
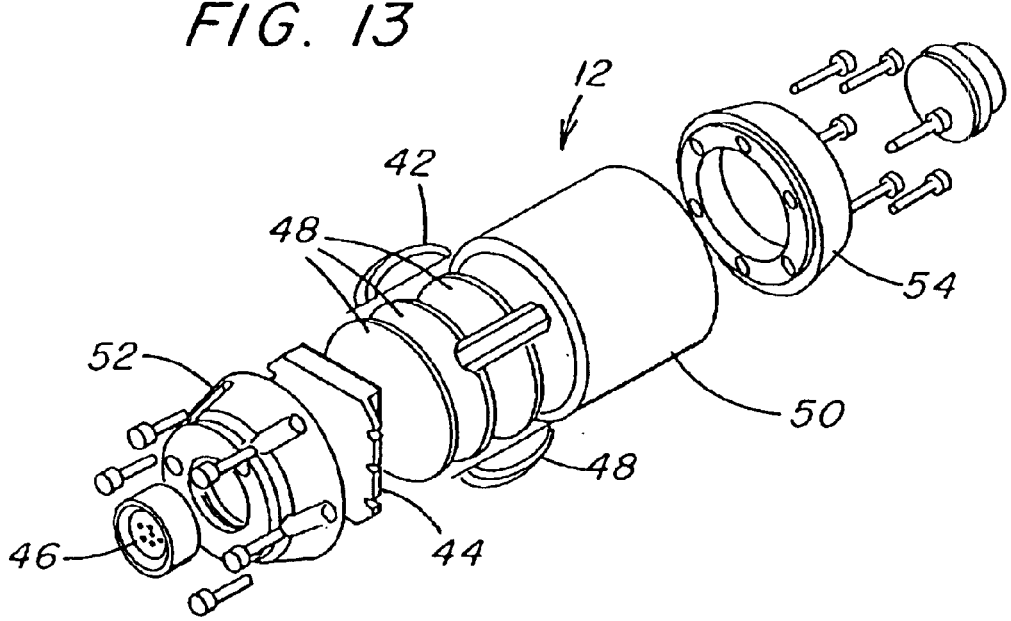
FIG. 13 illustrates an exploded view of the base module of FIG. 12.

FIG. 12 illustrates a cutaway view of an embodiment of the base module 12. The base module 12 interconnects the device 10 with the coiled tubing 22. The base module 12 includes circuit boards 42 which may house power conversion, communications, signal conditioning and control electronics. A DC-to-DC converter 44 reduces the tether live voltage from, for example, 150VDC to 48VDC. Additional, smaller converters can be added to reduce the voltage further as required by the electronic systems of the device 10. The base module 12 also includes a coiled tube drive interface 46, which is part of the modular interface connector system 34, to interface with the coiled tubing 22. The module 12 also includes centering skids 48. FIG. 13 illustrates an exploded view of the base module 12 of FIG. 12. The module 12 includes a housing tube 50 and end shells 52 and 54.

Figure 14:
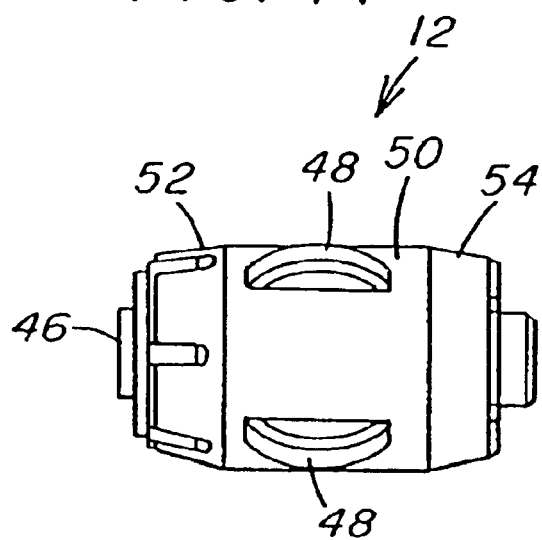
FIGS. 14 and 15 illustrate a side view and an end view, respectively, of the base module of FIG. 12.
Figure 15:
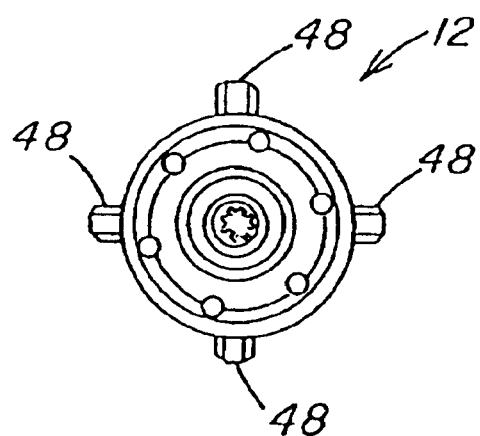

FIGS. 14 and 15 illustrate a side view and an end view, respectively, of the base module 12 of FIGS. 12 and 13.

Figure 15A:
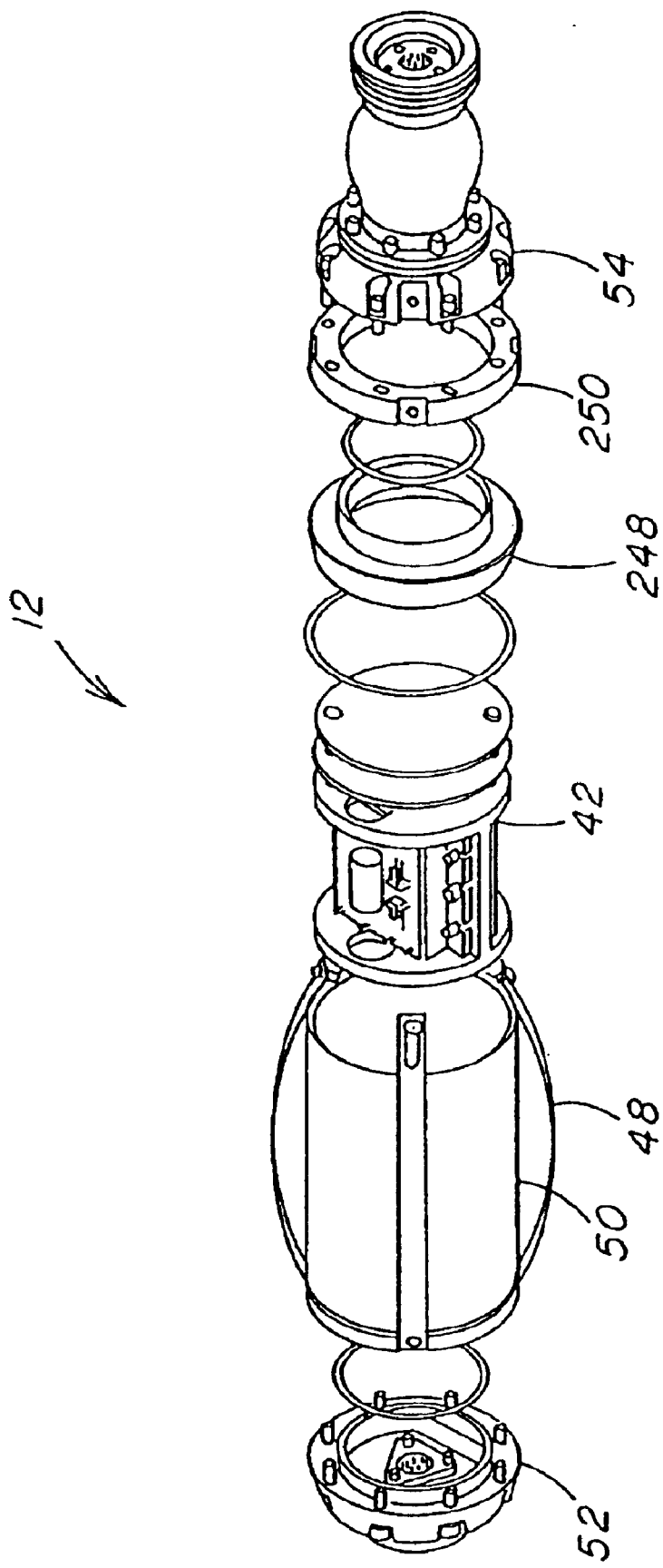
FIG. 15A illustrates an exploded view of another embodiment of the base module of the multi-module pipe inspection and repair device of the present invention.

FIG. 15A illustrates an exploded view of another embodiment of the base module 12 of the multi-module pipe inspection and repair device 10 of the present invention. A tube adapter threaded ring 248 and a closure retaining ring 250 attach the end shell 54 to the housing tube 50.

FIG. 15B illustrates a cutaway view of the base module 12 of FIG. 15A along the line A—A of FIG. 15C and FIGS. 15C and 15D illustrate end views of the base module 12 of FIG. 15A. FIGS. 15E and 15F illustrate the base module 12 of FIG. 15A.

Figure 16:
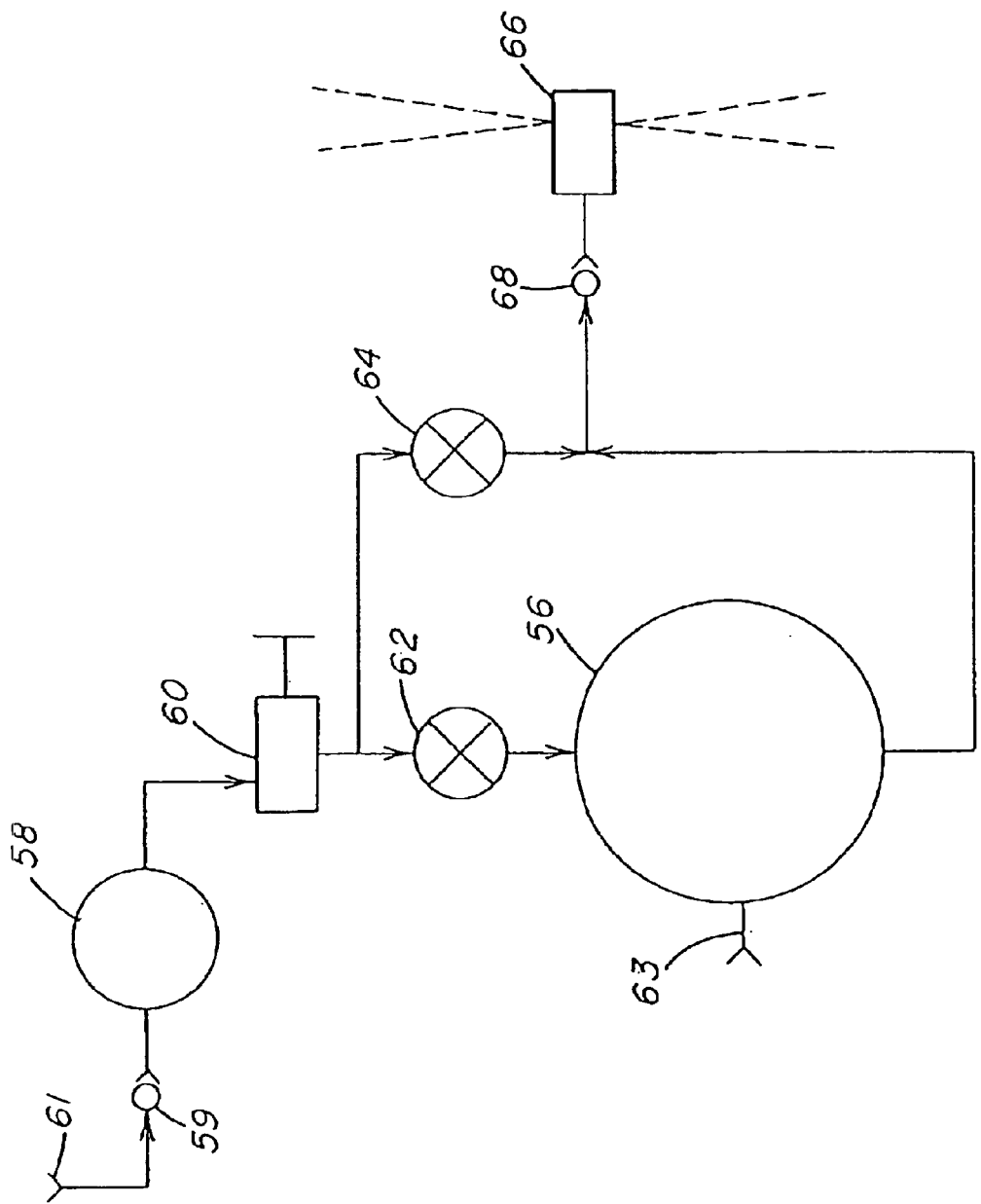
FIG. 16 illustrates a schematic of the marker module of the multi-module pipe inspection and repair device of the present invention.

FIG. 16 illustrates a schematic of the functional components of the marker module 38. The marker module 38 applies a marker, such as, for example, a stripe of paint, circumferentially around the inside of a pipe at a fixed distance from the detected flaws. The module 38 includes a reservoir tank 56 pressurized to, for example, 20 psi by an on board gas source 58. The gas can be, for example, nitrogen stored at, for example, 300 psi. A non-relieving regulator 60 drops the pressure to, for example, 20 psi above the ambient pressure of the material within the pipe. The regulator 60 is set through an access port prior to the device 10 being inserted into the pipe. The gas in the gas source 58 can be filled through a charge port 61 and the reservoir tank 56 can be filled through a fill and vent port 63. A check valve 59 prevents backflow from the gas source 58.

Solenoid valves 62 and 64 are used to control the flow of pressurized marker material or purge gas to a set of, for example, six fan-spray nozzles on a nozzle head 66. A check valve 68 in the nozzle head 66 prevents backflow of material from the pipe into the marker module 38. When a flaw is detected and located, the marker valve 62 is opened, pressurizing the tank 56 and spraying a circumferential stripe inside the pipe. The marker valve 62 is closed and the purge valve 64 is opened, supplying, for example, 20 psi nitrogen to clean the check valve 68 and the nozzle head 66. The purge gas also serves to dry the marker material more quickly.

Figure 17:
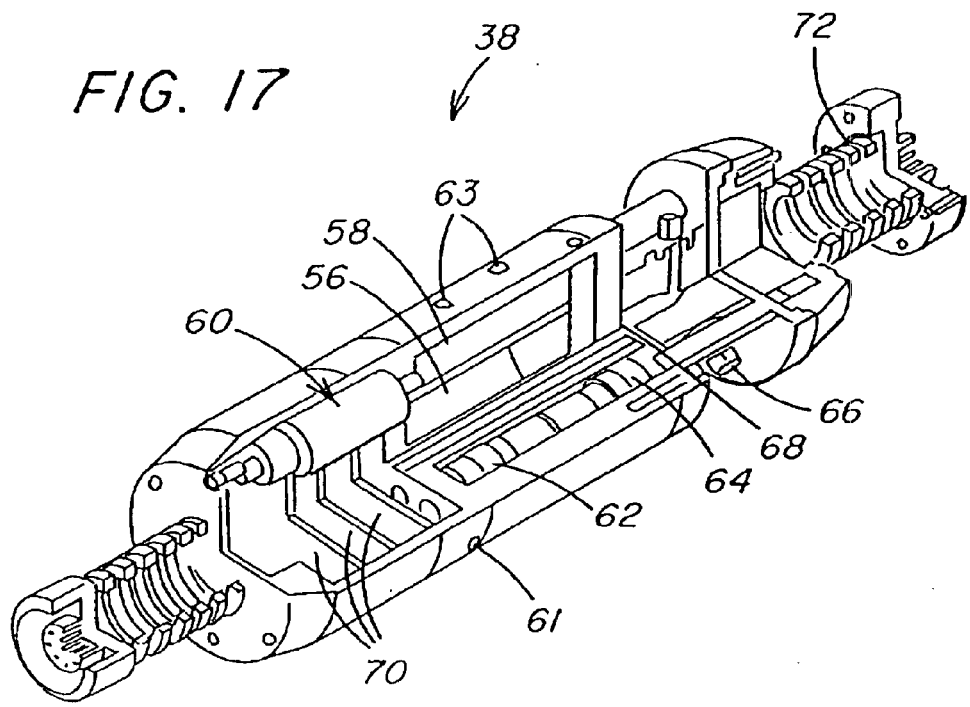
FIG. 17 is a diagram illustrating a cutaway view of an embodiment of the marker module.

FIG. 17 is a diagram illustrating a cutaway view of an embodiment of the marker module 38. The gas source 58, the marker reservoir tank 56, and fluid and gaslines may be machined into the center body of the module 38. Similarly, valve plates for the valves 62 and 64 have machined fluid and gas passages and mounting provisions for manifold-type solenoid valves. The module 38 includes circuit boards 70 and an MFL connector 72.

Figure 18:
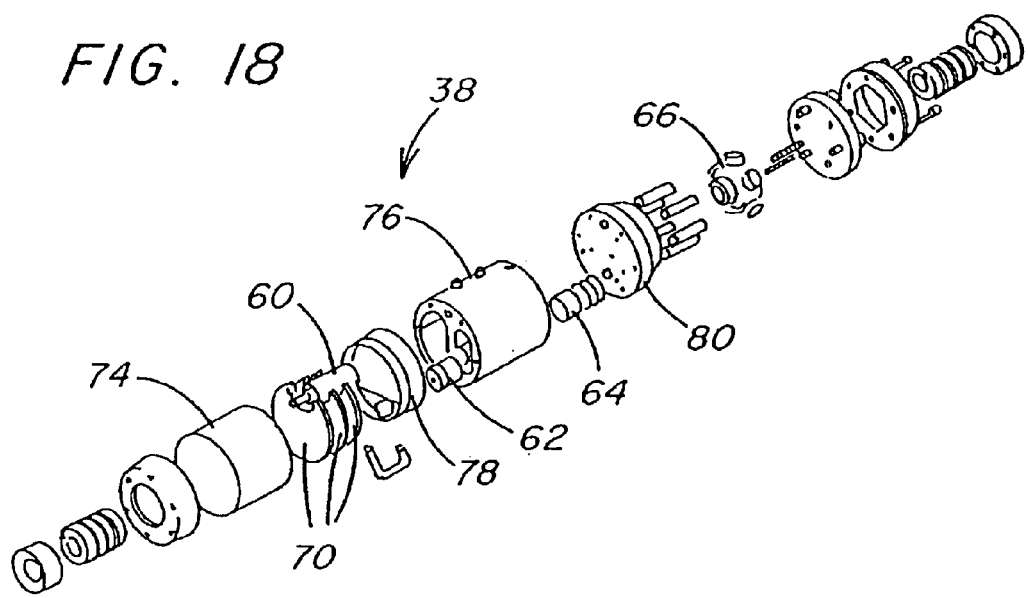
FIG. 18 illustrates an exploded view of the marker module of FIG. 17.
Figure 19:
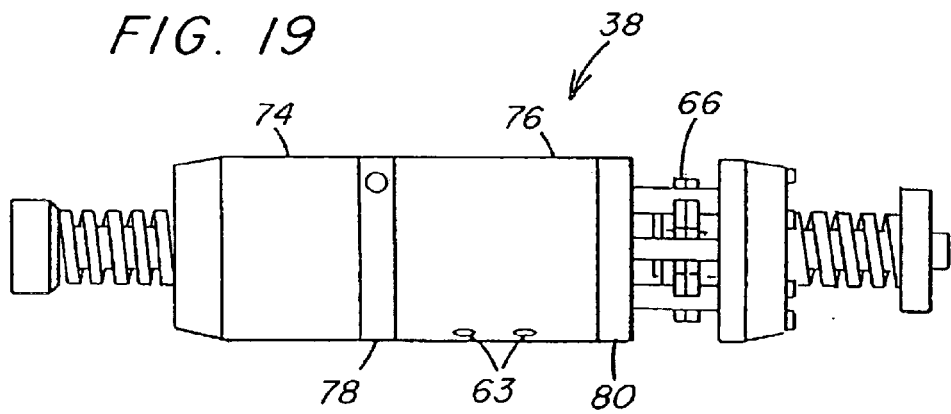
FIGS. 19 and 20 illustrate a side view and an end view, respectively, of the marker module of FIG. 17.
Figure 20:
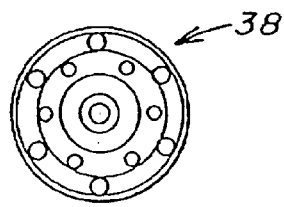

FIG. 18 illustrates an exploded view of the module 38 of FIG. 17. The solenoid valves 62 and 64, the check valve 68, the pressure regulator 60, the nozzle head 66 and fluid fittings can be, for example, off-the-shelf standard items. The module 38 includes a housing tube 74 and a pressure chamber 76. The module 38 also includes a rear valve plate 78 and a mid-valve plate 80. FIGS. 19 and 20 illustrate a side view and an end view, respectively, of the marker module 38 of FIGS. 17 and 18.

Figure 20A:
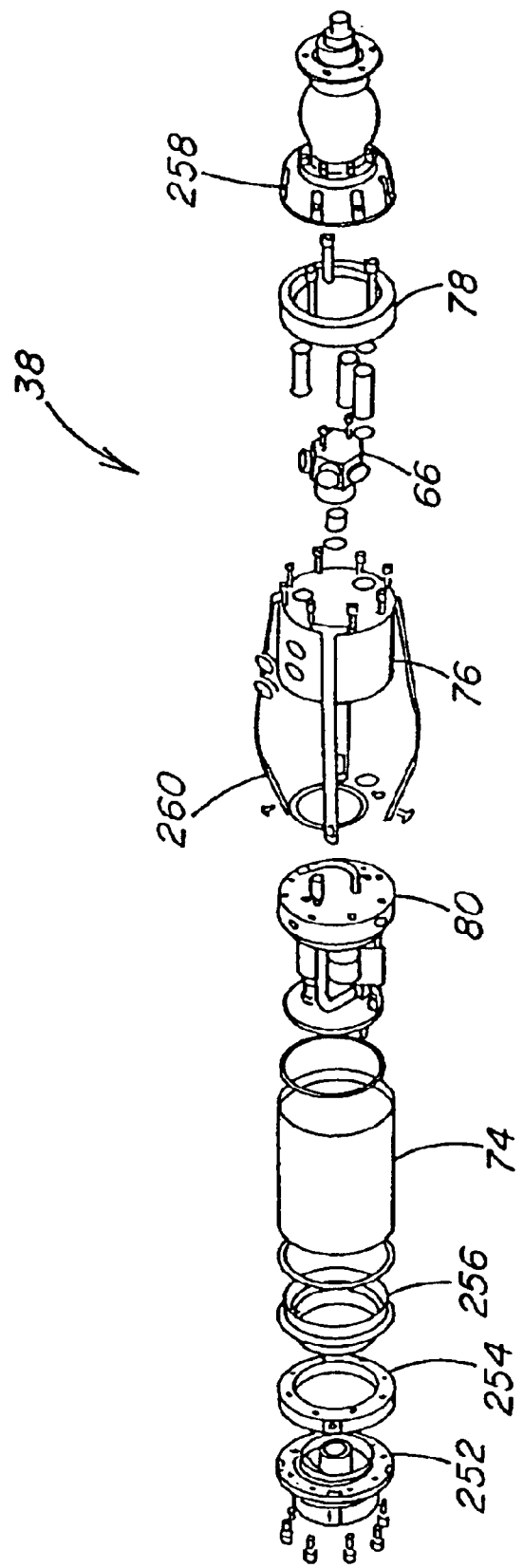
FIG. 20A illustrates an exploded view of another embodiment of the marker module of the multi-module pipe inspection and repair device of the present invention.

FIG. 20A illustrates an exploded view of another embodiment of the marker module 38 of the multi-module pipe inspection and repair device 10 of the present invention. A rear closure 252, a closure retaining ring 254, and a threaded ring 256 close one end of the module 38. A front closure 258 closes the other end of the module 38. Skids 260 are provided on the housing tube to facilitate navigation in a pipe.

Figure 21:
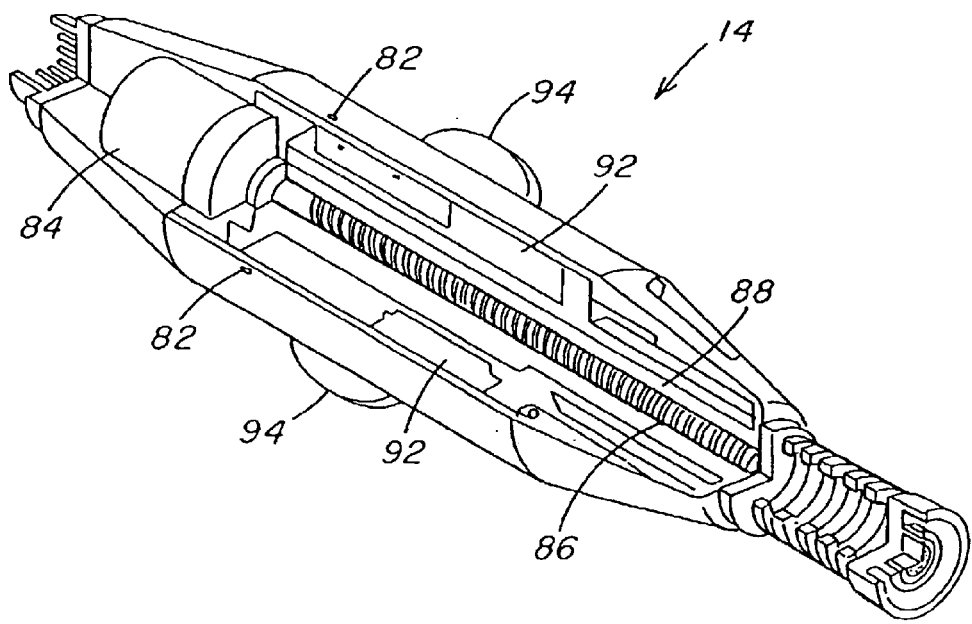
FIG. 21 illustrates a cutaway view of an embodiment of the locomotor module of the multi-module pipe inspection and repair device of the present invention.

FIG. 21 illustrates a cutaway view of an embodiment of the locomotor module 14. The locomotor module 14 provides the necessary axial movement to the brush module 16 so as to clean an area of pipe of sufficient length to accommodate a patch. The module 14 also has on board sensors 82 which can be, for example, diffuse light sensors which detect the marker provided by the marker module 38 to accurately locate a flaw within the pipe. The diffise light sensors 82 combine both a light source and a detectors in one package.

Figure 22:
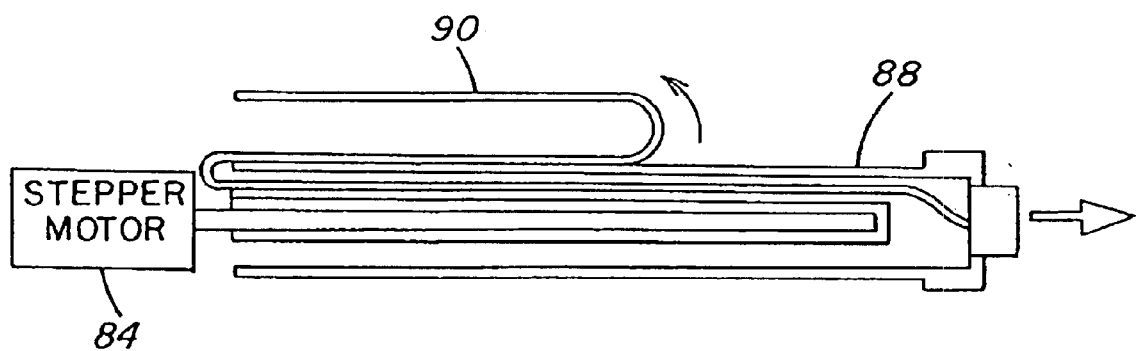
FIG. 22 illustrates a cross sectional view of a portion of the locomotor module of FIG. 21.

The combination of four sensors 82 and six fan nozzles on the nozzle head 66 of the marker module 38 ensures that at least two sensors 82 will detect the marker even if each fan nozzle does not achieve a full 60° coverage of the pipe. The locomotion function of the locomotor module 14 is provided by a stepper motor 84, which drives an acme screw 86. The acme nut is attached to a ram 88. The ram 88 is constructed of coaxial tubes to provide a passage for wire harnessing. Flexible ribbon cables 90 attach the module's electronics to the ram 88 as shown in FIG. 22. Lugs on the ram 88 prevent rotation when the acme screw 86 is driven. The position of the ram 88 is obtained by counting steps of the stepper motor 84 and the end of travel is indicated with proximity type switches (not shown). The locomotor module 14 may also include circuit boards 92 and centering skids 94. The locomotor module 14 is a self-moving module and may be tethered to the coiled tubing 22 or may be untethered.

Figure 23:
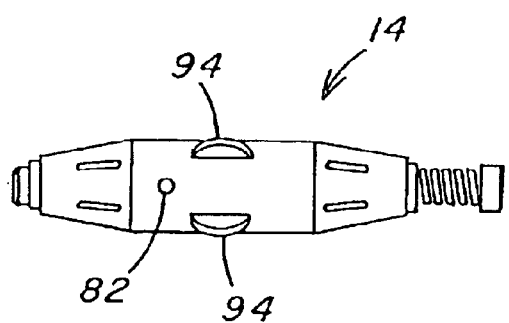
FIGS. 23 and 24 illustrate a side view and an end view, respectively, of the locomotor module of FIG. 21.
Figure 24:
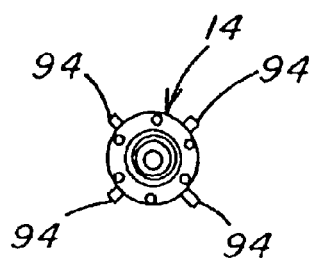

FIGS. 23 and 24 illustrate a side view and an end view, respectively, of the locomotor module 14 of FIG. 21.

Figure 25:
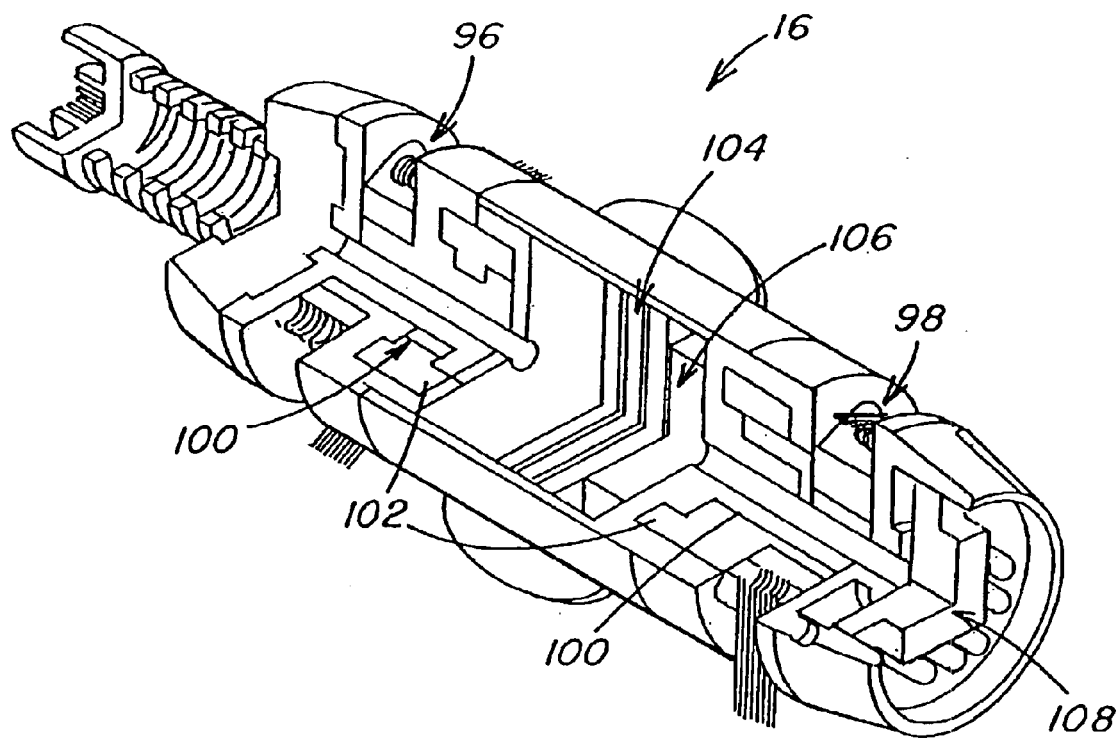
FIG. 25 illustrates a cutaway view of an embodiment of the brush (prep) module of the multi-module pipe inspection and repair device of the present invention.

FIG. 25 illustrates a cutaway view of an embodiment of the brush (prep) module 16. The brush module 16 is used to prepare the interior surface of the pipe around the vicinity of a flaw to ensure a good seal with the patch. The brush module 16 may have two brushes 96 and 98 separated by, for example, approximately 6 inches. Combined with the 6 inch stroke of the locomotor module 14, the brush module 16 can clean a 12 inch area of pipe. The type of brush can be, for example, abrasive flap wheels, abrasive strand wheels, or wire brushes of various configurations, or any other abrasive medium.

The brush module 16 shown in FIG. 25 includes two independently driven, contra-rotating brush wheels driven by electronically commutated pancake style motors. The motors include rotors 100 and stators 102. The brush wheels are designed so that, at rest, the abrasive elements are sprung away from the walls of the pipe, thus allowing the device 10 to be easily moved within the pipe. When powered, centrifugal force causes the abrasive elements to contact the pipe walls. Drive electronics for the motors are located between them on circuit boards 104 and the module 16 includes a DC—DC converter 106. All electrical wiring passes through the hollow shafts of the motors.

A camera and illumination system 108 is included on the front of the module 16 to provide the operator with the ability to inspect the cleaned area and repeat the cleaning operation if necessary.

Figure 26:
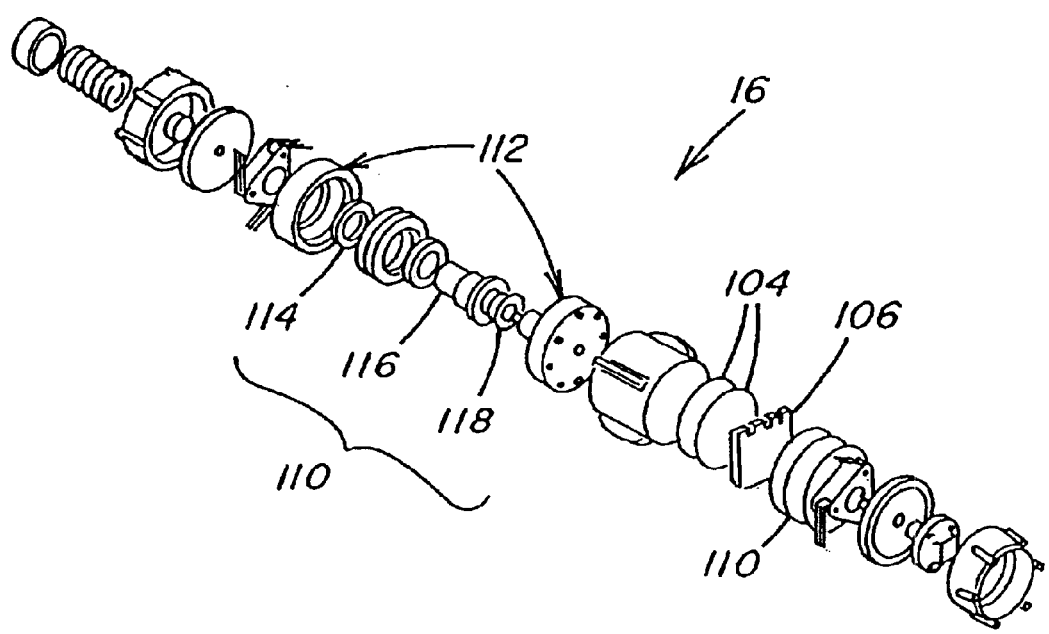
FIG. 26 illustrates an exploded view of the brush module of FIG. 25.

FIG. 26 illustrates an exploded view of the brush module 16 of FIG. 25. The module 16 includes motor/brush assemblies 110. Each assembly 110 includes a housing 112, a front bearing 114, a brush shaft 116, and a rear bearing 118.

Figure 27:
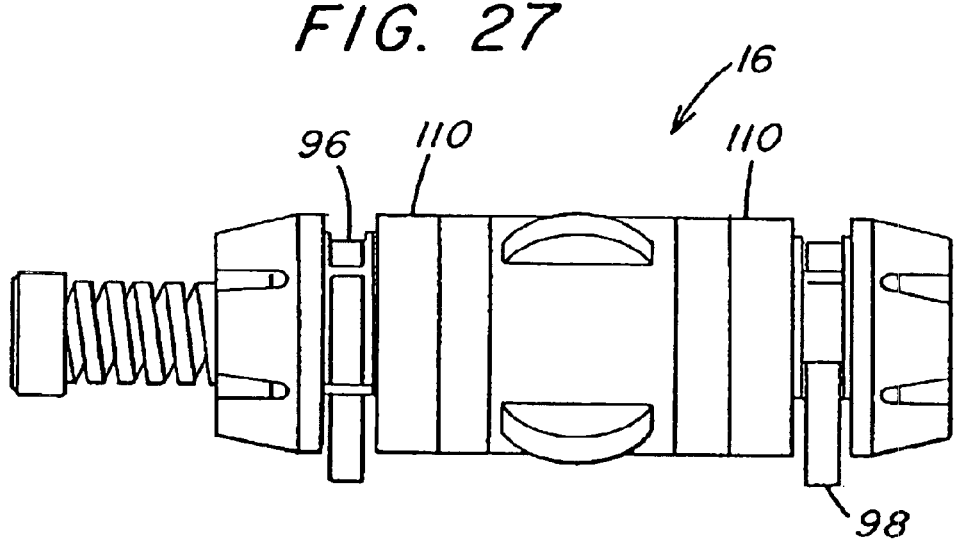
FIGS. 27 and 28 illustrate a side view and an end view, respectively, of the brush module of FIG. 25.
Figure 28:
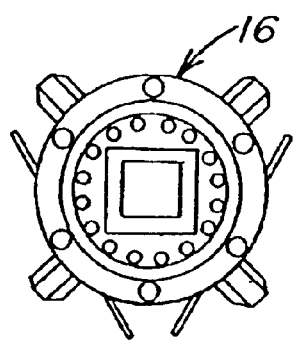

FIGS. 27 and 28 illustrate a side view and an end view, respectively, of the brush module 16 of FIGS. 25 and 26.

Figure 28A:
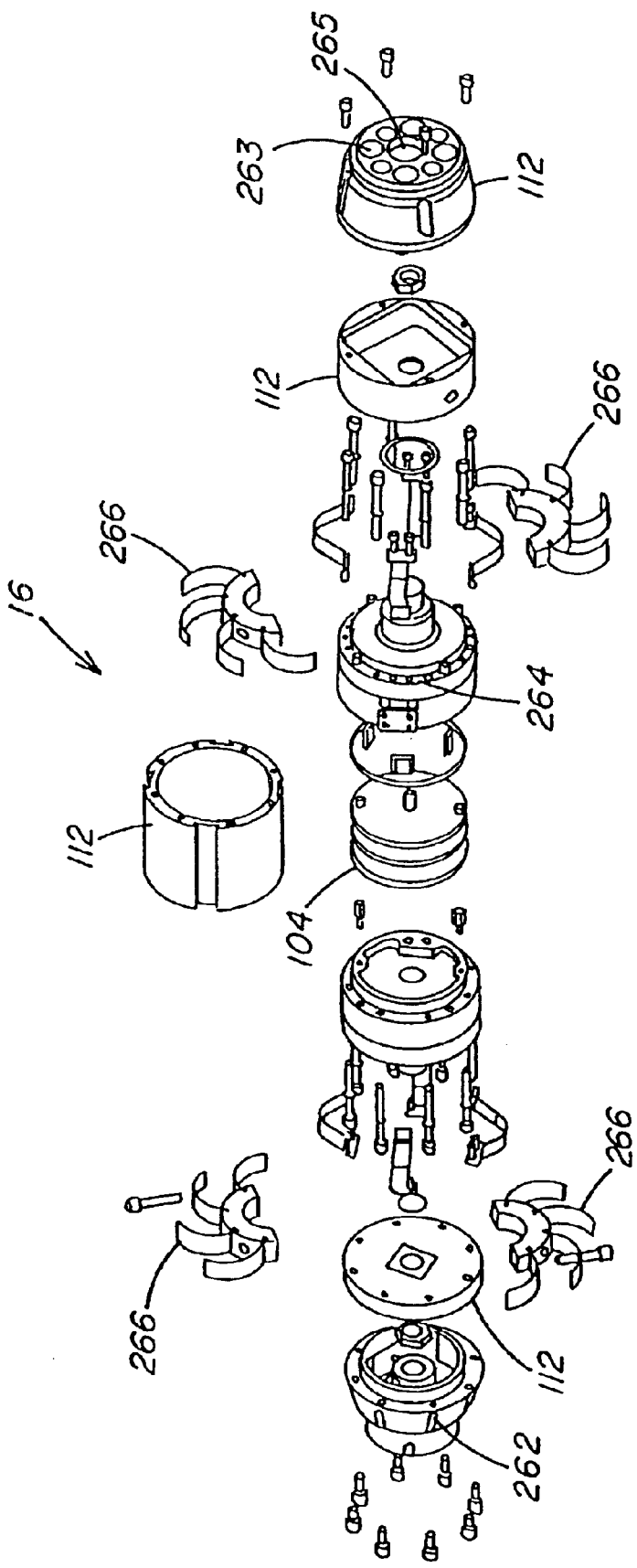
FIG. 28A illustrates an exploded view of another embodiment of the brush (prep) module of the multi-module pipe inspection and repair device of the present invention.

FIG. 28A illustrates an exploded view of another embodiment of the brush (prep) module 16 of the multi-module pipe inspection and repair device 10 of the present invention. A rear closure 262 closes one end of the module 16. A motor 264 drives brush assemblies 266. The brush assemblies 266 have abrasive sheets which are normally retracted but expand to contact the sides of the pipe to be cleaned when the brush assemblies 266 are rotated. The housing 112 may contain a camera (not shown) having a lens 265 and light sources 263. The camera can be, for example, a color CCD or CMOS board camera. The light sources 263 can be, for example, pulse width modulated (PWM) intensity-controlled light emitting diodes (LEDs).

FIG. 28B illustrates a side view of the brush module 16 of FIG. 28A and FIG. 28C illustrates an exploded view of the brush module 16 of FIG. 28A. FIGS. 28D and 28E illustrate end views of the brush module 16 of FIG. 28A and FIG. 28F illustrates the brush module 16 of FIG. 28A.

Figure 28G:
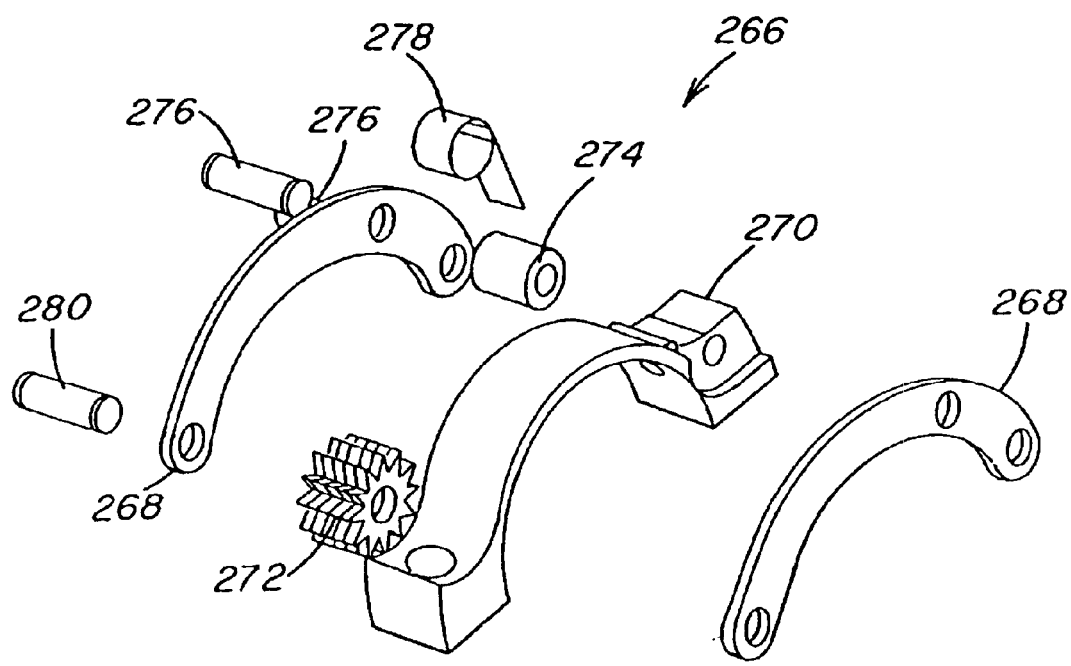
FIG. 28G is an exploded view of the brush assembly of FIG. 28A.

FIG. 28G is an exploded view of the brush assembly 266 of FIG. 28A. The assembly 266 includes two arms 268 which may pivot around a brush holder 270. The assembly 266 includes a brush 272, which is illustrated as a wheel fashioned in a star shape. The brush 272 can be constructed of, for example, hardened tool steel. A standoff 274 and two pins 276 hold the arms 268 together and to the holder 270. A spring 278 keeps the arms 268 in the retracted position (away from the pipe wall to be cleaned). When the assembly 266 is rotated, the tension of the spring is overcome by centrifugal force and the brush 272 may contact the pipe walls. A pin 280 holds the brush 272 to the arms 268. The brush 272 is designed such that when it is rotated and contacts the walls of a pipe, large-scale rust is removed from the wall of the pipe. Such large-scale rust is advantageous in that it settles in the pipe and is not carried through the pipe as may happen if fine particles are removed from the pipe walls.

Figure 28I:
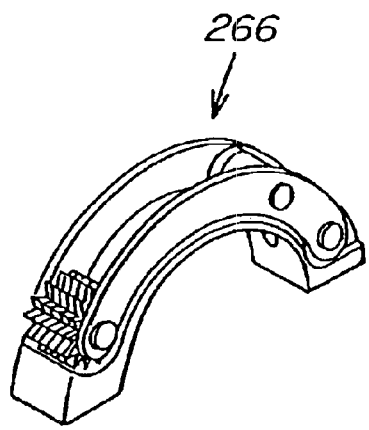
FIG. 28I illustrates the brush assembly of FIG. 28G.
Figure 28J:
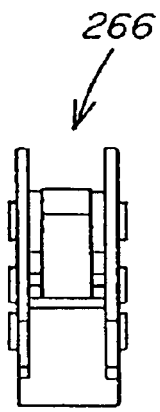
FIGS. 28J and 28K illustrate end views of the brush assembly of FIG. 28G.
Figure 28H:
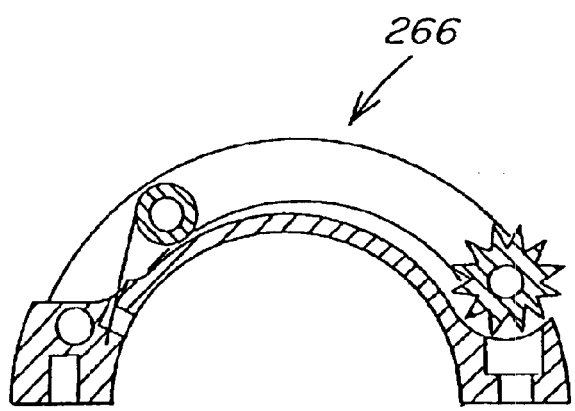
FIG. 28H illustrates a side view of an embodiment of the brush assembly of FIG. 28G.
Figure 28L:
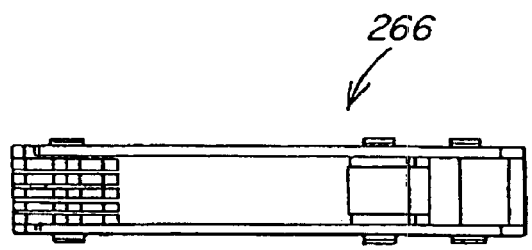
FIG. 28L is a top view of the brush assembly of FIG. 28G.
Figure 28K:
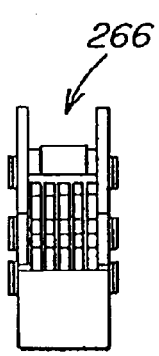
Figure 28M:
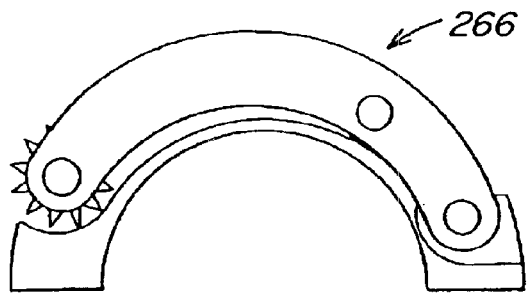
FIG. 28M is a side view of the brush assembly of FIG. 28O.

FIG. 28H illustrates a side view of the brush assembly 266 of FIG. 28G and FIG. 28I illustrates the brush assembly 266 of FIG. 28G. FIGS. 28J and 28K illustrate end views of the brush assembly 266 of FIG. 28G, FIG. 28L is a top view of the brush assembly 266 of FIG. 28G, and FIG. 28M is a side view of the brush assembly 266 of FIG. 28G.

Figure 29:
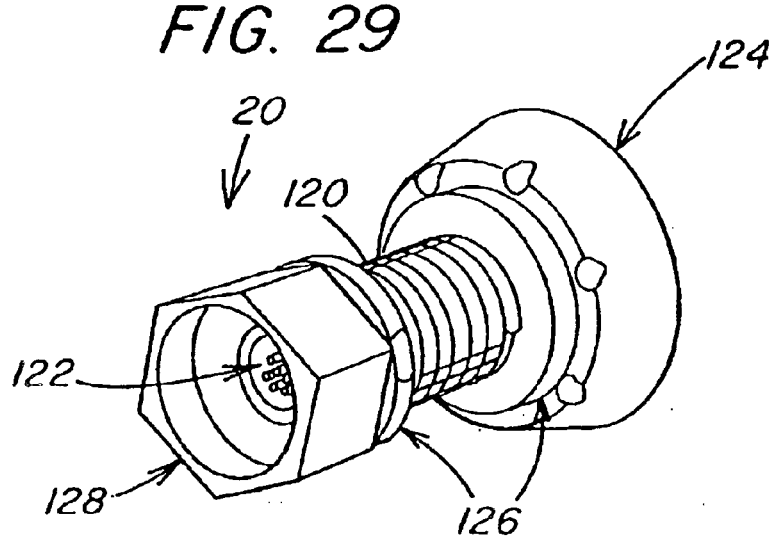
FIG. 29 is a diagram illustrating a view of an embodiment of the flexible joint of the multi-module pipe inspection and repair device of the present invention.
Figure 30:
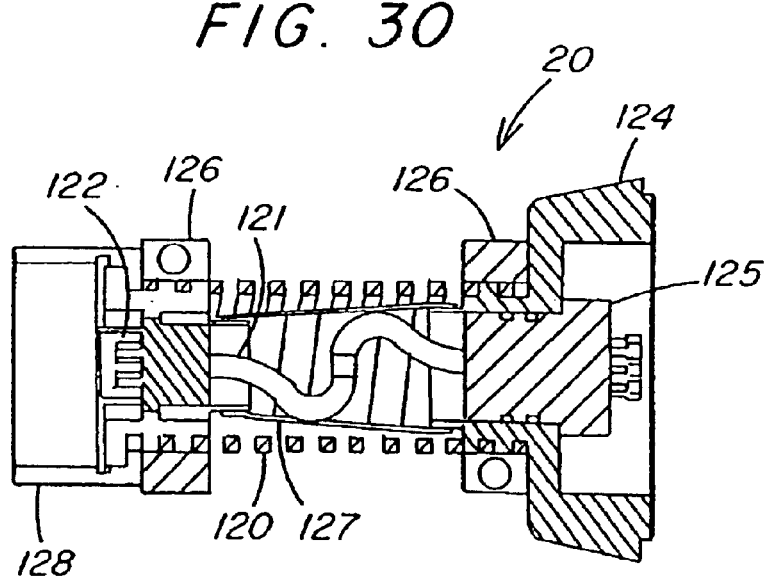
FIG. 30 is a diagram illustrating a cross-sectional view of the flexible joint of FIG. 29.

FIG. 29 is a diagram illustrating a view of an embodiment of the flexible joint 20 and FIG. 30 is a diagram illustrating a cross-sectional view of the joint 20 of FIG. 29. Modules of the device 10 are interconnected by the flexible joint 20, which allows the device 10 to negotiate bends in the pipe and at the launch point.

The joint 20 uses a close wound square coil spring 120, which can be compressed to solid height without damage. A flexible wire bundle 121 electrically interconnects the modules at a connector 122 to pass control and feedback signals between the modules that are interconnected by the joint 20. The bundle 121 may also include a tube for passing gases or fluids through the joint 20. On the module side of the wire bundle 121 at a module end shell 124 is a hermetically sealed feed-thru 125. The bundle 121 has sufficient slack to preclude the tensioning of the wires when the coil spring 120 is under tension. Lanyards (not shown) between spring clamps 126 preclude overextending the coil spring 120. A spiral wound metal sleeve 127 inside the coil spring 120 protects the wire bundle from objects which may penetrate between the spring coils. A locking sleeve 128 is coarse threaded to connect with its mate and the connector 122 inside is keyed for proper orientation.

Figure 30A:
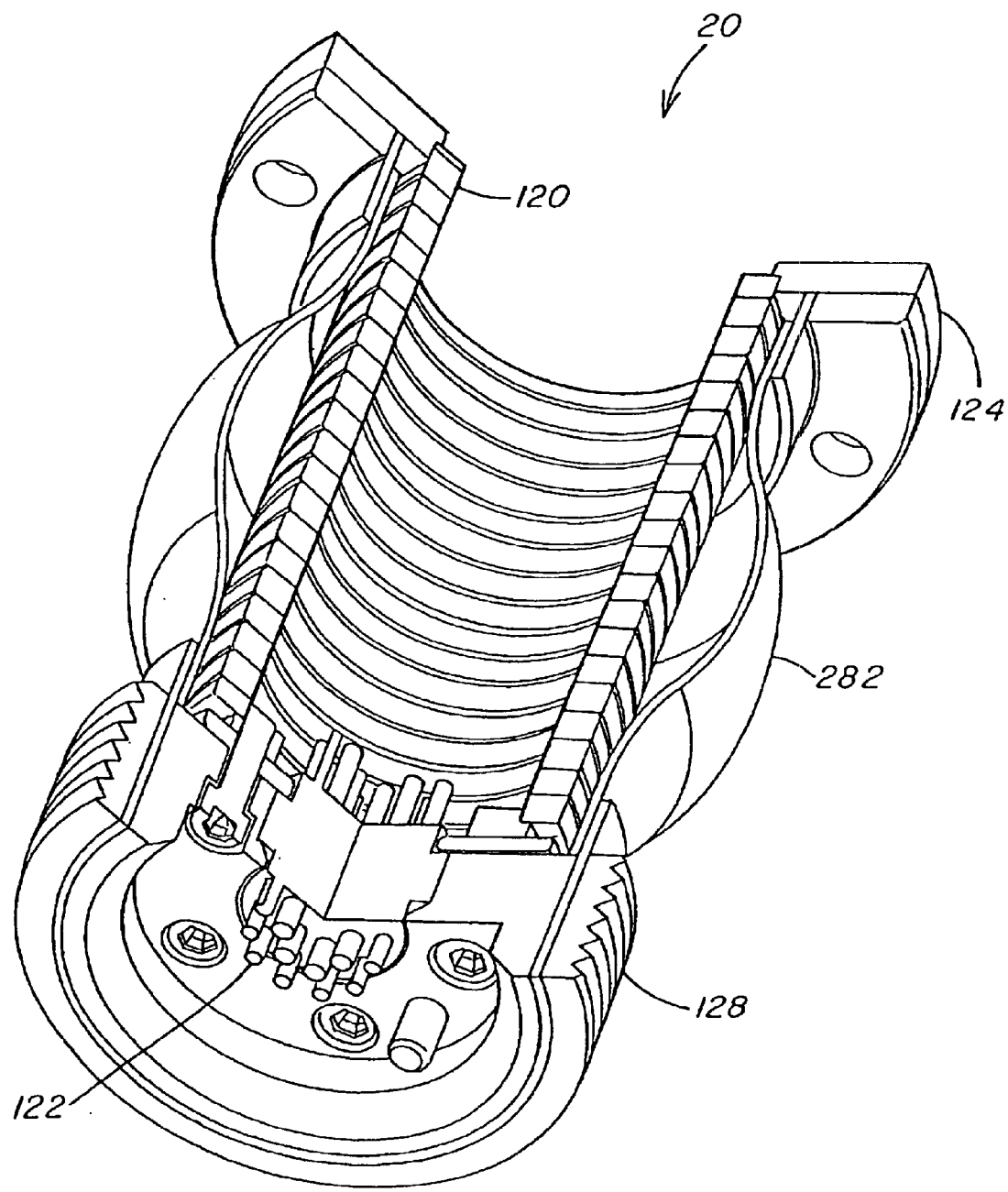
FIG. 30A is cutaway diagram illustrating another embodiment of the flexible joint of the multi-module pipe inspection and repair device of the present invention.
Figure 30B:
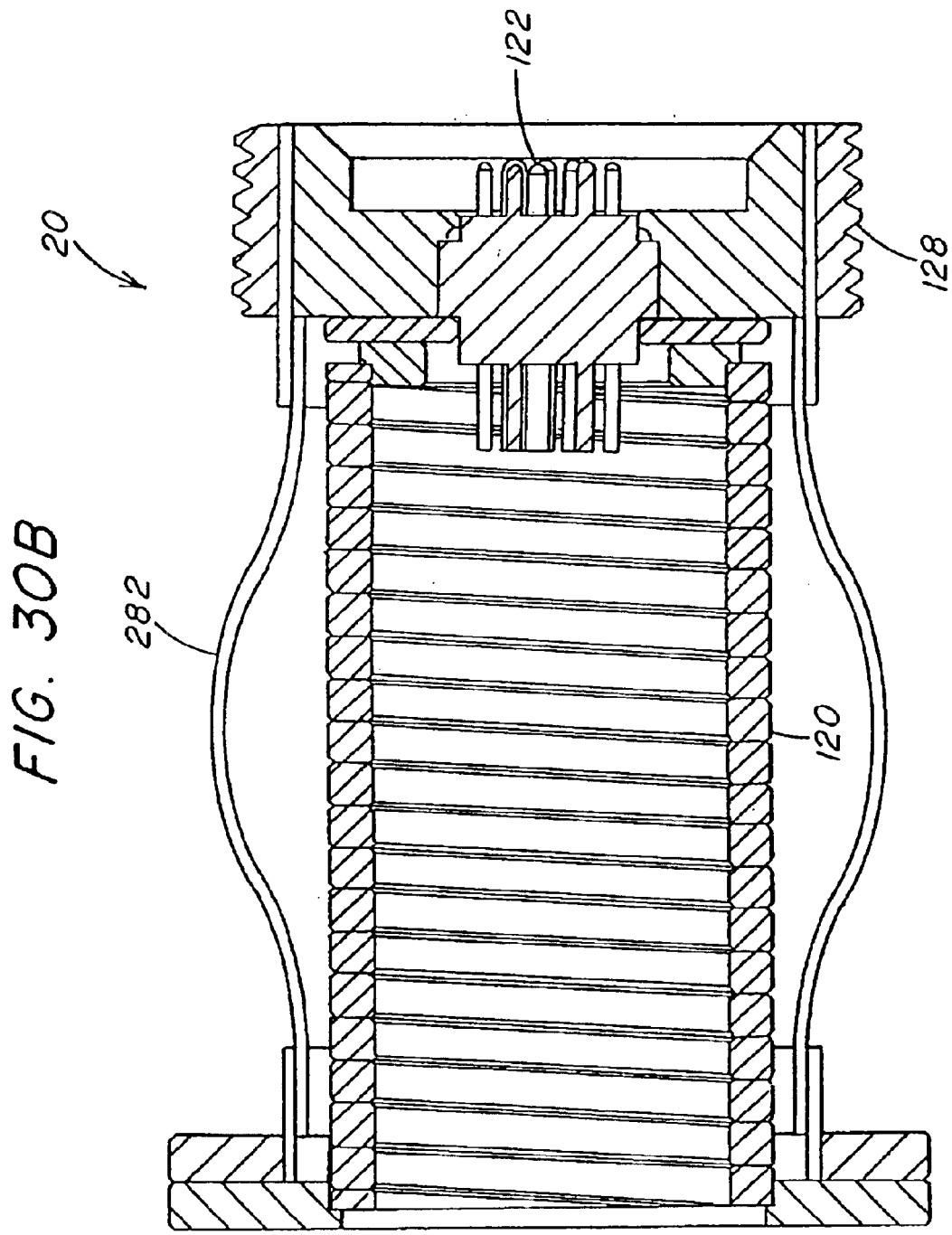
FIG. 30B is a side cutaway view of the flexible joint of FIG. 30A.

FIG. 30A is cutaway diagram illustrating another embodiment of the flexible joint 20 of the multi-module pipe inspection and repair device 10 of the present invention. A wire mesh 282 surrounds the spring 120. The mesh 282 can be, for example, a stainless steel criss-cross wire mesh. Other suitable material may be used in place of the wire mesh 282. For example, cords constructed of, for example, Kevlar, and fastened with epoxy, can be used instead of a wire mesh. The combination of the wire mesh 282 and the spring 120 provides for sufficient angular detention as the device 10 navigates a pipe while prohibiting the joint 20 from over-rotating or over-translating. FIG. 30B is a side cutaway view of the flexible joint 20 of FIG. 30A. The joint 20 may include a wire bundle (not shown) and/or a tube for passing fluids or gases (not shown) which pass through the cavity created by the spring 120. The joint 20 may also be constructed using ball joints to make the joint 20 flexible.

Figure 30C:
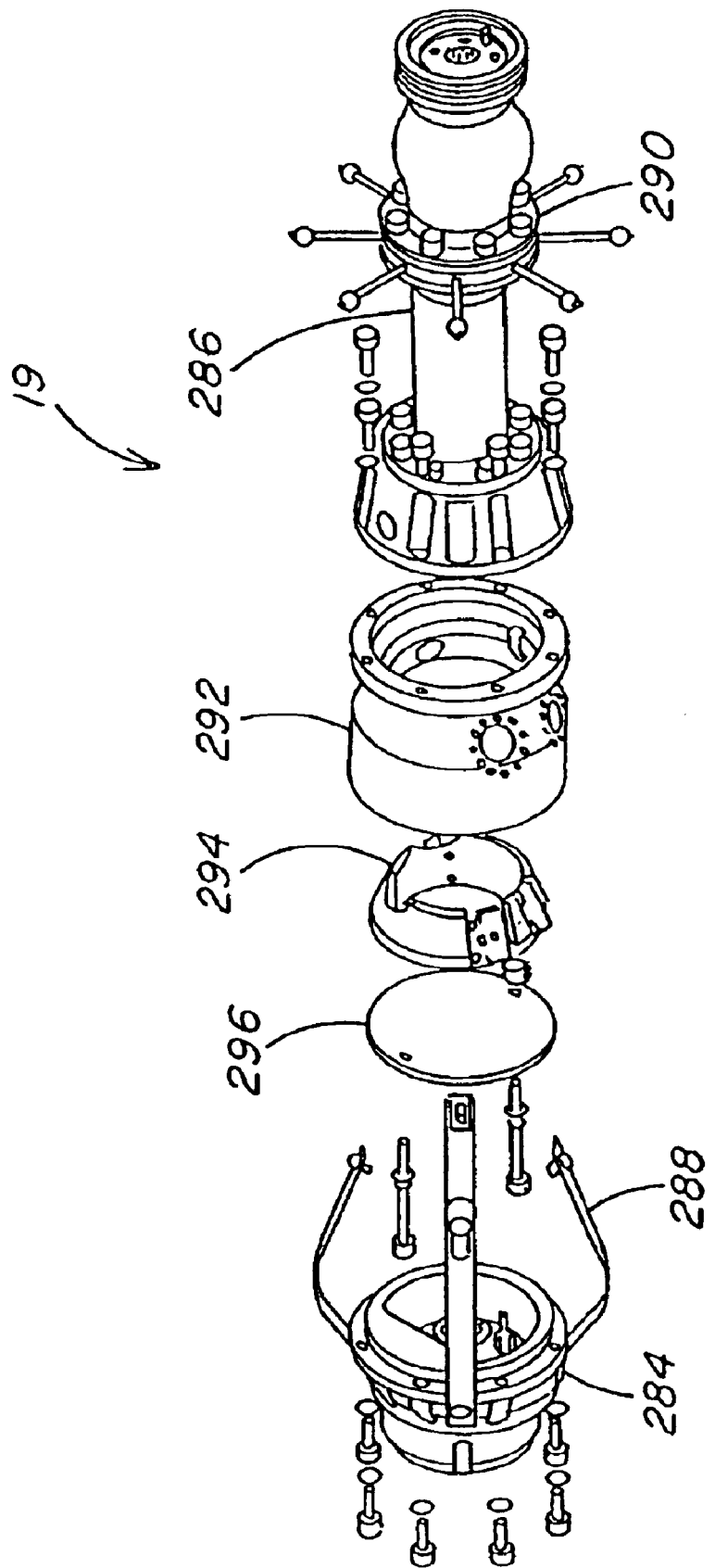
FIG. 30C is an exploded view of an embodiment of the sensor module of the multi-module pipe inspection and repair device of the present invention.

FIG. 30C is an exploded view of an embodiment of the sensor module 19 of the multi-module pipe inspection and repair device 10 of the present invention. A rear closure 284 and a front closure 286 close the front of the module 19. Skids 288 facilitate movement At of the module 19 in a pipe. A centralizer 290 keeps the module 19 substantially centered in the pipe regardless of the direction of travel of the module 19. A housing 292 houses sensors 294, which are controlled by electronics on the circuit board 296. The sensors 294 can be, for example, infrared reflective, acoustic, magnetic, or optical sensors.

FIG. 30D is a cutaway view of the sensor module 19 of FIG. 30C sectioned along the A—A axis of FIG. 30E. FIGS. 30E and 30F are end views of the sensor module 19 of FIG. 30C and FIGS. 30G and 30H illustrate the sensor module 19 of FIG. 30C.

FIGS. 30I and 30J are diagrams illustrating a sensing technique used by the MFL module 36 of the present invention. In FIG. 30I, a magnet 298 placed near steel (e.g. a pipe wall) 300 produces a magnetic flux. As illustrated in FIG. 30J, if the steel 300 has metal loss, the magnet experiences a flux leakage. The MFL module 36 thus senses the flux leakage to determine where metal loss (e.g. a thin wall or a hole) has occurred.

Figure 30K:
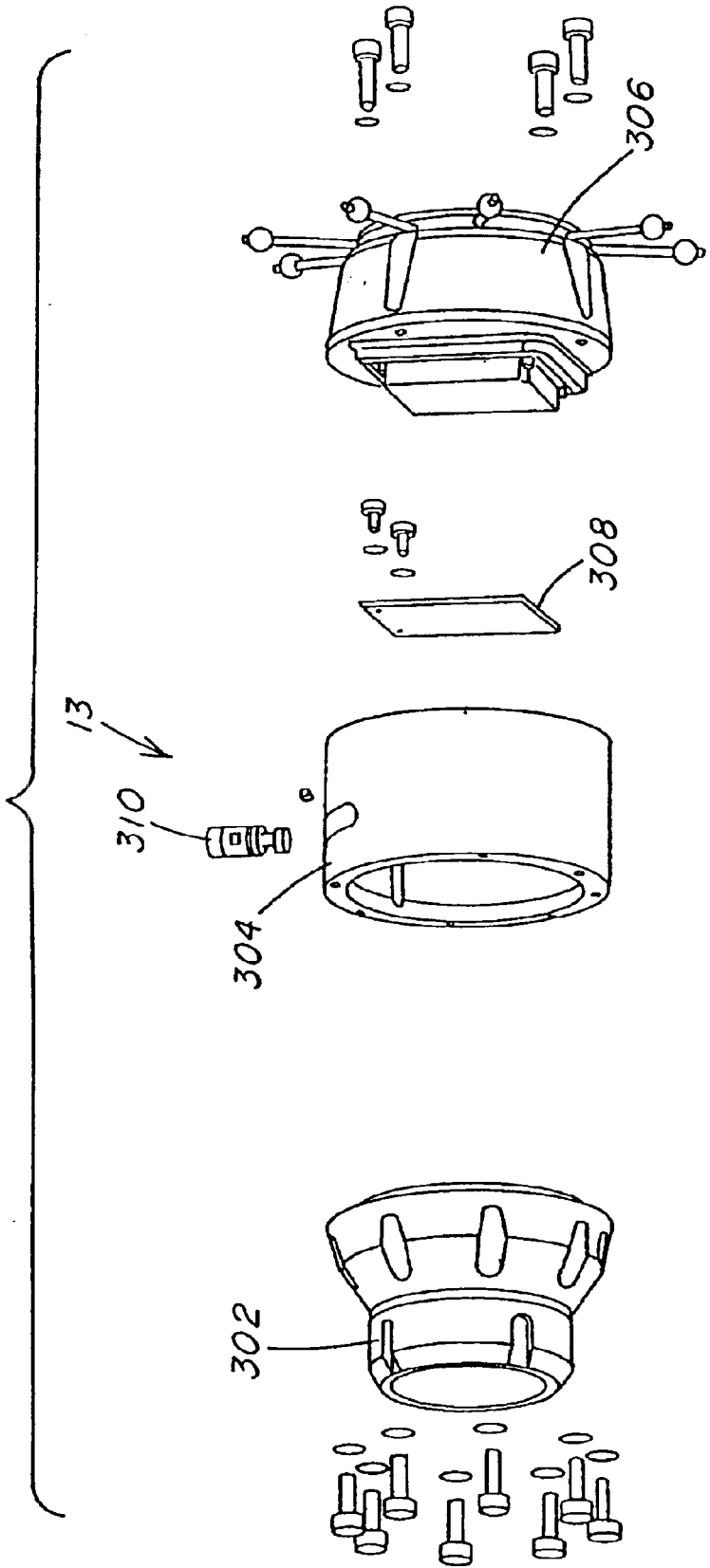
FIG. 30K is an exploded view an embodiment of the camera module of the multi-module pipe inspection and repair device of the present invention.
Figure 30A:
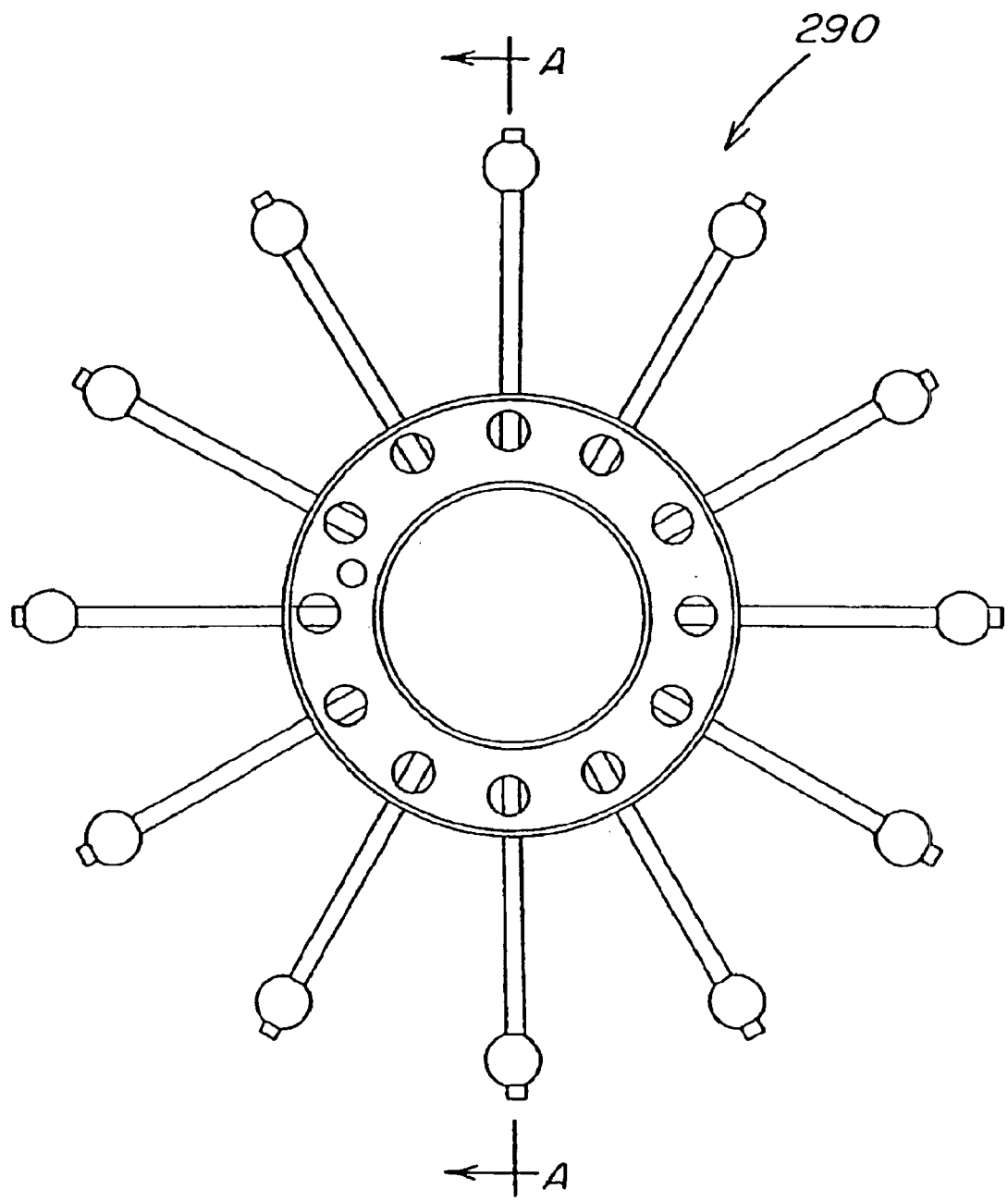
Figure 30A:
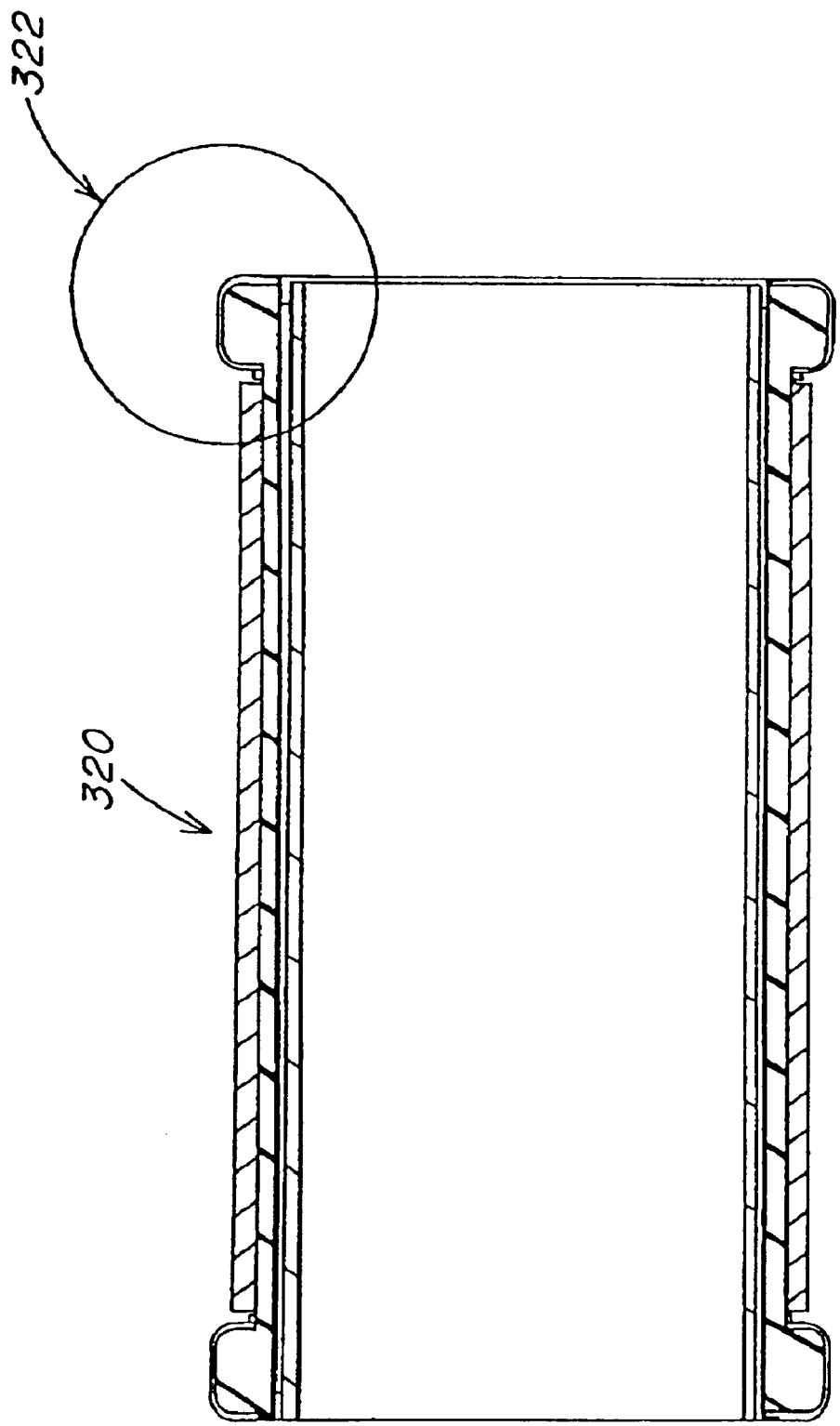
Figure 30A:
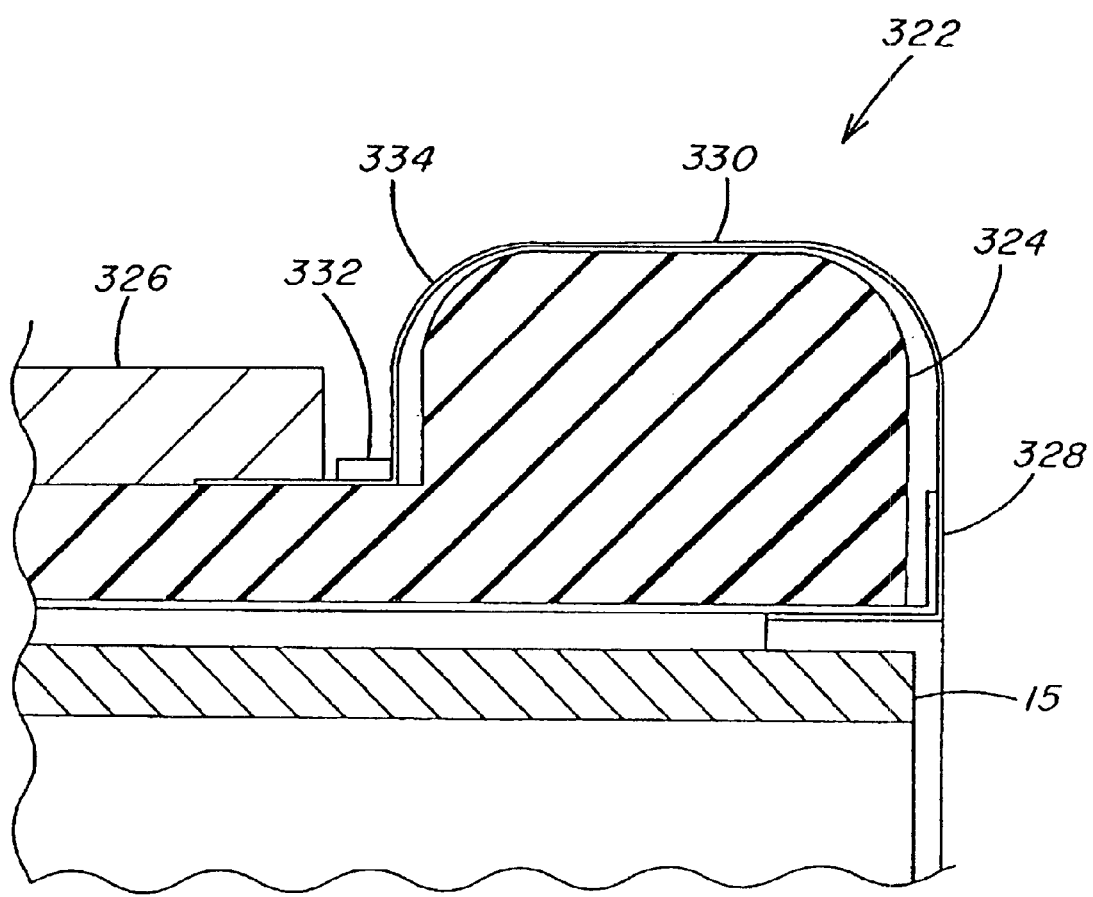
Figure 30A:
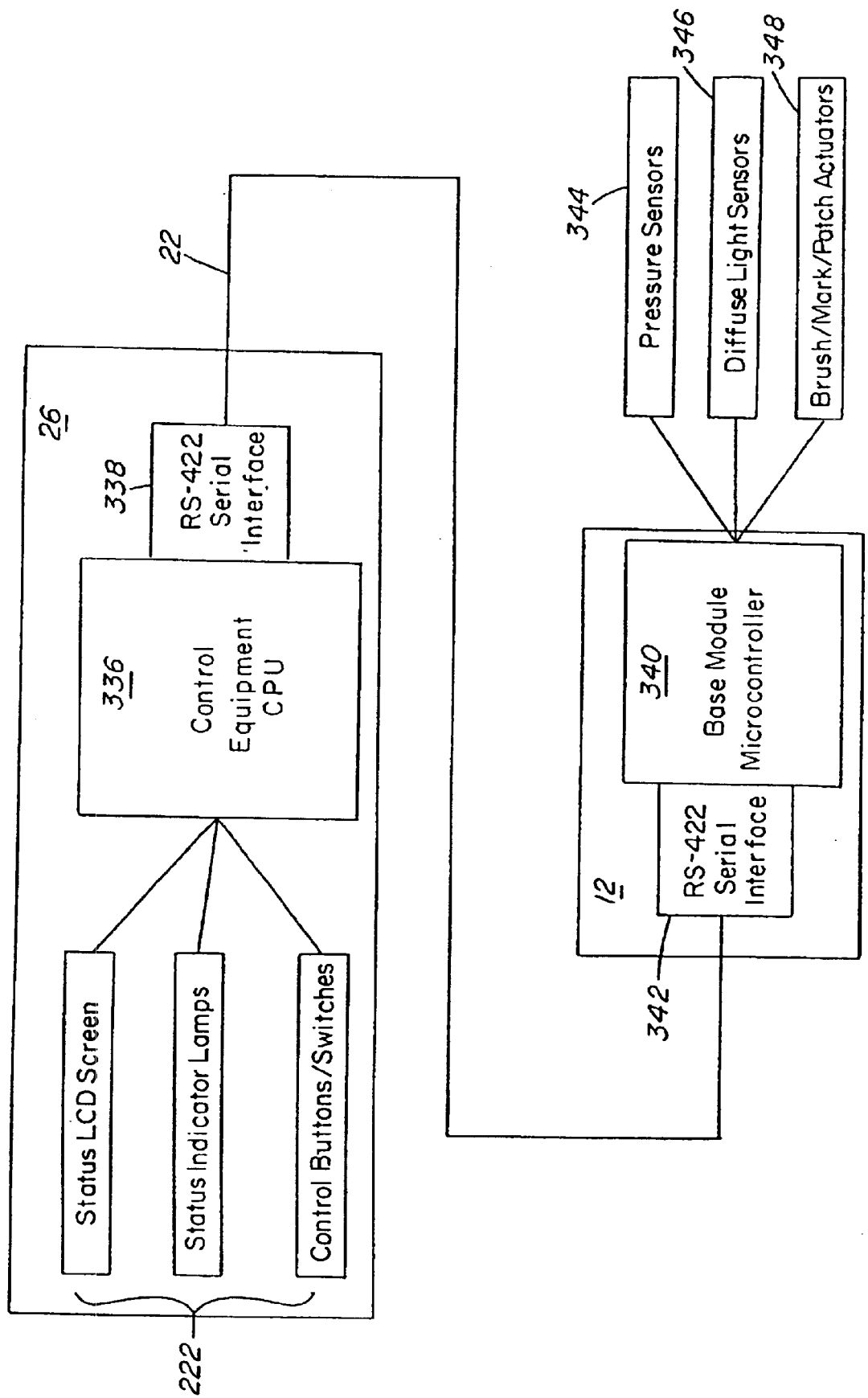

FIG. 30K is an exploded view an embodiment of the camera module 13 of the multi-module pipe inspection and repair device 10 of the present invention. A rear closure 302, a housing 304, and a front housing 306 comprise the body of the module 13. The front housing 306 contains a camera (not shown), camera lenses (shown below), and a light sources (shown below). The camera can be, for example, a color CCD camera or a CMOS board-camera. A circuit board 308 contains the electronics needed to operate the camera and control the intensity of the light source. A bleed valve 310 ensures that the module 13 will have positive pressure with respect to its environment to ensure that no gas from the pipe enters the module 13.

FIG. 30L is a cutaway view of the camera module 13 of FIG. 30K and FIGS. 30M and 30N are end views of the camera module 13 of FIG. 30K. As seen in FIG. 30M, the housing 306 contains a central camera lens 305 and multiple LED cluster lenses (light sources) 307. The embodiment shown in FIG. 30M contains 4 cluster lenses 307. However, any number of lenses may be used for optimum viewing and processing capabilities. FIG. 30P is a side view of the camera module 13 of FIG. 30K and FIG. 30Q is a view of the camera module 13 of FIG. 30K.

FIG. 30R is a diagram illustrating an embodiment of the patch module 18 of the multi-module pipe inspection and repair device 10 of the present invention. The module 18 includes a bladder module 15 and a supply module 17. The supply module 17 supplies a compressed gas such as nitrogen to the bladder module 15. The bladder module 15 then provides a patch, such as a polyurethane patch which has been treated with epoxy, with or without a metal sleeve, to the area of the pipe needing repaired.

FIG. 30S is a cutaway view of the patch module 18 of FIG. 30R along the A—A axis of FIG. 30T. The supply module 17 includes circuit boards 400 having the electronics needed to control the patch module 18. Tanks 402 contain a gas such as, for example, nitrogen, which is used to expand an inflatable bellows 404 in the bladder module 15. The bellows 404 may be constructed of, for example, rubber. A regulator 406 regulates the gas passing through a supply tube 408 in the supply module 17 and into a supply tube 410 in the bladder module 15. The regulator 406 may contain a two-way valve which allows the gas to travel in the desired direction. The gas from the supply module 17 thus may inflate the bellows 404 such that the patch 320 contacts the walls of the pipe to be repaired. The patch contains a felt layer which is soaked in epoxy and wrapped onto the rubber sleeve before the patch is installed on the bladder module 15. The patch set module 18 can use, for example, Link-Pipe and Snap-Lock patches.

FIGS. 30T and 30U are end views of the patch module 18 of FIG. 30R and FIGS. 30V and 30W are views of the patch module 18 of FIG. 30R.

FIG. 30X illustrates an exploded view of an embodiment of the centralizer 290 of the multi-module pipe inspection and repair device 10 of the present invention. The centralizer 290 includes a ring 312 to which cables 314 are attached. The cables 314 can be attached to the ring 312 by any suitable method such as, for example, soldering, gluing with epoxy, welding, etc. The cables 314 can be constructed of, for example, braided steel with, for example, steel spheres 316 attached to the ends of the cables 314. A dowel pin 318 locates the ring 312 to an attaching flange on the module to which the centralizer 290 is attached.

FIG. 30Y is a cutaway view of the centralizer 290 of FIG. 30X along the A—A axis of FIG. 30AA. FIGS. 30Z and 30AA are views of the centralizer of FIG. 30X.

FIG. 30AB is a cutaway view of an embodiment of a patch assembly 320 which may be used with the patch module 18 of FIG. 30R. FIG. 30AC is a magnified cutaway view of a portion 322 of the patch assembly 320 of FIG. 30AB. The patch assembly 320 includes a rubber patch 324 located around the bladder module 15. Epoxy-filled felt 326 is located on the patch 324. A steel sleeve 328 is attached to the assembly 320 such that when the bellows 404 of the bladder module 15 expands and the epoxy-filled felt 326 contacts the pipe wall, the sleeve 328 remains rigid and keeps the assembly 320 in contact with the pipe wall so that a thorough seal is created to repair the pipe. A thin plastic sleeve 330 is held onto the assembly 320 with a rubber band 332. The sleeve 330 is perforated at 334 so that it may tear away from the assembly 320. The sleeve 330 keeps foreign particles (e.g. particles in the pipe) from interfering with the seal that the patch 324 must make with the wall of the pipe to be repaired. When the patch 324 is set, the expansion of the bellows 404 of the bladder module 15 causes the sleeve 330 to tear away from the patch 324 at the perforation 334.

FIG. 30AD is a schematic representing electrical connections of the multi-module pipe inspection and repair device 10 of the present invention. Electrical connections for the connector 34, the base 12, and the marker module 38 with the MFL module 36, the sensor module 19 with the brush module 16, the patch module 18, and the camera module 13.

FIG. 30AE is a block diagram illustrating various electrical components of the base module 12 and the user interface 26 of the present invention. The interface 26 includes the indicator lights and controls 222 and a control equipment CPU 336, which is located on the controller board 226. The CPU 336 can be, for example, a Hitachi H-8, Motorola 68030, or any other suitable microprocessor manufactured by, for example, AMD or Intel. An RS-422 interface 338 provides an interface between the interface 26 and the coiled tubing 22.

The base module 12 includes a base module microcontroller 340. The microcontroller 340 can be, for example, a Hitachi H-8, Motorola 68030, or any other suitable microprocessor manufactured by, for example, AMD or Intel. The module 12 also includes an RS422 interface 342 which provides an interface between the base module 12 and the coiled tubing 22. Pressure sensors 344 are located in each of the modules. The sensors 344 can be, for example, differential pressure sensors such as those manufactured by Entran Corp. The sensors 344 function such that if there is a low pressure differential between the pressure inside the module and the pressure outside the module, the module will be shut down removed.

Diffuse light sensors 346 are located in the sensor module 19. The sensors 346 detect the mark left by the marker module 38. The sensors can be, for example, those manufactured by Sunex Corp. The sensors 346 may also be used in the patch module 18 to detect the location on which the patch should be placed.

Brush/mark/patch actuators 348 are located in the brush module 18, the marker module 38, and the patch module 18 to control their respective functions (i.e. brushing the pipe, spraying a marker, and inflating/deflating the bellows).

Figure 31:
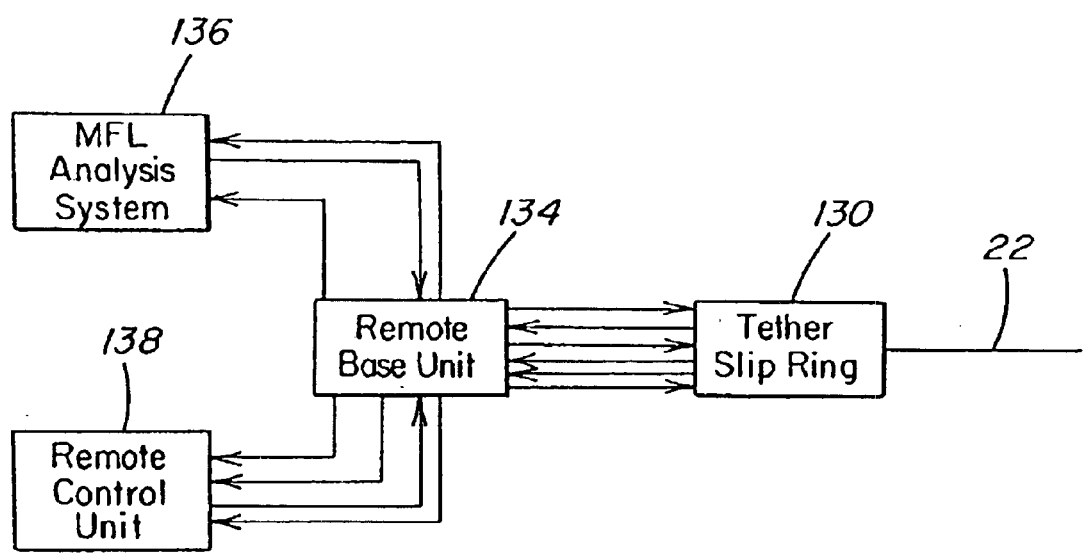
FIG. 31 illustrates the electronic components which make up the offboard support for the multi-module pipe inspection and repair device of the present invention.

FIG. 31 illustrates the electronic components which make up the offboard support for the device 10. A tether slip ring 130 breaks out the cables inside the coiled tubing tether 22 into individual conductors. This allows the tubing to be coiled without twisting the cable inside. The tether slip ring 130 can be, for example, an off-the-shelf slip-ring. The electronics include a remote base unit 134, an MFL analysis system 136, and a remote control unit 138.

The tether slip ring 130 connects directly to the cables passed through the coiled tubing tether 22. A sliding brush system allows the ring 130 to rotate freely, while maintaining an electrical connection. The brush contacts connect to the remote base unit 134, where various breakouts occur.

Figure 31A:
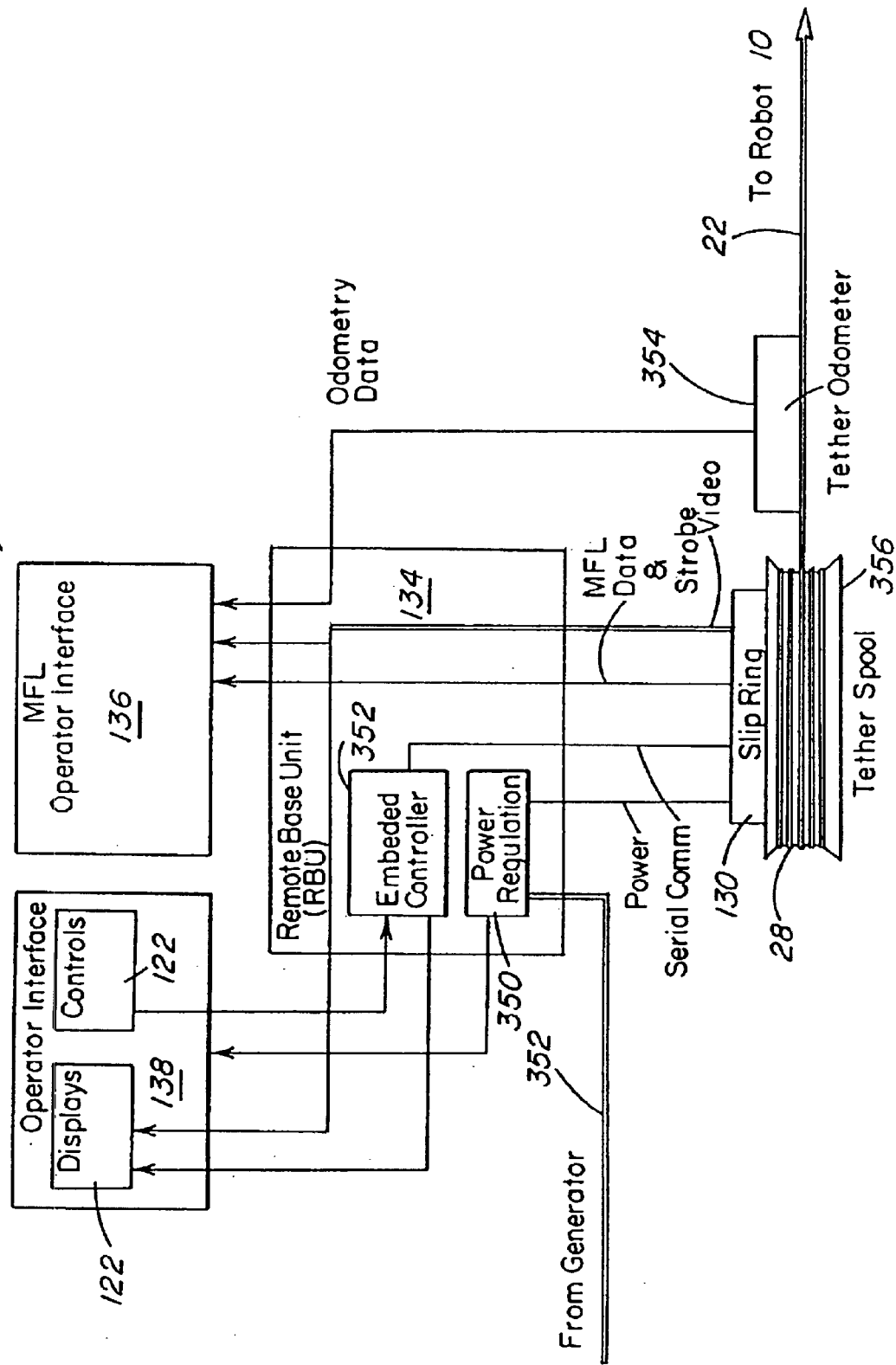
FIG. 31A illustrates a block diagram of an embodiment of the signal flow to and from the user interface.

FIG. 31A illustrates a block diagram of an embodiment of the signal flow to and from the user interface 26. The interface 26 includes the operator interface 138, the MFL operator interface 136, and the remote base unit 134. The remote base unit 134 includes a power regulation module 350 and an embedded controller 352. A power line 352, from a generator (not shown), supplies power to the power regulation module 350 during operation.

A tether odometer 354 provides odometry data to the interface 26 concerning the amount of coiled tubing 22 which has been dispensed from the coiled tubing unit 28. The coiled tubing unit 28 includes a tether spool 356 around which the coiled tubing 22 is wound. The unit 28 also includes the slip ring 130 which controls the amount of coiled tubing 22 which is dispensed and provides an interface for the interface 26 to received the various signals from the device 10 which are transmitted from the device 10 via the coiled tubing 22.

Figure 32:
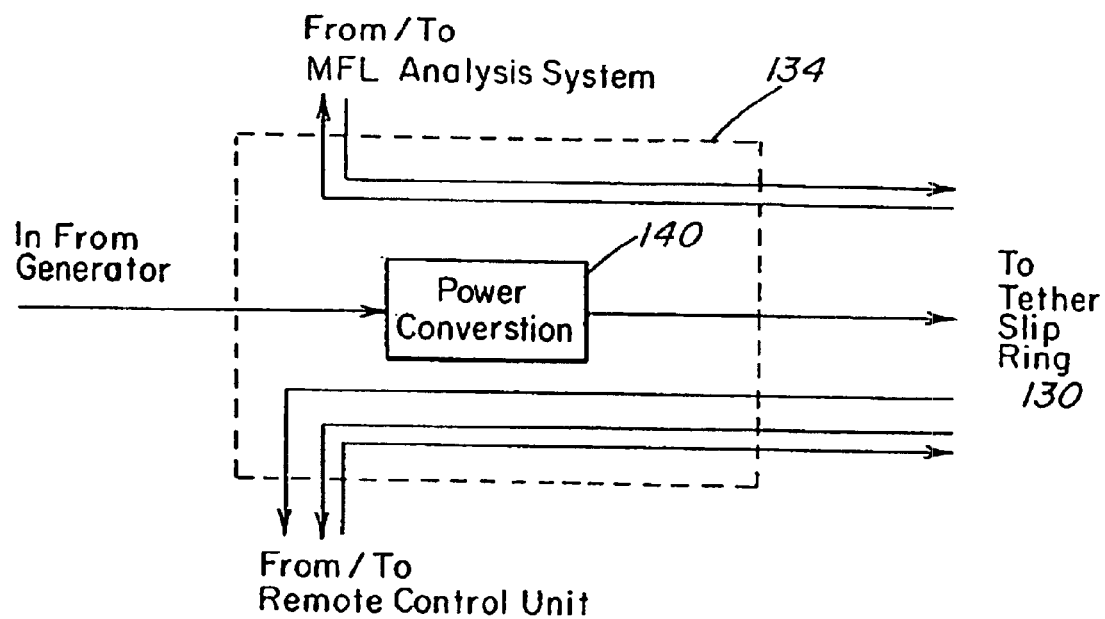
FIG. 32 is a diagram illustrating the layout of the remote base unit of FIG. 31.

FIG. 32 is a diagram illustrating the layout of the remote base unit 134 of FIG. 31. The remote base unit 134 provides a centralized hub for the offboard equipment. The unit 134 may contain power regulation, communications and computing equipment for operating the device 10.

The remote base unit 134 connects directly to the tether slip ring 130. Power is passed to the deployment head through this connection, and video, serial, and MFL data & strobe connections are made.

Two modules are connected to the "upstream" side of the remote base unit 134. The MFL Analysis System generates the MFL strobe signal and receives MFL data when the MFL module 36 is mounted on the device 10. The remote control unit 138 is passed the video and serial data from the device 10, and generates control commands for the entire system 24.

A power conversion module 140 converts the electrical power (e.g. 110VAC) produced by an offboard generator to, for example, 150VDC passed down to the deployment head via the tether 22.

Figure 33:
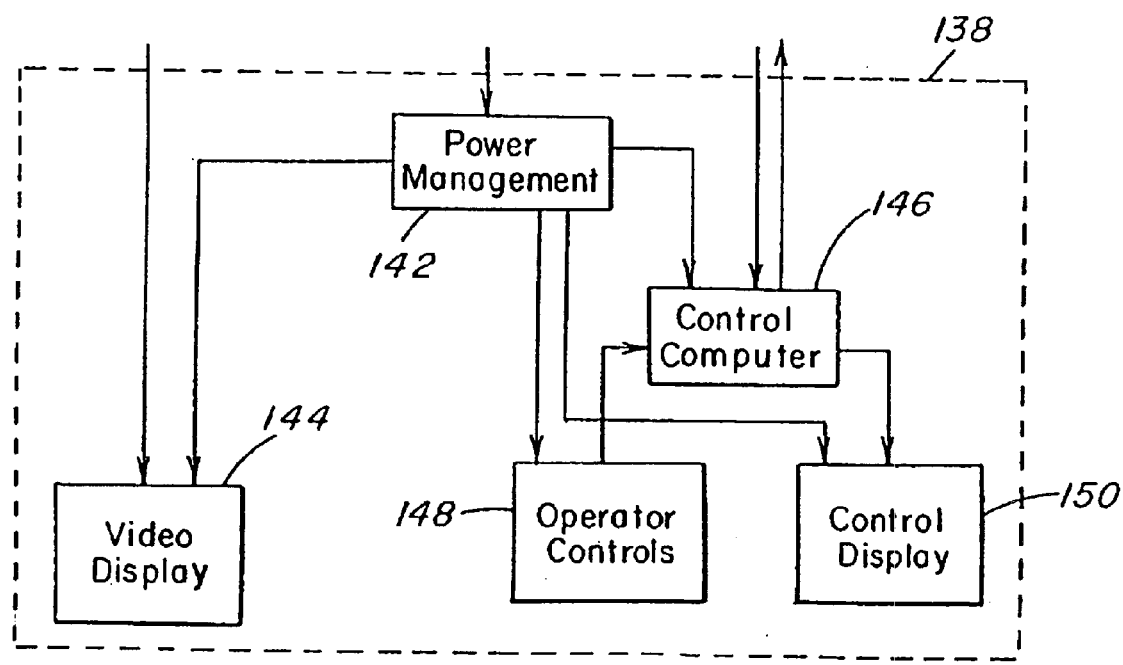
FIG. 33 illustrates the layout of an embodiment of the remote control unit of FIG. 31.

FIG. 33 illustrates the layout of an embodiment of the remote control unit 138 of FIG. 31. A power management module 142 distributes electrical power to all of the other components. A video display 144 provides the operator with live video from the device 10, when a module with video capability (e.g. the prep module 16 or the patch module 18) is installed. A control computer 146 monitors the status of the various operator controls 148, sending control messages to the deployment head and producing feedback to the operator via a control display 150. The remote control unit 138 can be, for example, an embedded-type PC system with an LCD display and the necessary buttons and levers for operator interaction.

The MFL analysis system 136 outputs an MFL strobe signal to be passed to the device 10, and receives the MFL data for analysis.

Figure 34:
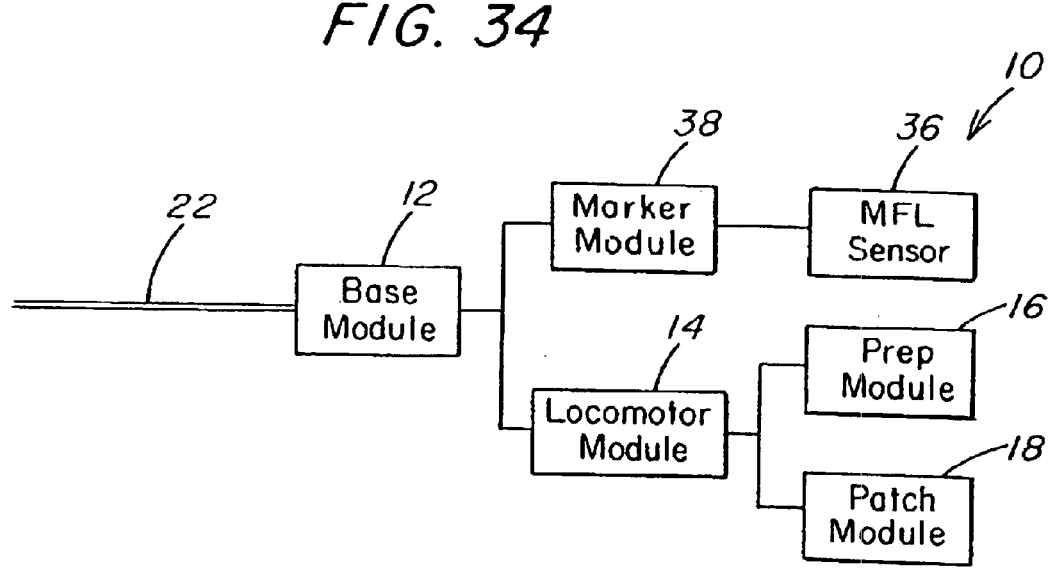
FIG. 34 is a diagram illustrating three configurations of the multi-module pipe inspection and repair device of the present invention.

FIG. 34 is a diagram illustrating three configurations of the device 10, as described hereinabove. A typical deployment of the device 10 follows a sequence of actions, as follows.

1. Marking Flaws: The first step in repairing a section of pipe is to map and mark all of the flaws. For this, the base module 12, the marker module 38, and the MFL module 36 are all connected to the end of the coiled tubing umbilical. The MFL module 36 is used to locate the flaws, and the marker module 38 tags each with, for example, an indelible visual mark or any type of mark, either visual or not, which can be used to later locate each flaw.
2. Pipe Prep: After the flaws have been located and marked, the base module 12, the locomotor module 14 (optional), and the prep module 16 are connected. The brushes (or star-shaped wheels) contained in the prep module 16 are used to vigorously scrub or abrade the inside of the pipe, while the locomotor module 14 or the system operator pushes the prep module 16 back and forth over the flaw, increasing the total prepared length.
3. Pipe Patch: After each patch site has been prepared, the base module 12, the locomotor module 14 (if used), and the patch module 18 are used to install a patch over the flaw.

Figure 35:
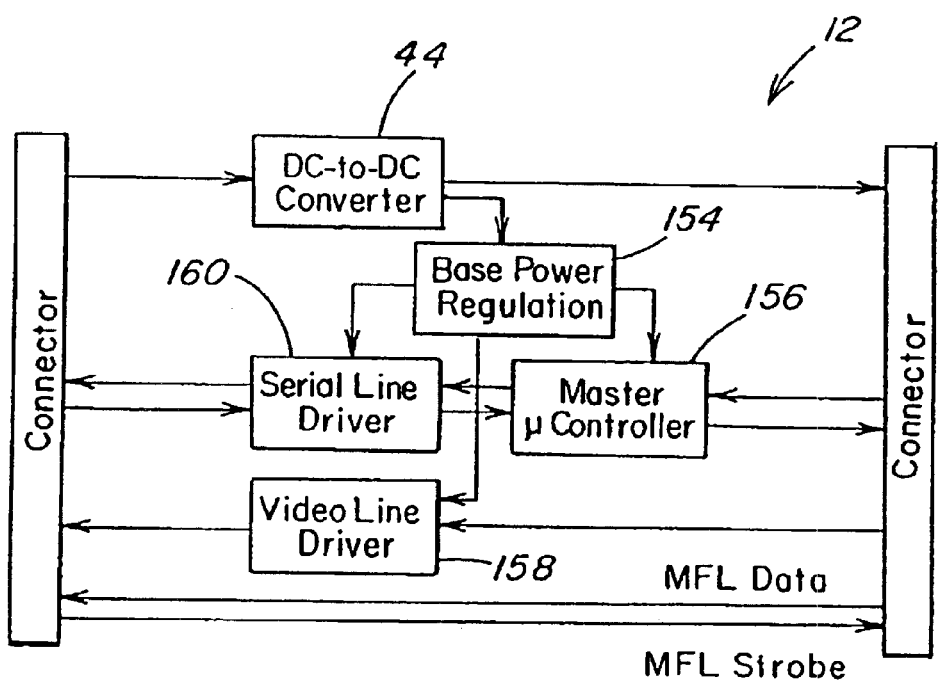
FIG. 35 illustrates a layout of the electronic components of the base module.

FIG. 35 illustrates a layout of the electronic components of the base module 12. The electronics of the base module 12 consists of three main parts: the primary power conversion 44 and regulation circuitry 154, the primary controller 156, and the line drivers 158, 160 for pushing video and serial communications over the long lengths of the tether 22.

The base module 12 connects directly to the tether 22 on one end; the other end can be connected either to the locomotor module 14 or one of the effector modules (e.g. the marker module 38, the prep module 16, or the patch module 18).

The DC-to-DC converter 44 steps the 150VDC line voltage down to 48V for use in other modules. A base power regulation module 154 steps the 48V output of the DC-to-DC converter 44 down to the lower voltages required by the other components in the base module 12. A master $\mu$controller 156 is responsible for handling communications between the offboard equipment and the other onboard micro controllers. A video line driver 158 provides the ability to carry video over the entire length of the tether 22 without significant degradation of the signal. A serial line driver 160 provides high-speed serial communication (e.g. RS-232) over the length of the tether 22. MFL data and strobe lines are passed through the base module 12, in order to be connected to the MFL module 36 when it and the marker module 38 are part of the device 10.

The micro controller 156 in the base module 12 serves as the master controller for the entire device 10, passing operator commands downstream to the other onboard controllers in other modules and handling status data transmissions upstream to the control station. The software kernel running on the micro controller 156 is partitioned into the following functional units.

RS-232 (Upstream) Serial Communications: An interface to the serial line driver 160 handles bidirectional, asynchronous serial communication over the tether 22.

I2C (Downstream) Serial Communications: An I2C software module implements this multi-receiver protocol to allow the master controller 156 to communicate with several slave controllers.

Pressure Sensing: Absolute and/or relative pressure sensors are integrated into the micro controller 156 to guard against leaks in the base module 12. Upon the detection of a leak, the entire device 10 is electrically shut down and manually removed from the pipe using the coiled tubing system 28.

Figure 36:
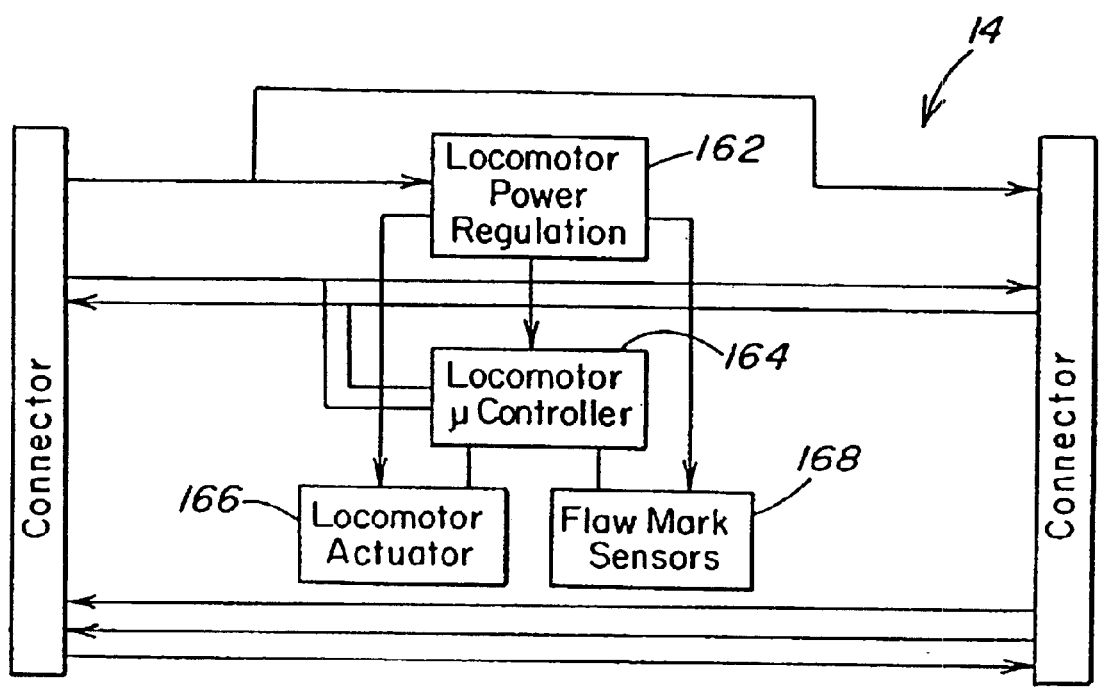
FIG. 36 illustrates a layout of the electronic components of the locomotor module.

FIG. 36 illustrates a layout of the electronic components of the locomotor module 14. The locomotor module 14 contains a linear actuator 166 which allows small movements to the attached effector module to be made with higher precision than that available from the coiled tubing drive alone.

The actuator 166 inside the locomotor module 14 pushes the solid ram 88 in and out of the body of the module 14. The end of the ram 88 is attached to the base module 12; thus, the body of the locomotor module 14 moves back and forth along with whichever effector is connected to the body of the module 14.

A locomotor power regulation module 162 steps down the 48V passed from the base module 12 to the various voltages required by the other components in the module 14. A locomotor μcontroller 164 receives commands via the inter-module serial bus. These commands are processed and passed to the locomotor actuator 166 using flaw mark sensors 168 as feedback for positioning operations. MFL data and strobe lines, as well as the video connection, are passed through the module 14.

The micro controller 164 in the locomotor module 14 is responsible for controlling the locomotor actuator 166. The following software modules are part of the kernel of the controller 164.

I2C Serial Communications: Commands from the controller 156 are received over this bus, and module status data is sent back.

Locomotor Actuator Control: Motor driver circuitry and actuator position sensing are integrated into the controller 164. This software module outputs control signals to the motor control circuitry, and monitors the position sensors during operation.

Pressure Sensing: Absolute and/or relative pressure sensors are integrated into the micro controller 164 to guard against leaks in the locomotor module 14. Don the detection of a leak, the device 10 is electrically shut down, and manually removed from the pipe using the coiled tubing system 28.

Figure 37:
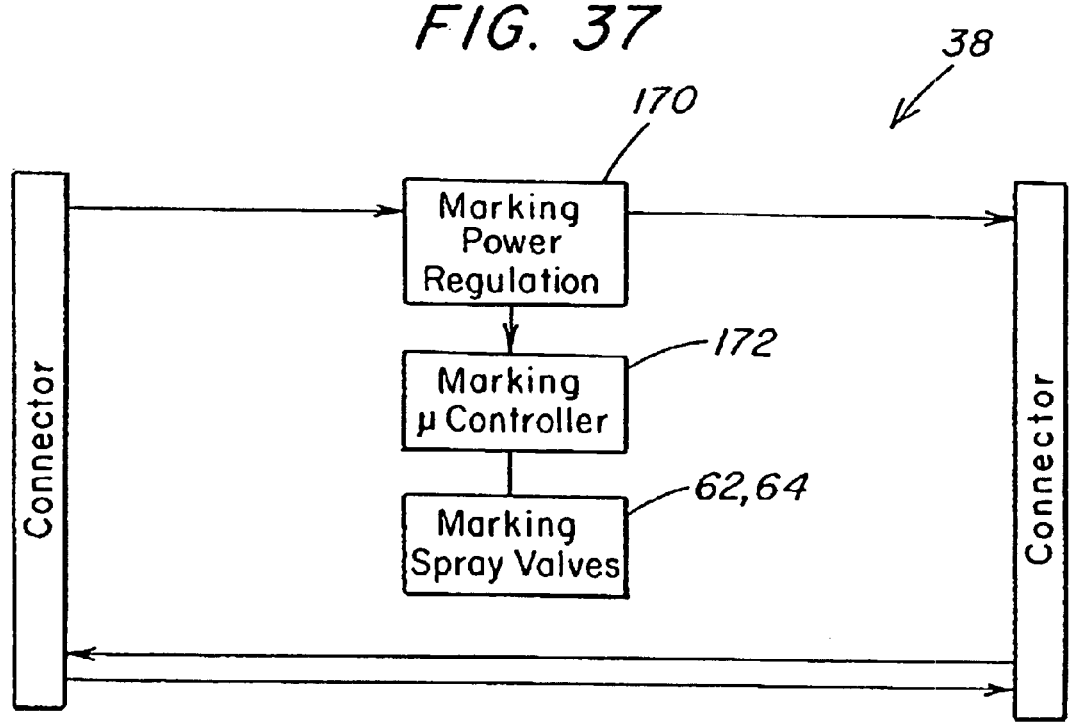
FIG. 37 illustrates a layout of the electronic components of the marker module.

FIG. 37 illustrates a layout of the electronic components of the marker module 38. The marker module 38 is the first effector module to be inserted into the pipe. It provides the capability, through a system of pressurized chambers and electronically-controlled valves 62 and 64, to mark the inside of the pipe with an indelible ring at a specified distance from each flaw.

The marker module 38 connects on one end to the base module 12 (or to the locomotor module 14, if additional positioning accuracy is necessary), and on the other end to the MFL module 36. On the MFL side, an MFL connector is used so that no rewiring is required.

A marking power regulation module 170 steps down the 48V passed along by the previous module to the lower voltages required by the other portions of the module 38. In addition, 9VDC is generated and passed to the MFL module 36. A marking μcontroller 172 receives commands over the inter-module serial bus, and executes these commands by passing control signals to the marking spray valves 62 and 64 which control operation of the spray nozzles on the nozzle head 66. MFL data and strobe lines are passed through the module 38 to the MFL module 36.

The micro controller 172 has the task of regulating the opening and closing of the valves 62 and 64 which control the marking mechanism. The following software modules comprise the kernel running on the controller 172.

I2C Serial Communications: This serial bus provides a method of communication between the marker module micro controller 172 and the master micro controller 156 in the base module 12, for the purpose of passing commands and status messages.

Valve Control: A module inside the kernel handles the electrical I/O required to interface to the marking valves 62 and 64.

Pressure Sensing: Absolute and relative pressure sensors are integrated into the micro controller 172 to guard against leaks in the marker module 38. Upon the detection of a leak, the device 10 is electrically shut down and manually removed from the pipe using the coiled tubing system 28.

Figure 38:
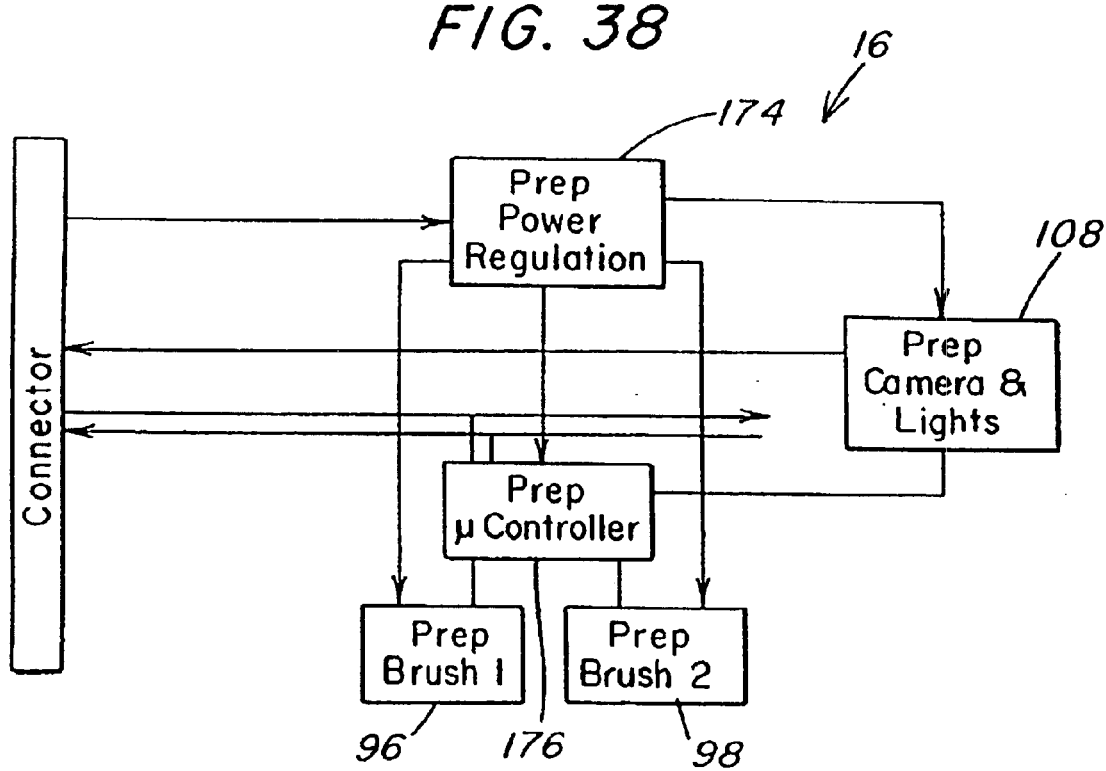
FIG. 38 illustrates a layout of the electronic components of the prep module.

FIG. 38 illustrates a layout of the electronic components of the prep module 16. The prep module 16 contains two brushes 96 and 98 which scour the inside of the pipe, to produce a clean surface upon which a patch may be installed. A forward-looking camera 108 with a high-intensity LED light ring is included to provide visual inspection capabilities.

The prep module 16 connects only on one end. It may be attached to the base module 12 alone or to the end of the locomotor module 14. A prep power regulation module 174 steps down the 48V passed in from the previous module to the lower voltages required by the other components inside the module 16. A prep μcontroller 176 receives commands over the inter-module serial bus. Brushless motor commutation is generated for the brushes 96 and 98, which drive the brush mechanisms directly. The prep camera & lights 108 are used to generate a view looking forward inside the pipe from the front of the module 16. The camera can be, for example, a high-resolution color CCD or CMOS model, and the lights can be, for example, high-intensity white LEDs.

The microcontroller 176 has the task of controlling the brush motors. This is a non-trivial task, because brushless motors are used for their high power ratings and small size. The need to sequence the power applied to their windings in response to their integrated hall sensor feedback are critical to the controller 176. In general, the following software modules are used.

2C Serial Communications: As in the other modules, an interface to this serial bus allows bidirectional communication between the controller 176 and the master controller 156 in the base module 12.

Brush Motor Control: Integrated hall sensor feedback and motor Over circuitry are interfaced by a software module designed to properly step the motor through its phases. This requires a fairly high-speed execution loop, and can be implemented by partitioning the module into a dual-controller architecture.

Pressure Sensing: Absolute and relative pressure sensors are integrated into the micro controller 176 to guard against leaks in the prep module 16. Upon the detection of a leak, the device 10 is electrically shut down, and manually removed from the pipe using the coiled tubing system 28.

Figure 39:
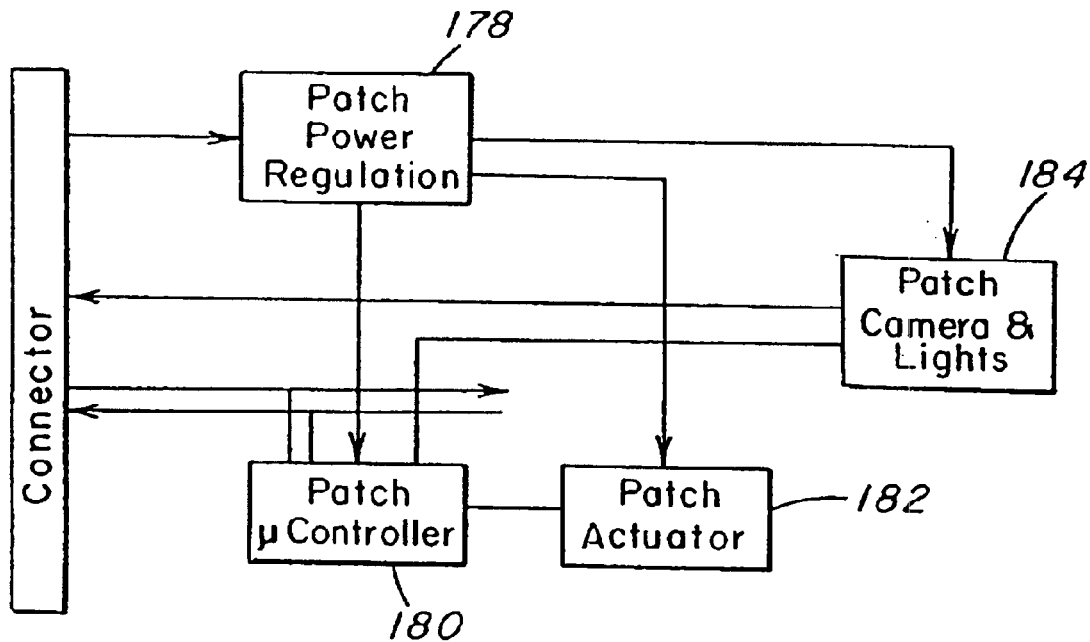
FIG. 39 illustrates a layout of the electronic components of the patch module.

FIG. 39 illustrates a layout of the electronic components of the patch module 18. The patch module 18 carries a collapsed patch into the pipe and then deploys it, sealing the previously located flaw.

The patch module 18 can connect on one end to the locomotor module 14 or directly to the base module 12. A patch power regulation module 178 converts the high-voltage input to levels suitable for the other electronic components. A patch μcontroller 180 receives commands from the inter-module serial bus, and carries out those commands via a direct interface to a patch actuator 182. Depending on the type of patch used, the actuator 182 may be, for example, a heating element or pneumatic valves. Patch camera & lights 184 provide the operator with a view of the inside of the pipe ahead of the device 10.

The following software modules may be implemented in the controller 180.

I2C Serial Communications: Bidirectional communication with the master controller 156 is facilitated by this link.

Patch Actuator Control: This module interfaces to the actuator 182 used to deploy the patch.

Pressure Sensing: Absolute and relative pressure sensors are integrated into the micro controller 180 to guard against leaks in the patch module 18. Upon the detection of a leak, the device 10 is electrically shut down and manually removed from the pipe using the coiled tubing system 28.

Figure 40:
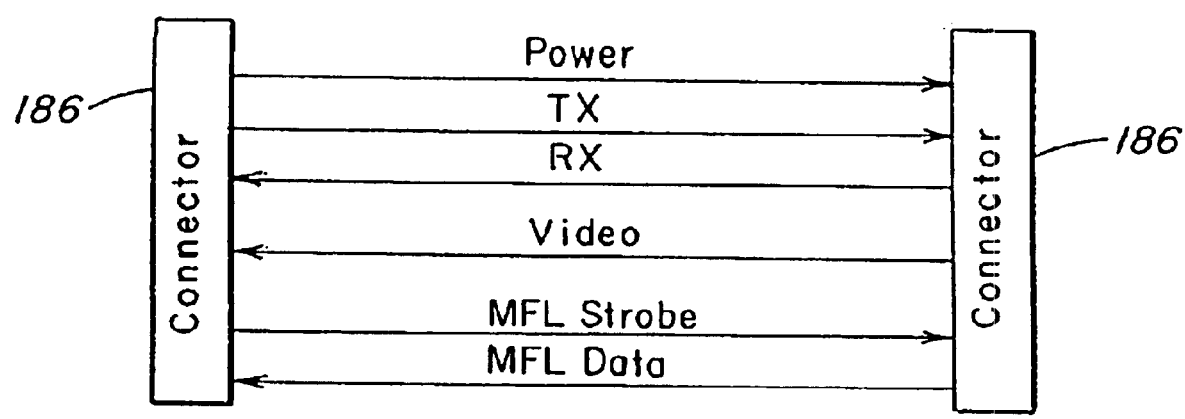
FIG. 40 illustrates connections and lines of the tether.

FIG. 40 illustrates connections and lines of the tether 22. The tether cable 22 serves as physical, as well as power, and signal linkage between the offboard controller and the device 10. A stainless steel tether housing holds 1000 feet of all the power and communication lines between the device 10 and the user interface computer 26.

The tether cable 22 may contain 5 twisted pairs and a single coaxial cable as outlined in Table 1. Both sides of the tether 22 may be terminated with slip-ring connectors 186.

TABLE 1

| FUNC-TIONALITY | SIGNAL TYPE | CABLE TYPE | GAUGE | # OF CONDUCTORS |
|---|---|---|---|---|
| Video camera signal | Video | Twisted Pair | 22 | 1 |
| Power | 150 VDC | Twisted Pair | 18 | 1 |
| Serial Communication | RS232C Transmit (TX) | Twisted Pair | 22 | 1 |
|  | RS232C, Receive (RX) | Twisted Pair | 22 | 1 |
| MFL Strobe Activation | MFL Strobe | Twisted Pair | 22 | 1 |
| MFL Data | Analog MFL Data | Coaxial | N/A | 1 |

The device 10 may require operation in a mixed and 100% methane environment at elevated pressures (e.g. <75 to 100 psig) and ambient temperatures (−20° C.<T<45° C.). Towards that end, the device 10 has to operate without creating a failure condition with repercussions to the operating crew, the general public and the distribution pipeline. Thus, the device 10 must not get stuck and become irretrievable and ignition of any gas in the pipe must be avoided.

In case of a complete system failure, the device 10 is retrievable due to its physical attachment to the coiled-tubing 22—as long as the tubing can be extracted, so will the device 10. Intermodule connections can be backed up with safety wire to ensure limited stretch and physical interconnection.

The safing features for the device 10 revolve around air-purging, nitrogen-pressurization above ambient and internal pressure-monitoring of each individual module, with an operator-alert and backup safety shutdown based on an acceptable pressure threshold. The use of absolute and/or relative pressure sensors monitored by the resident CPU in each module and communicating to the topside controller over the common communications bus, can be used to ensure a safe operating scenario.

The following is an embodiment of an electronic architecture for the device 10. A single CPU can reside in the base module 12 and communicate to the topside CPU in the interface 26 by way of a serial connection (or any other type such as fiber-optic, ethernet, etc.). The pins of the intermodule connectors 20 are all pre-assigned and mapped so as to allow the CPU to send the correct signals to the individual modules. The add-on modules are detected by the base module CPU, allowing it thus to decide what signals to send through what pins, and which pins to monitor for what feedback purpose, through a series of precision resistors in each module, which when connected in series through the intermodule connectors 20, yield a specific resistance-value which can be matched to a pre-measured value in a look-up table. This scheme allows the base module 20 ascertain the module it is connected to and thus which mode it should be operating in. This also allows the base module 20 to detect if an incorrect module or improper sequence of modules has been connected and thus shut down operation. In addition, the internal pressure sensor measurements in each module are tied to an analog comparator, which creates an open or closed circuit connection on a pin of the intermodule connector 20 (normally closed)—when the base module CPU monitors that line (or pin) it will detect an open circuit in case of a pressure failure, allowing it to shut down the entire system, requiring it to be removed from the pipe prior to re-setting. The sensor module works in a similar manner, in that it generates a high or low signal through a comparator analog circuit, which alerts the base module CPU that it is aligned with the marker by way of the CPU monitoring a dedicated pin on the intermodule connector 20, which in turn is communicated up to the topside CPU and displayed visually and audibly to the operator so as to denote proper alignment.

Figure 41:
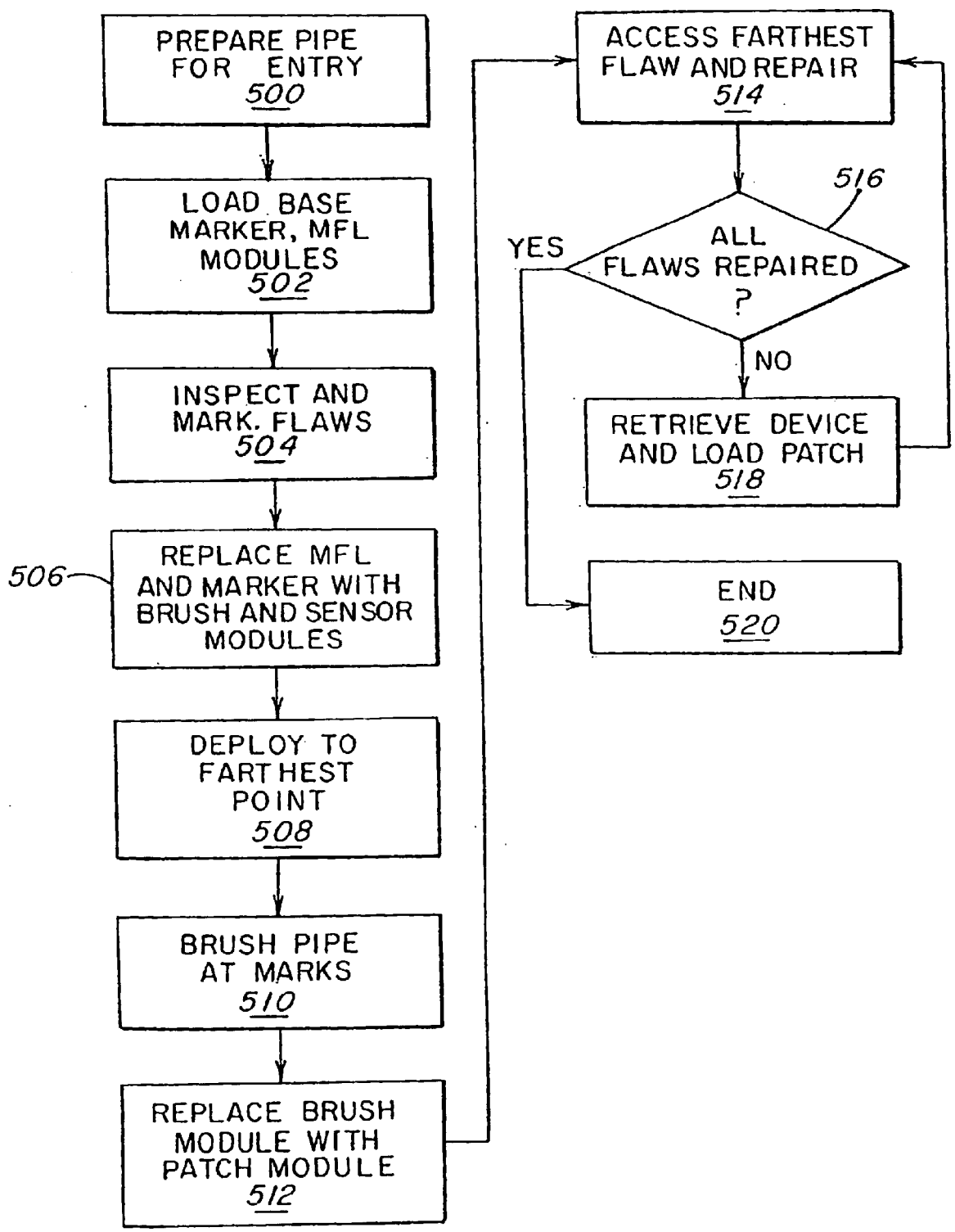
FIG. 41 is a flowchart illustrating a method of using the multi-module pipe inspection and repair device of the present invention.

FIG. 41 a flowchart illustrating an embodiment of a method of using the multi-module pipe inspection and repair device of the present invention. At step 500, the pipe 210 which needs to be repaired is prepared for entry by digging a hole, installing the access system 30, and drilling a coupon from the pipe 210. At step 502, the device 10 is prepared by attaching the base module 12, the marker module 38, and the MFL module 36 to the coiled tubing 22. The device 10 is then inserted into the pipe and at step 504 the pipe is inspected and flaws are marked by the marker module 38. At step 506, the marker module 38 and the MFL module 36 are replaced with the brush module 16 and the sensor module 19. At step 508, the device 10 is deployed into the pipe 210 at its farthest point. At step 510, the device 10 navigates the pipe 210 and brushes the walls of the pipe at each marker applied at step 504 by the marker module 38.

At step 510, the brush module 16 and the sensor module 19 are replaced with the patch module 18 and the device is deployed to the farthest flaw of the pipe 210 at step 514. The flaw is then repaired by the patch module 18 and, at step 516, it is determined if all flaws have been repaired. If not, the flow proceeds to step 518, where a new patch 320 is loaded onto the bladder module 15. The flow then proceeds to step 514, where the next flaw is located and repaired. If all flaws were repaired as determined at step 516, the flow ends at step 520.

A shape memory repair method based upon the use of a class of metal alloys referred to as "Shape Memory Alloys" (SMA) may be used by the patch module 18 to repair flaws in pipe. Such a technique is illustrated in U.S. Pat. No. 5,040,283 entitled "Method of Placing a Body of Shape Memory Within a Tube", which is incorporated herein by reference. These alloys have the ability to be heat treated to establish a given shape as a "remembeeed" state. Subsequently, the metal shape is plastically deformed. Reheating above a "transition temperature" determined by percentages of the alloy metals causes the distorted shape to return to its "remembered" state.

Figure 42:
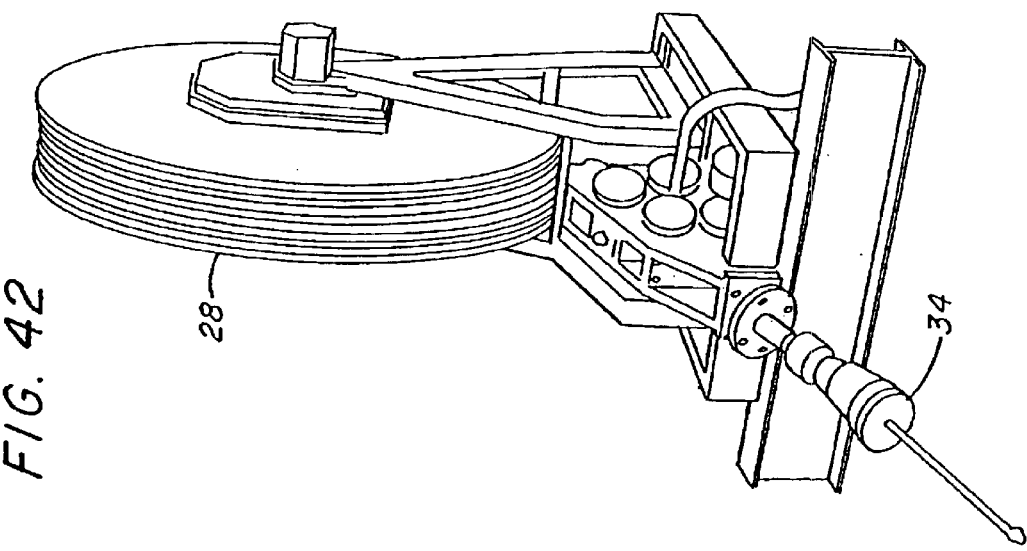
FIG. 42 illustrates an embodiment of the coiled tubing unit of the present invention.

FIG. 42 illustrates an embodiment of the coiled tubing unit 28 of the present invention.

Figure 43:
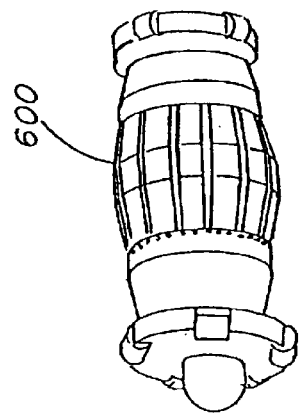
FIG. 43 illustrates an embodiment of the sensor used in the FL module of the present invention.

FIG. 43 illustrates an embodiment of a sensor 600 used in the MFL module 36 of the present invention. The sensor 600 may consist of, for example, multiple (e.g. 32) Hall-effect sensors, on a bi-directional mount and mounted between magnet poles, which measure true field levels independent of the velocity of the sensor 600.

While the present invention has been described in conjunction with preferred embodiments thereof, many modifications and variations will be apparent to those of ordinary skill in the art. The foregoing description and the following claims are intended to cover all such modifications and variations.

We claim:

1. A multi-module pipe repair inspection device, comprising:
    a base module;
    a microprocessor;
    at least two interchangeable tooling modules;
    a first flexible joint having electrical connection means, said joint flexibly, electrically and releasably connecting the base module to a selected one of the interchangeable tooling modules; and,
    a second flexible joint having electrical connection means, said joint flexibly, electrically and releasably connected between the interchangeable tooling modules,
    wherein each of said first and second joints is comprised of end portions, a spring positioned between said end portions defining a passage therethrough, and a flexible wire for electrically interconnecting adjacent modules to pass control and feedback signals from one module to another.

2. The device of claim 1, further comprising a locomotor module positioned between the base module and the tooling module.

3. The device of claim 2, wherein the locomotor has a stepper motor.

4. The device of claim 1, wherein the tooling module is a camera module.

5. The device of claim 4, further comprising a centralizer connected to the camera module.

6. The device of claim 4 wherein there are at least three interchangeable tooling modules, said tooling modules comprising a marker module connected to the camera module and an MFL module connected to a marker module.

7. The device of claim 4 wherein there are at least three interchangeable tooling modules, said tooling modules comprising a sensor module connected to the camera module and a brush module connected to the sensor module.

8. The device of claim 2 further comprising a patch set/test module.

9. The device of claim 1 wherein the tooling module is a marker module connected to the base module and the device further comprises an MFL module connected to a marker module.

10. The device of claim 9, further comprising a locomotor module connected between the base module and the marker module.

11. The device of claim 10, further comprising a flexible joint connected between the locomotor module and the marker module.

12. The device of claim 9, further comprising a flexible joint connected between the MFL module and the marker module.

13. The device of claim 9, further comprising a centralizer connected to the marker module.

14. The device of claim 9, wherein the marker module includes:
    a gas source;
    a regulator connected to the gas source;
    a marker valve connected to the gas source;
    a purge valve connected to the gas source;
    a marker reservoir tank connected to the marker valve;
    a check valve connected to the purge valve; and
    a nozzle head connected to the check valve.

15. The device of claim 1, wherein the interchangeable tooling modules comprise:
    a sensor module connected to the base module; and
    a brush module connected to the sensor module.

16. The device of claim 15, further comprising an interchangeable locomotor module connected between the base module and the sensor module by additional flexible joints.

17. The device of claim 15, further comprising a centralizer connected to the sensor module.

18. The device of claim 15, wherein the brush module includes a camera.

19. The device of claim 15 further comprising:
    a camera and lighting positioned on said base module.

20. The device of claim 15, wherein the brush module includes a brush assembly, the brush assembly including at least one star-shaped brush wheel.

21. The device of claim 20, wherein the brush wheel is constructed of hardened steel.

22. The device of claim 20 wherein the brush assembly further includes a spring, wherein the spring keeps the brush wheel from contacting a wall of a pipe, and wherein rotation of the brush assembly causes tension on the spring to be overcome and the brush wheel contacts the wall of the pipe.

23. The device of claim 1 wherein the tooling module is a patch set/test module.

24. The device of claim 23, wherein the patch set/test module includes a bladder module and a supply module connected to the bladder module.

25. The device of claim 24, further comprising a flexible joint connected between the bladder module and the supply module, said joint having means for fluid connection between the bladder and supply modules.

26. The device of claim 24, wherein the supply module includes at least one tank and a regulator for regulating gas entry and exit from the tank.

27. The device of claim 24, wherein the bladder module includes an inflatable bellows for setting a patch to a wall of a pipe.

28. The device of claim 23, further comprising a locomotor module connected between the base module and the patch set/test module.

29. The device of claim 1 wherein the tooling modules comprise:
    a camera module;
    a sensor module;
    an MFL module;
    a brush module;
    a patch set/test module; and
    a marker module.

30. The device of claim 29, further comprising a locomotor module.

31. The device of claim 29, further comprising at least one centralizer connected to at least one of the modules.

32. The device of claim 29, further comprising at least one centralizer connected to each of the modules.

33. The device of claim 1 further comprising:
    a coiled tubing unit connected to the base module, said tubing unit having coiled tubing piping;
    a user interface in communication with the coiled tubing unit;
    a pipe access system connected to a pipe.

34. The system device of claim 33, further comprising an interface connector connected between the coiled tubing unit and the device.

35. The device of claim 33, wherein the user interface includes:
    a controller board;
    a user interface board in communication with the controller board;

a control panel in communication with the user interface board; and a monitor in communication with the controller board.

36. The device of claim 33, wherein the pipe access system includes:
   a sleeve attached to the pipe, the sleeve having a protruding portion;
   a valve assembly connected to the protruding portion; and
   an access tube connected to the valve assembly.

37. The device of claim 36, wherein the protruding portion is oriented at approximately a 20 degree angle relative to the pipe.

38. The device of claim 36, wherein the valve assembly includes one of a ball valve and a gate valve.

39. The device of claim 33, wherein the coiled tubing unit includes:
   a tether spool;
   a slip ring in communication with the spool and the user interface; and
   a tether odometer in communication with the user interface.

40. The device of claim 1, wherein said flexible wire passes through said passage and further comprising a sleeve positioned in said passage for shielding said flexible wire.

41. The device of claim 1 further comprising a member substantially surrounding said spring.

42. The device of claim 41 wherein said member is formed of wire mesh.

43. The device of claim 41 wherein said member is formed of cords fastened together.

44. A multi-module pipe repair inspection device, comprising:
   a base module;
   a microprocessor;
   an interchangeable sensor module connected to the base module;
   an interchangeable brush module connected to the sensor module;
   first and second flexible joints, each joint having electrical connection means, said first joint flexibly, electrically and releasably connecting the base module to the sensor module, and said second joint flexibly, electrically and releasably connecting the sensor module to the brush module, each said joint being comprised of end portions, a spring positioned between said end portions defining a passage therethrough, and a flexible wire bundle for electrically interconnecting the adjacent modules to pass control and feedback signals therebetween.

45. The device of claim 44 wherein said flexible wire bundle passes through said passage and further comprising a sleeve positioned in said passage for shielding said flexible wire bundle.

46. The device of claim 44 further comprising a member substantially surrounding said spring.

47. The device of claim 46 wherein said member is formed of wire mesh.

48. The device of claim 46 wherein said member is formed of cords fastened together.

49. The device of claim 44 further comprising means surrounding said spring for providing angular detention to prohibit over-rotation or over-translation of said spring.

50. The device of claim 49 wherein said means for providing angular detention is formed of wire mesh.

51. The device of claim 49 wherein said means for providing angular detention is formed of cords fastened together.

* * * * *

UNITED STATES PATENT AND TRADEMARK OFFICE
CERTIFICATE OF CORRECTION

PATENT NO.      : 6,820,653 B1
DATED           : November 23, 2004
INVENTOR(S)     : Schempf et al.

It is certified that error appears in the above-identified patent and that said Letters Patent is hereby corrected as shown below:

Column 2,
Line 10, insert a hyphen -- - -- between "4 inch".
Line 21, delete the hypen "-" after "flux".

Column 4,
Line 62, delete "280" and substitute -- 28G --.

Column 5,
Line 36, delete "," and substitute -- ; --.
Line 48, delete the hypen "-" after "patch".

Column 6,
Line 23, delete "FL" and substitute -- MFL --.

Column 12,
Line 41, delete "diffise" and substitute -- diffuse --.
Line 42, delete "detectors" and substitute -- detector --.

Column 14,
Line 48, delete "At".
Line 62, delete "301" and substitute -- 30I --.

Column 16,
Line 41, delete "RS422" and substitute -- RS-422 --.

Column 18,
Line 53, delete "12C" and substitute -- I2C (both occurrences) --.

Column 19,
Line 58, delete "12C" and substitute -- I2C --.

Column 20,
Line 30, delete "2C" and substitute -- I2C --.
Line 35, delete "Over" and substitute -- driver --.
Line 62, delete "12C" and substitute -- I2C --.

Column 22,
Line 53, delete "remembeeed" and substitute -- remembered --.

UNITED STATES PATENT AND TRADEMARK OFFICE
CERTIFICATE OF CORRECTION

PATENT NO. : 6,820,653 B1
DATED : November 23, 2004
INVENTOR(S) : Schempf et al.

It is certified that error appears in the above-identified patent and that said Letters Patent is hereby corrected as shown below:

Column 24,
Line 60, delete "system".

Signed and Sealed this

Twenty-first Day of March, 2006

JON W. DUDAS
*Director of the United States Patent and Trademark Office*